US012648917B2

(12) United States Patent
Ranum et al.

(10) Patent No.: US 12,648,917 B2
(45) Date of Patent: Jun. 9, 2026

(54) USE OF METFORMIN AND ANALOGS THEREOF TO REDUCE RAN PROTEIN LEVELS IN THE TREATMENT OF NEUROLOGICAL DISORDERS

(71) Applicant: University of Florida Research Foundation, Incorporated, Gainesville, FL (US)

(72) Inventors: Laura Ranum, Gainesville, FL (US); Tao Zu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 18/403,100

(22) Filed: Jan. 3, 2024

(65) Prior Publication Data

US 2024/0269093 A1 Aug. 15, 2024

Related U.S. Application Data

(63) Continuation of application No. 16/650,721, filed as application No. PCT/US2018/052913 on Sep. 26, 2018, now Pat. No. 11,903,910.

(60) Provisional application No. 62/563,588, filed on Sep. 26, 2017.

(51) Int. Cl.
*A61K 31/155* (2006.01)
*A61P 25/28* (2006.01)

(52) U.S. Cl.
CPC .................................. *A61K 31/155* (2013.01)

(58) Field of Classification Search
CPC .............................. A61K 31/155; A61P 25/28
See application file for complete search history.

(56) References Cited

U.S. PATENT DOCUMENTS 5,011,912 A 4/1991 Hopp et al.
6,204,008 B1 3/2001 Borneman et al.
6,326,151 B1 12/2001 Katze et al.
6,342,581 B1 1/2002 Rosen et al.
7,008,796 B2 3/2006 Wohlstadter et al.
7,481,997 B1 1/2009 Hardy
8,993,633 B2 3/2015 Megeney et al.
9,448,232 B2 9/2016 Petrucelli et al.
10,066,007 B2 9/2018 Edbauer et al.
10,295,547 B2 5/2019 Ranum et al.
10,392,447 B2 8/2019 Montrasio et al.
10,509,045 B2 12/2019 Ranum et al.
10,663,475 B2 5/2020 Ranum et al.
10,940,161 B2 3/2021 Ranum et al.
10,961,322 B2 3/2021 Montrasio et al.
11,034,974 B2 6/2021 Ling et al.
11,345,911 B2 5/2022 Ranum et al.
11,903,910 B2 2/2024 Ranum et al.
12,025,622 B2 7/2024 Ranum et al.
12,162,952 B2 12/2024 Grimm et al.
12,360,124 B2 7/2025 Ranum et al.
12,364,707 B2 7/2025 Ranum et al.
12,392,786 B2 8/2025 Ranum et al.
12,436,154 B2 10/2025 Ranum et al.
12,473,545 B2 11/2025 Ranum et al.
2002/0165355 A1 11/2002 Meheus et al.
2003/0113826 A1 6/2003 Wehner et al.
2003/0233675 A1 12/2003 Cao et al.
2005/0042657 A1 2/2005 Weese-Mayer et al.
2006/0068434 A1 3/2006 Stoerker
2007/0004729 A1 1/2007 Timmer et al.
2007/0014810 A1 1/2007 Baker et al.
(Continued)

FOREIGN PATENT DOCUMENTS

CA 3137666 A1 11/2020
EP 2 837 390 A1 2/2015
(Continued)

OTHER PUBLICATIONS

Cleary et al. Current Opinion in Genetics & Development 2017, 44, 125-134, available online Mar. 30, 2017.*
Cleary et al. Human Molecular genetics 2013, 22 (1), R45-R51.*
Batra et al. Human Molecular genetics 2010, 19 (1), R77-R82.*
Tandon et al. Life Sciences 2024, 344, 122562, p. 1-17.*
Cendelin et al. The Cerebellum 2022, 21, 452-481.*
Cui et al. Frontiers in Neuroscience 2024, 18:1422442, p. 1-15.*
International Preliminary Report on Patentability, mailed Jun. 13, 2024, in connection with Application No. PCT/US2022/051530.
International Preliminary Report on Patentability, mailed Sep. 12, 2024, in connection with Application No. PCT/US2023/063328.
(Continued)

*Primary Examiner* — Irina Neagu
(74) *Attorney, Agent, or Firm* — Wolf, Greenfield & Sacks, P.C.

(57) ABSTRACT

The present disclosure provides the use of compounds of Formulae (I), (II), (III), (III-A), and (III-B) (e.g., metformin) in treating a neurological disease associated with repeat expansions and/or RAN protein accumulation, reducing the level of one or more repeat associated non-ATG (RAN) proteins, and reducing the accumulation of RAN proteins in a subject and/or biological sample. Also provided is the use of compounds of Formulae (I), (II), (III), (III-A), and (III-B) (e.g., metformin) in inhibiting RAN protein translation in a subject and in a biological sample (e.g., cells, tissue). Also provided in the present disclosure are pharmaceutical compositions, kits, and uses of compounds of Formulae (I), (II), (III), (III-A), and (III-B) (e.g., metformin) for treating diseases associated with repeat expansions. Exemplary diseases associated with repeat expansions include, but are not limited to, C9ORFf72 amyotrophic lateral sclerosis (ALS), or C9ORFf72 frontotemporal dementia; myotonic dystrophy type 1 (DM1) and myotonic dystrophy type 2 (DM2); spinocerebellar ataxia; Huntington's disease; Fragile X Tremor Ataxia Syndrome (FXTAS); and Fragile XE syndrome (FRAXE).

15 Claims, 17 Drawing Sheets

Specification includes a Sequence Listing.

(56) References Cited

U.S. PATENT DOCUMENTS

| | | | |
|---|---|---|---|
| 2007/0036760 | A1 | 2/2007 | Wilson et al. |
| 2007/0093426 | A1 | 4/2007 | Wormser |
| 2008/0188457 | A1 | 8/2008 | Barlow et al. |
| 2008/0227699 | A1 | 9/2008 | Chiba et al. |
| 2008/0248099 | A1 | 10/2008 | Ishii |
| 2009/0074721 | A1 | 3/2009 | Kim et al. |
| 2009/0143418 | A1 | 6/2009 | Dixon et al. |
| 2009/0148866 | A1 | 6/2009 | Datwyler et al. |
| 2009/0312395 | A1 | 12/2009 | El-Tanani et al. |
| 2010/0298280 | A1 | 11/2010 | Kioschis-Schneider et al. |
| 2012/0076785 | A1 | 3/2012 | Nikolaev et al. |
| 2012/0094299 | A1 | 4/2012 | Ranum et al. |
| 2012/0142027 | A1 | 6/2012 | Kim |
| 2012/0220534 | A1 | 8/2012 | Levin et al. |
| 2013/0085169 | A1 | 4/2013 | Baghdoyan et al. |
| 2013/0115603 | A9 | 5/2013 | Ranum et al. |
| 2014/0100282 | A1 | 4/2014 | Wong |
| 2014/0336133 | A1 | 11/2014 | Miller et al. |
| 2015/0011729 | A1 | 1/2015 | Ranum et al. |
| 2015/0361166 | A1 | 12/2015 | Edbauer et al. |
| 2016/0025747 | A1 | 1/2016 | Ranum et al. |
| 2016/0096800 | A1 | 4/2016 | Walter et al. |
| 2016/0346297 | A1 | 12/2016 | Sheehan |
| 2017/0247471 | A1 | 8/2017 | Montrasio et al. |
| 2018/0050001 | A1* | 2/2018 | During ................. A61K 31/155 |
| 2018/0088111 | A1 | 3/2018 | Ni et al. |
| 2018/0292416 | A1 | 10/2018 | Ranum et al. |
| 2019/0142858 | A1 | 5/2019 | Ranum et al. |
| 2019/0153445 | A1 | 5/2019 | Seow et al. |
| 2019/0285652 | A1 | 9/2019 | Ranum et al. |
| 2020/0010567 | A1 | 1/2020 | Montrasio et al. |
| 2020/0140846 | A1 | 5/2020 | Ranum et al. |
| 2020/0206255 | A9 | 7/2020 | Ranum et al. |
| 2020/0232925 | A1 | 7/2020 | Ranum et al. |
| 2020/0241013 | A1 | 7/2020 | Ranum et al. |
| 2020/0268691 | A1 | 8/2020 | Ranum et al. |
| 2020/0341012 | A1 | 10/2020 | Ranum et al. |
| 2020/0355701 | A1 | 11/2020 | Van Meter |
| 2021/0236535 | A1 | 8/2021 | Ranum et al. |
| 2021/0285970 | A1 | 9/2021 | Ranum et al. |
| 2021/0347866 | A1 | 11/2021 | Wang et al. |
| 2022/0153874 | A1 | 5/2022 | Grimm et al. |
| 2022/0202935 | A1 | 6/2022 | Edbauer et al. |
| 2022/0373559 | A1 | 11/2022 | Ranum et al. |
| 2023/0002753 | A1 | 1/2023 | Ranum et al. |
| 2023/0218730 | A1 | 7/2023 | Ranum et al. |
| 2023/0288434 | A1 | 9/2023 | Ranum et al. |
| 2024/0069039 | A1 | 2/2024 | Ranum et al. |
| 2024/0393348 | A1 | 11/2024 | Ranum et al. |
| 2024/0426844 | A1 | 12/2024 | Ranum et al. |
| 2025/0027084 | A1 | 1/2025 | Wolin et al. |
| 2025/0041247 | A1* | 2/2025 | Ranum ................ A61K 31/155 |
| 2025/0164489 | A1 | 5/2025 | Ranum et al. |
| 2025/0177431 | A1 | 6/2025 | Richter et al. |
| 2025/0237666 | A9 | 7/2025 | Ranum et al. |

FOREIGN PATENT DOCUMENTS

| | | | |
|---|---|---|---|
| EP | 2 948 471 | A1 | 12/2015 |
| EP | 3440100 | A1 | 2/2019 |
| JP | H11-344491 | A | 12/1999 |
| JP | 2004-510162 | A | 4/2004 |
| JP | 2004-518437 | A | 6/2004 |
| JP | 2004-520803 | A | 7/2004 |
| JP | 2007-507223 | A | 3/2007 |
| JP | 2012-501193 | A | 1/2012 |
| JP | 2016-515208 | A | 5/2016 |
| JP | 2017-205118 | A | 11/2017 |
| JP | 2018-031780 | A | 3/2018 |
| JP | 2019-515894 | A | 6/2019 |
| WO | WO 2001/75067 | A2 | 10/2001 |
| WO | WO 2001/81581 | A2 | 11/2001 |
| WO | WO 2002/027317 | A2 | 4/2002 |
| WO | WO 2002/040672 | A2 | 5/2002 |
| WO | WO 2002/062945 | A2 | 8/2002 |
| WO | WO 2005/033321 | A2 | 4/2005 |
| WO | WO 2006/083800 | A2 | 8/2006 |
| WO | WO 2009/144480 | A1 | 12/2009 |
| WO | WO 2010/115033 | A2 | 10/2010 |
| WO | WO 2010/132982 | A1 | 11/2010 |
| WO | WO 2011/052906 | A2 | 5/2011 |
| WO | WO 2012/159754 | A2 | 11/2012 |
| WO | WO 2013/030588 | A1 | 3/2013 |
| WO | WO 2013/061163 | A2 | 5/2013 |
| WO | WO 2013/078375 | A2 | 5/2013 |
| WO | WO 2013/172537 | A1 | 11/2013 |
| WO | WO 2014/114303 | A1 | 7/2014 |
| WO | WO 2014/114660 | A1 | 7/2014 |
| WO | WO 2014/116865 | A1 | 7/2014 |
| WO | WO 2014/159247 | A1 | 10/2014 |
| WO | WO 2016/025692 | A1 | 2/2016 |
| WO | WO 2016/050822 | A2 | 4/2016 |
| WO | WO 2017/176813 | A1 | 10/2017 |
| WO | WO 2018/035408 | A1 | 2/2018 |
| WO | WO 2019/060918 | A1 | 3/2019 |
| WO | WO 2019/067587 | A1 | 4/2019 |
| WO | WO 2021/007110 | A1 | 1/2021 |
| WO | WO 2021/231887 | A1 | 11/2021 |

OTHER PUBLICATIONS

[No Author Listed] CRC group Top> L. K. Housing> Query, after sampling and sampling, was conducted, kept still in whole blood; CRC Corporation, Jun. 30, 2013. https://web.archive.org/web/20130630024235/http://www.crc-group.co.jp/crc/q_and_a/149.html.

Asokan et al., The AAV vector toolkit: poised at the clinical crossroads. Mol Ther. Apr. 2012;20(4):699-708. doi: 10.1038/mt.2011.287. Epub Jan. 24, 2012.

William et al., Old friends on new paths: metformin as an early phase treatment in Huntington's Disease? Medizinische Genetik, 28, pp. 215-216, Mar. 4, 2016 (Mar. 4, 2016) (Abstract).

Extended European Search Report, mailed Sep. 30, 2016, in connection with Application No. EP 14776090.4.

International Search Report and Written Opinion, mailed Aug. 22, 2014, in connection with Application No. PCT/US2014/022670.

International Preliminary Report on Patentability, mailed Sep. 24, 2015, in connection with Application No. PCT/US2014/022670.

International Search Report and Written Opinion, mailed Sep. 21, 2016, in connection with Application No. PCT/US2016/034738.

International Preliminary Report on Patentability, mailed Dec. 14, 2017, in connection with Application No. PCT/US2016/034738.

Supplementary Partial European Search Report, mailed Oct. 18, 2019, in connection with Application No. EP 17779695.0.

Extended European Search Report, mailed Jan. 7, 2020, in connection with Application No. EP 17779695.0.

International Search Report and Written Opinion, mailed Jul. 7, 2017, in connection with Application No. PCT/US2017/026020.

International Preliminary Report on Patentability, mailed Oct. 18, 2018, in connection with Application No. PCT/US2017/026020.

Extended European Search Report, mailed Dec. 17, 2020, in connection with Application No. EP 18786964.9.

International Search Report and Written Opinion, mailed Jul. 27, 2018, in connection with Application No. PCT/US2018/028015.

International Preliminary Report on Patentability, mailed Oct. 31, 2019, in connection with Application No. PCT/US2018/028015.

Extended European Search Report, mailed Nov. 26, 2021, in connection with Application No. EP 18860923.4.

International Search Report and Written Opinion, mailed Jan. 15, 2019, in connection with Application No. PCT/US2018/052913.

International Preliminary Report on Patentability, mailed Apr. 9, 2020, in connection with Application No. PCT/US2018/052913.

Extended European Search Report, mailed Jun. 11, 2021, in connection with Application No. EP 18859783.5.

International Search Report and Written Opinion, mailed Dec. 6, 2018, in connection with Application No. PCT/US2018/052745.

International Preliminary Report on Patentability, mailed Apr. 9, 2020, in connection with Application No. PCT/US2018/052745.

(56) References Cited

OTHER PUBLICATIONS

Extended European Search Report, mailed Oct. 4, 2023, in connection with application No. EP 20865149.7.
Invitation to Pay Additional Fees, mailed Nov. 30, 2020, in connection with Application No. PCT/US2020/051671.
International Search Report and Written Opinion, mailed Feb. 9, 2021, in connection with Application No. PCT/US2020/051671.
International Preliminary Report on Patentability, mailed Mar. 31, 2022, in connection with Application No. PCT/US2020/051671.
Extended European Search Report, mailed Aug. 25, 2023, in connection with Application No. EP 20869039.6.
International Search Report and Written Opinion, mailed Dec. 31, 2020, in connection with Application No. PCT/US2020/051670.
International Preliminary Report on Patentability, mailed Apr. 7, 2022, in connection with Application No. PCT/US2020/051670.
Extended European Search Report, mailed Oct. 4, 2023, in connection with application No. EP 20874343.5.
Invitation to Pay Additional Fees, mailed Feb. 19, 2021, in connection with Application No. PCT/US2020/054976.
International Search Report and Written Opinion, mailed Apr. 23, 2021, in connection with Application No. PCT/US2020/054976.
International Preliminary Report on Patentability, mailed Apr. 21, 2022, in connection with Application No. PCT/US2020/054976.
Invitation to Pay Additional Fees, mailed Mar. 30, 2023, in connection with Application No. PCT/US2022/051530.
International Search Report and Written Opinion, mailed May 25, 2023, in connection with Application No. PCT/US2022/051530.
International Search Report and Written Opinion, mailed Jul. 19, 2023, in connection with Application No. PCT/US2023/063328.
[No Author Listed] Amersham ECL Western Blotting Detection Reagent. Retrieved from the internet under https://www.cytivalifesciences.com/en/us/shop/protein-analysis/blotting-and-detection/blotting-standards-and-reagents/amersham-ecl-western-blotting-detection-reagent-p-05748 on Feb. 22, 2022, 6 pages.
[No Author Listed] EBNA1—Epstein-Barr nuclear antigen 1—Epstein-Barr virus (strain GD1) (HHV-4)—EBNA1 gene & protein, Jan. 2018. 2018. Retrieved from the internet under https://www.uniprot.org/uniprot/Q3KSS4 on Sep. 12, 2018. 6 pages.
[No Author Listed], Abstracts. Medizinische Genetik, Berufsverband Nedizinische Genetik, Muchen, DE. Medgen. Mar. 4, 2016; 28(1):84-232. DOI: 10.1007/s11825-016-0083-5.
Ash et al., Unconventional translation of C9ORF72 GGGGCC expansion generates insoluble polypeptides specific to c9FTD/ALS. Neuron. Feb. 20, 2013;77(4):639-46. doi: 10.1016/j.neuron.2013.02.004. Epub Feb. 12, 2013.
Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.
Ayhan et al., SCA8 RAN polySer protein preferentially accumulates in white matter regions and is regulated by eIF3F. EMBO J. Oct. 1, 2018;37(19). pii: e99023. doi: 10.15252/embj.201899023. Epub Sep. 11, 2018.
Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.
Bae et al., Antibody-aided clearance of extracellular α-synuclein prevents cell-to-cell aggregate transmission. J Neurosci. Sep. 26, 2012;32(39):13454-69.
Barzilai et al., Metformin as a Tool to Target Aging. Cell Metab. Jun. 14, 2016;23(6):1060-1065. doi: 10.1016/j.cmet.2016.05.011.
Batra et al., Partners in crime: bidirectional transcription in unstable microsatellite disease. Hum Mol Genet. Apr. 15, 2010;19(R1):R77-82. doi: 10.1093/hmg/ddq132. Epub Apr. 4, 2010.
Bañez-Coronel et al., A pathogenic mechanism in Huntington's disease involves small CAG-repeated RNAs with neurotoxic activity. PLoS Genet. 2012;8(2):e1002481. doi: 10.1371/journal.pgen.1002481. Epub Feb. 23, 2012.
Bañez-Coronel et al., RAN Translation in Huntington Disease. Neuron. Nov. 18, 2015888(4):667-77. doi: 10.1016/j.neuron.2015.10.038.
Bañez-Coronel et al., Repeat-associated non-AUG (RAN) translation: insights from pathology. Lab Invest. Jul. 2019;99(7):929-942. doi: 10.1038/s41374-019-0241-x. Epub Mar. 27, 2019.
Bañez-Coronel et al., Sense and antisense RAN proteins in the CAG•CTG polyglutamine spinocerebellar ataxias. International Congress for Ataxia Research. Abstract ID 271. Nov. 1-4, 2022. 1 page.
Benkirane et al., Oncogenic potential of TAR RNA binding protein TRBP and its regulatory interaction with RNA-dependent protein kinase PKR. EMBO J. Feb. 3, 1997;16(3):611-24. doi: 10.1093/emboj/16.3.611.
Brooks et al., Spinal and bulbar muscular atrophy: a trinucleotide-repeat expansion neurodegenerative disease. Trends Neurosci. Oct. 1995;18(10):459-61. doi: 10.1016/0166-2236(95)94497-s.
Carroll et al., Potent and selective antisense oligonucleotides targeting single-nucleotide polymorphisms in the Huntington disease gene / allele-specific silencing of mutant huntingtin. Mol Ther. Dec. 2011;19(12):2178-85. doi: 10.1038/mt.2011.201. Epub Oct. 4, 2011.
Chen et al., Antidiabetic drug metformin (Glucophage$^R$) increases biogenesis of Alzheimer's amyloid peptides via up-regulating BACE1 transcription. Proc Natl Acad Sci U S A. Mar. 10, 2009;106(10):3907-12. doi: 10.1073/pnas.0807991106. Epub Feb. 23, 2009.
Chen et al., Functional genomics in *Drosophila* models of human disease. Briefings in Functional Genomics. Aug. 22, 2012;11(5):405-415.
Cheng et al., C9ORF72 GGGGCC repeat-associated non-AUG translation is upregulated by stress through eIF2α phosphorylation. Nat Commun. Jan. 4, 2018;9(1):51. doi: 10.1038/s41467-017-02495-z.
Cleary et al., New developments in RAN translation: insights from multiple diseases. Curr Opin Genet Dev. Jun. 2017;44:125-134. doi: 10.1016/j.gde.2017.03.006. Epub Mar. 30, 2017. Author Manuscript, 18 pages.
Cleary et al., Repeat associated non-ATG (RAN) translation: new starts in microsatellite expansion disorders. Curr Opin Genet Dev. Jun. 2014;26:6-15. doi: 10.1016/j.gde.2014.03.002. Epub May 22, 2014. Author Manuscript, 20 pages.
Cleary et al., Repeat-associated non-ATG (RAN) translation in neurological disease. Hum Mol Genet. Oct. 15, 2013;22(R1):R45-51. doi: 10.1093/hmg/ddt371. Epub Aug. 4, 2013.
Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015.
Duan et al., Generation of polyclonal antiserum for the detection of methylarginine proteins. J Immunol Methods. Mar. 30, 2007;320(1-2):132-42. Epub Feb. 6, 2007.
Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 26, 2009.
Foretz et al., Metformin: from mechanisms of action to therapies. Cell Metab. Dec. 2, 2014;20(6):953-66. doi: 10.1016/j.cmet.2014.09.018. Epub Oct. 30, 2014.
Gantois et al., Metformin ameliorates core deficits in a mouse model of fragile X syndrome. Nat Med. Jun. 2017;23(6):674-677. doi: 10.1038/nm.4335. Epub May 15, 2017.
Gkogkas et al., Pharmacogenetic inhibition of eIF4E-dependent Mmp9 mRNA translation reverses fragile X syndrome-like phenotypes. Cell Rep. Dec. 11, 2014;9(5):1742-1755. doi: 10.1016/j.celrep.2014.10.064. Epub Nov. 26, 2014.
Green et al., RAN translation at C9orf72-associated repeat expansions is selectively enhanced by the integrated stress response. Nat Commun. Dec. 8, 2017;8(1):2005. doi: 10.1038/s41467-017-02200-0.
GÓMez-tortosa et al., C9ORF72 hexanucleotide expansions of 20-22 repeats are associated with frontotemporal deterioration. Neurology. Jan. 22, 2013;80(4):366-70. doi: 10.1212/WNL.0b013e31827f08ea. Epub Jan. 2, 2013.
Hock et al., Antibodies against beta-amyloid slow cognitive decline in Alzheimer's disease. Neuron. May 22, 2003;38(4):547-54.

(56) References Cited

OTHER PUBLICATIONS

Jawaid et al., ALS disease onset may occur later in patients with pre-morbid diabetes mellitus. Eur J Neurol. May 2010;17(5):733-9. doi: 10.1111/j.1468-1331.2009.02923.x. Epub Jan. 13, 2010.
Jin et al., Metformin Protects Cells from Mutant Huntingtin Toxicity Through Activation of AMPK and Modulation of Mitochondrial Dynamics. Neuromolecular Med. Dec. 2016;18(4):581-592. doi: 10.1007/s12017-016-8412-z. Epub May 25, 2016. Author Manuscript, 19 pages.
Kearse et al., CGG Repeat-Associated Non-AUG Translation Utilizes a Cap-Dependent Scanning Mechanism of Initiation to Produce Toxic Proteins. Mol Cell. Apr. 21, 2016;62(2):314-322. doi: 10.1016/j.molcel.2016.02.034. Epub Mar. 31, 2016.
Kioumourtzoglou et al., Diabetes Mellitus, Obesity, and Diagnosis of Amyotrophic Lateral Sclerosis: A Population-Based Study. JAMA Neurol. Aug. 2015;72(8):905-11. doi: 10.1001/jamaneurol.2015.0910. Author Manuscript, 15 pages.
Koide et al., Unstable expansion of CAG repeat in hereditary dentatorubral-pallidoluysian atrophy (DRPLA). Nat Genet. Jan. 1994;6(1):9-13. doi: 10.1038/ng0194-9.
Koob et al., An untranslated CTG expansion causes a novel form of spinocerebellar ataxia (SCA8). Nat Genet. Apr. 1999;21(4):379-84. doi: 10.1038/7710.
Leitman et al., ER stress-induced eIF2-alpha phosphorylation underlies sensitivity of striatal neurons to pathogenic huntingtin. PLoS One. Mar. 3, 2014;9(3):e90803. doi: 10.1371/journal.pone.0090803.
Liu et al., C9orf72 BAC Mouse Model with Motor Deficits and Neurodegenerative Features of ALS/FTD. Neuron. May 4, 2016;90(3):521-34. doi: 10.1016/j.neuron.2016.04.005. Epub Apr. 21, 2016.
Ma et al., Metformin therapy in a transgenic mouse model of Huntington's disease. Neurosci Lett. Jan. 10, 2007;411(2):98-103. doi: 10.1016/j.neulet.2006.10.039. Epub Nov. 15, 2006.
Memmott et al., Metformin prevents tobacco carcinogen—induced lung tumorigenesis. Cancer Prev Res (Phila). Sep. 2010;3(9):1066-76. doi: 10.1158/1940-6207.CAPR-10-0055. Epub Sep. 1, 2010.
Mirkin, Expandable DNA repeats and human disease. Nature. Jun. 21, 2007;447(7147):932-40. doi: 10.1038/nature05977.
Moon et al., Neuronal Regulation of eIF2α Function in Health and Neurological Disorders. Trends Mol Med. Jun. 2018;24(6):575-589. doi: 10.1016/j.molmed.2018.04.001. Epub Apr. 30, 2018.
Mori et al., The C9orf72 GGGGCC repeat is translated into aggregating dipeptide-repeat proteins in FTLD/ALS. Science. Mar. 15, 2013;339(6125):1335-8. doi: 10.1126/science.1232927. Epub Feb. 7, 2013. Supplementary information included.
Nguyen et al., Repeat-Associated Non-ATG Translation: Molecular Mechanisms and Contribution to Neurological Disease. Annu Rev Neurosci. Jul. 8, 2019;42:227-247. doi: 10.1146/annurev-neuro-070918-050405. Epub Mar. 25, 2019. Author Manuscript, 24 pages.
Pakos-Zebrucka et al., The integrated stress response. EMBO Rep. Oct. 2016;17(10):1374-1395. doi: 10.15252/embr.201642195. Epub Sep. 14, 2016.
Park et al., TAR RNA-binding protein is an inhibitor of the interferon-induced protein kinase PKR. Proc Natl Acad Sci U S A. May 24, 1994;91(11):4713-7. doi: 10.1073/pnas.91.11.4713.
Perez et al., CCG•CGG interruptions in high-penetrance SCA8 families increase RAN translation and protein toxicity. EMBO Mol Med. Nov. 8, 2021;13(11):e14095. doi: 10.15252/emmm.202114095. Epub Oct. 11, 2021.
Satoh et al., Dystrophic neurites express C9orf72 in Alzheimer's disease brains. Alzheimers Res Ther. Aug. 16, 2012;4(4):33. doi: 10.1186/alzrt136. 13 pages.
Sha et al., Treatment implications of C9ORF72. Alzheimer's Res Ther. Nov. 27, 2012;4(6):46. doi: 10.1186/alzrt149. eCollection 2012.
Shoesmith et al., Amyotrophic lateral sclerosis: update for family physicians. Can Fam Physician. Dec. 2006;52(12):1563-9.
Sonenberg et al., Regulation of translation initiation in eukaryotes: mechanisms and biological targets. Cell. Feb. 20, 2009;136(4):731-45. doi: 10.1016/j.cell.2009.01.042.
Soragni et al., Repeat-Associated Non-ATG (RAN) Translation in Fuchs' Endothelial Corneal Dystrophy. Invest Ophthalmol Vis Sci. Apr. 1, 2018;59(5):1888-1896. doi: 10.1167/iovs.17-23265.
Taylor et al., Decoding ALS: from genes to mechanism. Nature. Nov. 10, 2016;539(7628):197-206. doi: 10.1038/nature20413. Author Manuscript, 28 pages.
Tian et al., Expanded CUG repeat RNAs form hairpins that activate the double-stranded RNA-dependent protein kinase PKR. RNA. Jan. 2000;6(1):79-87. doi: 10.1017/s1355838200991544.
Todd et al., CGG repeat-associated translation mediates neurodegeneration in fragile X tremor ataxia syndrome. Neuron. May 8, 2013;78(3):440-55. doi: 10.1016/j.neuron.2013.03.026. Epub Apr. 18, 2013. Erratum in: Neuron. Jul. 24, 2013;79(2):402.
Todd et al., Insights into the pathogenic mechanisms of Chromosome 9 open reading frame 72 (C9orf72) repeat expansions. J Neurochem. Aug. 2016;138 Suppl 1:145-62. doi: 10.1111/jnc.13623. Epub Jun. 15, 2016.
Trouth et al., Myasthenia gravis: a review. Autoimmune Dis. 2012;874680. doi: 10.1155/2012/874680. Epub Oct. 31, 2012.
Tsuji, S., Dentatorubral-pallidoluysian atrophy. Handb Clin Neurol. 2012; 103:587-94. doi: 10.1016/B978-0-444-51892-7.00041-3.
Vaughn et al., Inhibition of PKR protects against tunicamycin-induced apoptosis in neuroblastoma cells. Gene. Feb. 15, 2014;536(1):90-6. doi: 10.1016/j.gene.2013.11.074. Epub Dec. 14, 2013.
Vishwakarma et al., Current molecular insight to reveal the dynamics of CAG repeating units in spinocerebellar ataxia. Intractable Rare Dis Res. May 2018;7(2):79-86. doi: 10.5582/irdr.2018.01039.
Wang et al., Comparative Analysis of VOCs in Exhaled Breath of Amyotrophic Lateral Sclerosis and Cervical Spondylotic Myelopathy Patients. Sci Rep. 2016;6:26120. Published May 23, 2016. doi:10.1038/srep26120.
Welnowska et al., Translation of viral mRNA without active eIF2: the case of picornaviruses. PLoS One. 2011;6(7):e22230. doi: 10.1371/journal.pone.0022230. Epub Jul. 14, 2011.
Wieben et al., Amplification-free long-read sequencing of TCF4 expanded trinucleotide repeats in Fuchs Endothelial Corneal Dystrophy. PLoS One. Jul. 5, 2019;14(7):e0219446. doi: 10.1371/journal.pone.0219446.
Wojciechowska et al., RAN translation and frameshifting as translational challenges at simple repeats of human neurodegenerative disorders. Nucleic Acids Res. Oct. 29, 2014;42(19):11849-64. doi: 10.1093/nar/gku794. Epub Sep. 12, 2014.
Xiao et al., Isoform-specific antibodies reveal distinct subcellular localizations of C9orf72 in amyotrophic lateral sclerosis. Ann Neurol. Oct. 2015;78(4):568-83. doi: 10.1002/ana.24469. Epub Aug. 29, 2015.
Yanagisawa et al., Protein Binding of a DRPLA Family Through Arginine-Glutamic Acid Dipeptide repeats is Enhanced by Extended polyglutamine. Human Molecular Genetics. 2000;9(9):1433-1442.
Yu et al., Developing therapeutic antibodies for neurodegenerative disease. Neurotherapeutics. Jul. 2013;10(3):459-72. doi: 10.1007/s13311-013-0187-4.
Zhang et al., Aggregation-prone c9FTD/ALS poly(GA) RAN-translated proteins cause neurotoxicity by inducing ER stress. Acta Neuropathol. 2014;128:505-24.
Zhou et al., Antibodies inhibit transmission and aggregation of C9orf72 poly-GA dipeptide repeat proteins. EMBO Mol Med. May 2017;9(5):687-702. doi: 10.15252/emmm.201607054.
Zhu et al., Suppression of PKR promotes network excitability and enhanced cognition by interferon-γ-mediated disinhibition. Cell. Dec. 9, 2011;147(6):1384-96. doi: 10.1016/j.cell.2011.11.029.
Zu et al., Metformin inhibits RAN translation through PKR pathway and mitigates disease in C9orf72 ALS/FTD mice. Proc Natl Acad Sci U S A. Aug. 4, 2020;117(31):18591-18599. doi: 10.1073/pnas.2005748117. Epub Jul. 20, 2020. Supplementary Materials, 33 pages.
Zu et al., Non-ATG-initiated translation directed by microsatellite expansions. Proc Natl Acad Sci U S A. Jan. 4, 2011;108(1):260-5. doi: 10.1073/pnas.1013343108. Epub Dec. 20, 2010.

(56) References Cited

OTHER PUBLICATIONS

Zu et al., RAN proteins and RNA foci from antisense transcripts in C9ORF72 ALS and frontotemporal dementia. Proc Natl Acad Sci U S A. Dec. 17, 2013;110(51):E4968-77. doi: 10.1073/pnas.1315438110. Epub Nov. 18, 2013.
Zu et al., RAN Translation Regulated by Muscleblind Proteins in Myotonic Dystrophy Type 2. Neuron. Sep. 13, 2017;95(6):1292-1305.e5. doi: 10.1016/j.neuron.2017.08.039.
Gendron et al., Cerebellar c9RAN proteins associate with clinical and neuropathological characteristics of C9ORF72 repeat expansion carriers. Acta Neuropathol. Oct. 2015;130(4):559-73. doi: 10.1007/s00401-015-1474-4. Epub Sep. 8, 2015.
Gendron et al., Poly(GP) proteins are a useful pharmacodynamic marker for C9ORF72-associated amyotrophic lateral sclerosis. Sci Transl Med. Mar. 29, 2017;9(383):eaai7866. doi: 10.1126/scitranslmed.aai7866.
Alaoui-Ismaili et al., Design of second generation therapeutic recombinant bone morphogenetic proteins. Cytokine Growth Factor Rev. Oct.-Dec. 2009;20(5-6):501-7. doi: 10.1016/j.cytogfr.2009.10.001. Epub Nov. 11, 2009.
Anger, Animal test systems to study behavioral dysfunctions of neurodegenerative disorders. Neurotoxicology. 1991 Fall;12(3):403-13.
Atwood et al., A Unified Hypothesis of Early- and Late-Onset Alzheimer's Disease Pathogenesis. J Alzheimers Dis. 2015;47(1):33-47. doi: 10.3233/JAD-143210.
Banez Coronel et al., Repeat associated non-AUG translation as a common mechanism for the polyGln ataxias. bioRxiv. Oct. 15, 2025. doi: https://doi.org/10.1101/2025.10.14.682372. 44 pages.
Bruijn et al., Unraveling the mechanisms involved in motor neuron degeneration in ALS. Annu Rev Neurosci. 2004;27:723-49. doi: 10.1146/annurev.neuro.27.070203.144244.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38. doi: 10.1083/jcb.111.5.2129.
Guo et al., Protein tolerance to random amino acid change. Proc Natl Acad Sci U S A. Jun. 22, 2004;101(25):9205-10. doi: 10.1073/pnas.0403255101. Epub Jun. 14, 2004.
Guo et al., RAN proteins in neurodegenerative disease: Repeating themes and unifying therapeutic strategies. Curr Opin Neurobiol. Feb. 2022;72:160-170. doi: 10.1016/j.conb.2021.11.001. Epub Dec. 22, 2021.
Henstridge et al., Beyond the neuron-cellular interactions early in Alzheimer disease pathogenesis. Nat Rev Neurosci. Feb. 2019;20(2):94-108. doi: 10.1038/s41583-018-0113-1.
Holmes et al., Expansion of a novel CAG trinucleotide repeat in the 5' region of PPP2R2B is associated with SCA12. Nat Genet. Dec. 1999;23(4):391-2. doi: 10.1038/70493.
Ju et al., A yeast model of FUS/TLS-dependent cytotoxicity. PLoS Biol. Apr. 2011;9(4):e1001052. doi: 10.1371/journal.pbio.1001052. Epub Apr. 26, 2011.
Lagier-Tourenne et al., TDP-43 and FUS/TLS: emerging roles in RNA processing and neurodegeneration. Hum Mol Genet. Apr. 15, 2010;19(R1):R46-64. doi: 10.1093/hmg/ddq137. Epub Apr. 15, 2010.
Murase et al., Drug Discovery Research Toward the Small Molecular Therapeutic Agents for Repeat Expansion Diseases, Nagasaki International University Review, Mar. 2022, vol. 22, pp. 177-185.
Pawson et al., Assembly of cell regulatory systems through protein interaction domains. Science. Apr. 18, 2003;300(5618):445-52. doi: 10.1126/science.1083653.
Ranganathan et al., Multifaceted Genes in Amyotrophic Lateral Sclerosis-Frontotemporal Dementia. Front Neurosci. Jul. 7, 2020;14:684. doi: 10.3389/fnins.2020.00684.
Romano et al., Metformin decreases RAN proteins, rescues splicing abnormalities and improves behavioral phenotypes in SCA8 BAC mice. bioRxiv. Aug. 25, 2025. doi: https://doi.org/10.1101/2025.08.21.671563. 38 pages.
Rothstein, Therapeutic horizons for amyotrophic lateral sclerosis. Curr Opin Neurobiol. Oct. 1996;6(5):679-87. doi: 10.1016/s0959-4388(96)80103-6.
Sarter, Animal cognition: defining the issues. Neurosci Biobehav Rev. Nov. 2004;28(7):645-50. doi: 10.1016/j.neubiorev.2004.09.005.
Sato et al., Spinocerebellar ataxia type 31 is associated with "inserted" penta-nucleotide repeats containing (TGGAA)n. Am J Hum Genet. Nov. 2009;85(5):544-57. doi: 10.1016/j.ajhg.2009.09.019. Epub Oct. 29, 2009.
Swerdlow, Pathogenesis of Alzheimer's disease. Clin Interv Aging. 2007;2(3):347-59.
Tayebati, Animal models of cognitive dysfunction. Mech Ageing Dev. Feb. 2006;127(2):100-8. doi: 10.1016/j.mad.2005.09.026. Epub Nov. 15, 2005.
Williams et al., CCNF mutations in amyotrophic lateral sclerosis and frontotemporal dementia. Nat Commun. Apr. 15, 2016;7:11253. doi: 10.1038/ncomms11253.

* cited by examiner

SEQUENCE LISTING

```
Sequence total quantity: 4
SEQ ID NO: 1            moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 1
AAAAAAAAAA AAAAAAAAAA                                                20

SEQ ID NO: 2            moltype = AA  length = 18
FEATURE                 Location/Qualifiers
REGION                  1..18
                        note = Synthetic polypeptide
source                  1..18
                        mol_type = protein
                        organism = synthetic construct
SEQUENCE: 2
LLLLLLLLLL LLLLLLLL                                                  18

SEQ ID NO: 3            moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 3
SSSSSSSSSS SSSSSSSSSS                                                20

SEQ ID NO: 4            moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 4
CCCCCCCCCC CCCCCCCCCC                                                20
```

USE OF METFORMIN AND ANALOGS THEREOF TO REDUCE RAN PROTEIN LEVELS IN THE TREATMENT OF NEUROLOGICAL DISORDERS

RELATED APPLICATIONS

This application is a continuation of and claims priority under 35 U.S.C. § 120 to U.S. patent application Ser. No. 16/650,721, filed Mar. 25, 2020, which is a national stage filing under 35 U.S.C. § 371 of International PCT Application, PCT/US2018/052913, filed Sep. 26, 2018, which claims priority under 35 U.S.C. § 119 (e) to U.S. Provisional Application, U.S. Ser. No. 62/563,588, filed Sep. 26, 2017, each of which is incorporated herein by reference.

REFERENCE TO AN ELECTRONIC SEQUENCE LISTING

The contents of the electronic sequence listing (U120270066US02-SEQ-DCS.xml; Size: 6,137 bytes; and Date of Creation: Jan. 3, 2024) is herein incorporated by reference in its entirety.

GOVERNMENT SUPPORT

This invention was made with government support under grant numbers NS040389, NS058901, and NS098819 awarded by the National Institutes of Health. The government has certain rights in the invention.

BACKGROUND OF THE INVENTION

Mutations of certain repeat expansions (e.g., CAGG, CCTG, GGGGCC, GGCCCC, CAG, and CTG) are associated with a number of different neurological diseases (e.g., C9ORFf72 amyotrophic lateral sclerosis (ALS), or C9ORFf72 frontotemporal dementia; myotonic dystrophy type 1 (DM1) and myotonic dystrophy type 2 (DM2); spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease (HD); Fragile X Tremor Ataxia Syndrome (FXTAS)); Fuch's endothelial corneal dystrophy (FECD); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; and Fragile XE syndrome (FRAXE). In a growing number of these diseases including, but not limited to, C9ORF72 ALS or C9ORF72 FTD, FXTAS, HD, SCA8, DM1 and DM2, expansion mutations have been shown to undergo a novel type of protein translation that occurs in multiple reading frames and does not require a canonical AUG initiation codon (Zu et al. 2011; Ash et al. 2013; Mori et al. 2013; Todd et al. 2013; Zu et al. 2013; Banez-Coronel et al. 2015; Cleary and Ranum 2017; Zu et al. 2017). This type of translation, was first described by Zu et al., (Zu et al. 2011) (PNAS 2011 108:260-265) is called repeat associated non-ATG (RAN) translation and the proteins that are produced are called RAN proteins. There is growing evidence that RAN proteins are toxic and contribute to a growing number of diseases (Cleary and Ranum 2017). It therefore is important to develop therapeutic strategies that reduce the level of repeat associated non-ATG (RAN) proteins to treat neurological diseases caused by repeat expansion mutations.

SUMMARY OF THE INVENTION

Described herein are compositions and methods for the treatment of neurological diseases associated with repeat associated non-ATG (RAN) proteins. In some aspects, the disclosure also relates to the recognition that inhibiting Protein Kinase R (PKR) expression or activity inhibits RAN protein translation. The disclosure is based, in part, on the discovery that mutations of repeat expansions (e.g., CAGG, CCTG, GGGGCC, GGCCCC, CAG, and CTG) are associated with a number of different neurological diseases (e.g., C9ORFf72 amyotrophic lateral sclerosis (ALS) or C9ORFf72 frontotemporal dementia; myotonic dystrophy type 1 (DM1) and myotonic dystrophy type 2 (DM2); spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease (HD); Fuch's endothelial corneal dystrophy (FECD); Fragile X Tremor Ataxia Syndrome (FXTAS); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; and Fragile XE syndrome (FRAXE)). In particular, four repeat associated non-ATG translation proteins (also referred to as RAN proteins)—polyalanine, polyserine, polyleucine, and polycysteine (polyAla, polySer, polyLeu and polyCys, respectively)—accumulate in the brains, tissue (e.g., blood, cerebrospinal fluid), and central nervous systems of subjects having Huntington's disease (HD). In C9ORF72 ALS or C9ORF72 FTD RAN proteins with dipeptide RAN proteins (e.g., polyGlyPro (GP), polyGlyAla (GA), polyGlyArg (GR), polyProAla (PA)) have been shown to accumulate in patient brains, blood and other tissues. Similarly, homopolymeric and tetrapeptide RAN proteins have been found in patients with Fragile X Tremor Ataxia Syndrome (FXTAS), myotonic dystrophy type 1 (DM1) and myotonic dystrophy type 2 (DM2). Based on results from Zu et al., PNAS 2011, RAN proteins are also predicted to accumulate in patients with diseases caused by CAG•CTG repeat expansions including but not limited to spinocerebellar ataxia types 1, 2, 3, 6, 7, 8, 10, 12, 17, 31, and 36; spinal bulbar muscular atrophy (SBMA); dentatorubral-pallidoluysian atrophy (DRPLA); and Fuch's corneal endothelial dystrophy. RAN proteins can be detected in a biological sample (e.g., blood, serum, tissue, or cerebrospinal fluid (CSF)) from a subject having or at risk of developing HD, C9ORF72 ALS, C9ORF72 FTD, DM1, DM2, FXTAS, SCA8; Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; and Fragile XE syndrome (FRAXE); or other diseases caused by microsatellite repeat expansion mutations.

In one aspect, the present invention provides methods for treating and/or preventing a neurological disease associated with repeat expansions in a subject, the method comprising administering to the subject a therapeutically effective amount of a compound of Formula (I):

(I)

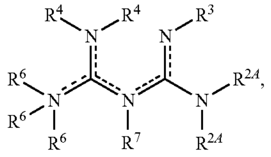

or a pharmaceutically acceptable salt, co-crystal, tautomer, stereoisomer, solvate, hydrate, polymorph, isotopically enriched derivative, or prodrug thereof, wherein $R^{2A}$, $R^3$, $R^4$, $R^6$, and $R^7$ are as defined herein.
Exemplary compounds of Formula (I) include, but are not limited to:
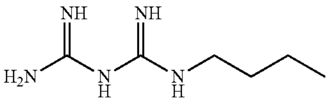,
(buformin)
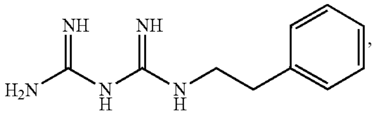,
(phenformin)
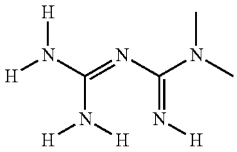
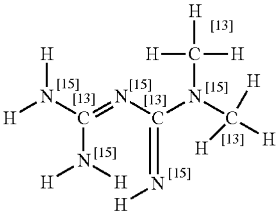
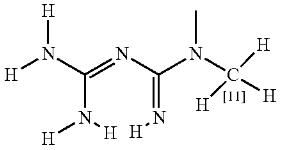
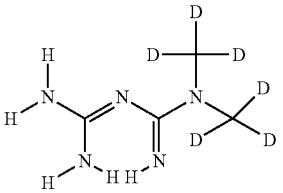
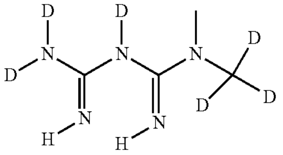
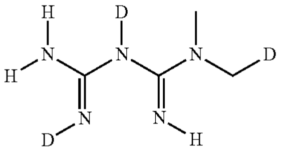
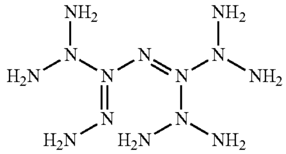
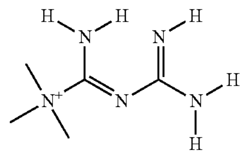
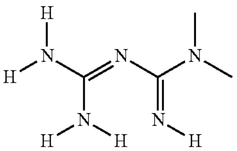
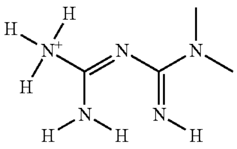
-continued
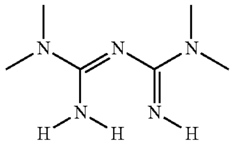
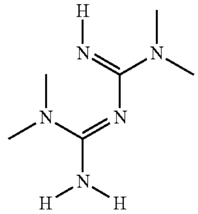
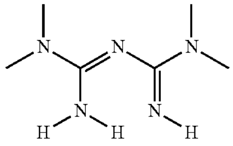
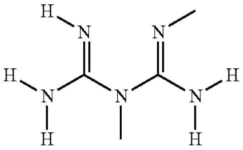
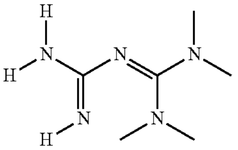
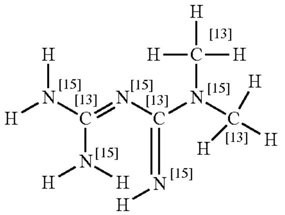
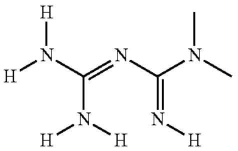
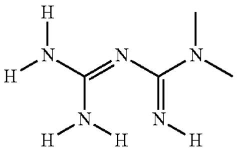
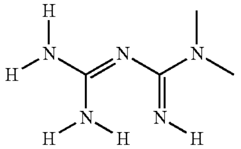
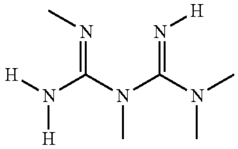
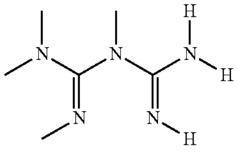
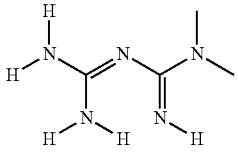
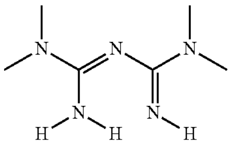
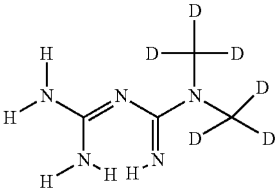
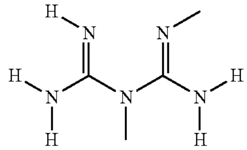
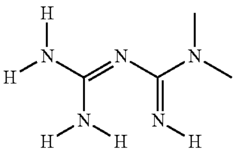
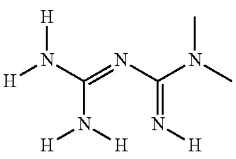
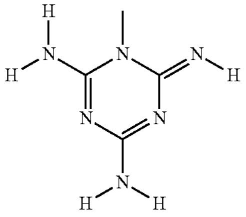
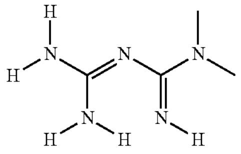
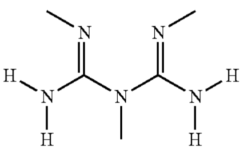

-continued

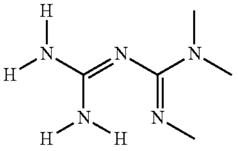

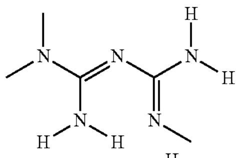

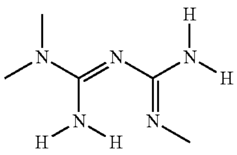

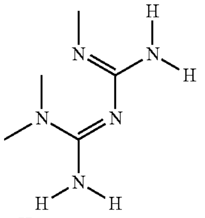

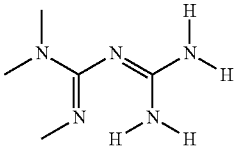

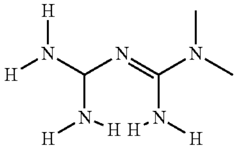

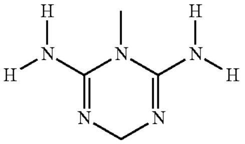

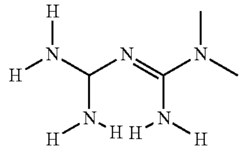

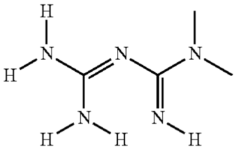

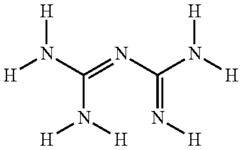

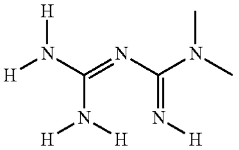

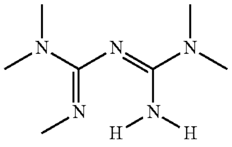

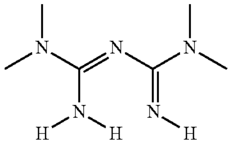

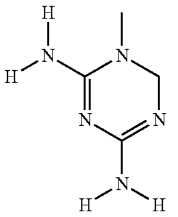

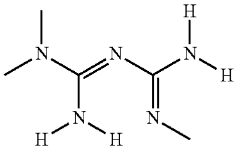

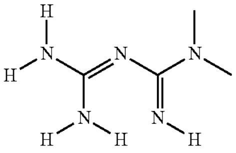

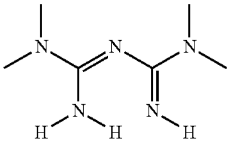

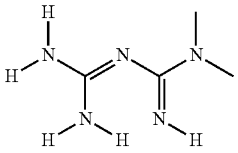

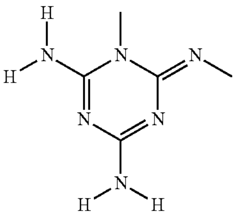

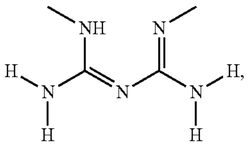

and pharmaceutically acceptable salts, solvates, hydrates, polymorphs, co-crystals, tautomers, stereoisomers, isotopically labeled derivatives, and prodrugs thereof.

In one aspect, the present invention provides methods for treating and/or preventing a neurological disease associated with repeat expansions in a subject, the method comprising administering to the subject a therapeutically effective amount of metformin:

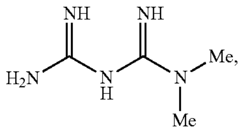

or a pharmaceutically acceptable salt, solvate, hydrate, tautomer, stereoisomer, derivative, or prodrug thereof.

In another aspect, the present invention provides methods for treating and/or preventing a neurological disease associated with repeat expansions in a subject, the method comprising administering to the subject a therapeutically effective amount of a compound of Formula (II):

(II)

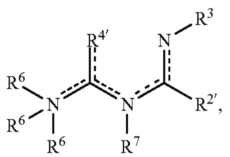

or a pharmaceutically acceptable salt, co-crystal, tautomer, stereoisomer, solvate, hydrate, polymorph, isotopically enriched derivative, or prodrug thereof, wherein $R^{2'}$, $R^3$, $R^{4'}$, $R^6$, and $R^7$ are as defined herein.

Exemplary compounds of Formula (II) include, but are not limited to:

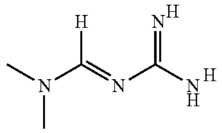

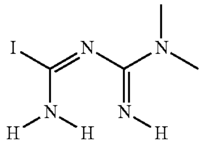

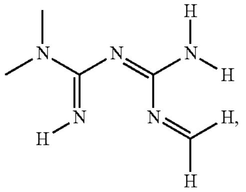

and pharmaceutically acceptable salts, solvates, hydrates, polymorphs, co-crystals, tautomers, stereoisomers, isotopically labeled derivatives, and prodrugs thereof.

In another aspect, the present invention provides methods for treating and/or preventing a neurological disease associated with repeat expansions in a subject, the method comprising administering to the subject a therapeutically effective amount of a compound of Formula (III), (III-A), or (III-B):

(III)

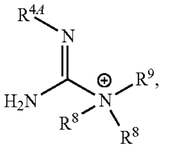

or (III-A)

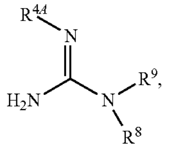

(III-B)

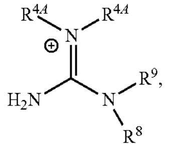

or a pharmaceutically acceptable salt, co-crystal, tautomer, stereoisomer, solvate, hydrate, polymorph, isotopically enriched derivative, or prodrug thereof, wherein $R^{4A}$, $R^8$, and $R^9$ are as defined herein.

Exemplary compounds of Formulae (III), (III-A), and (III-B) include, but are not limited to:

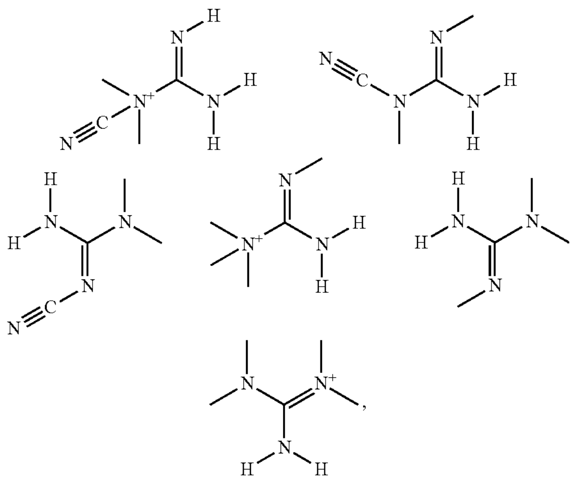

and pharmaceutically acceptable salts, solvates, hydrates, polymorphs, co-crystals, tautomers, stereoisomers, isotopically labeled derivatives, and prodrugs thereof.

Another aspect of the invention relates to methods of reducing the accumulation of repeat associated non-ATG protein (RAN) in a subject, tissue, or cell, the method comprising administering to the subject, or contacting the biological sample (e.g., tissue or cells) with an effective amount of a compound of Formula (I), (II), (III), (III-A), or (III-B) (e.g., metformin), or a pharmaceutically acceptable salt, solvate, hydrate, tautomer, stereoisomer, derivative, or prodrug thereof, or a pharmaceutical composition thereof. The present invention also provides uses of a compound of Formula (I), (II), (III), (III-A), or (III-B) (e.g., metformin), or a pharmaceutically acceptable salt, solvate, hydrate, tautomer, stereoisomer, derivative, or prodrug thereof, to treat and/or prevent a neurological disease associated with repeat expansions in a subject in need thereof.

Another aspect of the present disclosure relates to kits comprising a container with a compound of Formula (I), (II), (III), (III-A), or (III-B) (e.g., metformin), a pharmaceutically acceptable salt, solvate, hydrate, tautomer, stereoisomer, derivative, or prodrug, or a pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3rd Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastercomer, or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example, "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^AH(C^BH_2C^CH_3)$— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, $CH(C_2H_5)$— is a $C_1$ hydrocarbon chain, and

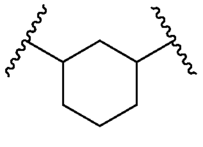 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —$(CH_2)_4$—). A hydrocarbon chain may also be unsaturated and include one or more C═C and/or C≡C bonds anywhere in the hydrocarbon chain. For instance, —CH═CH—$(CH_2)_2$—, —$CH_2$—C≡C—$CH_2$—, and —C≡C—CH═CH— are all examples of a unsubstituted and unsaturated hydrocarbon chain. In certain embodiments, the hydrocarbon chain is unsubstituted (e.g., —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

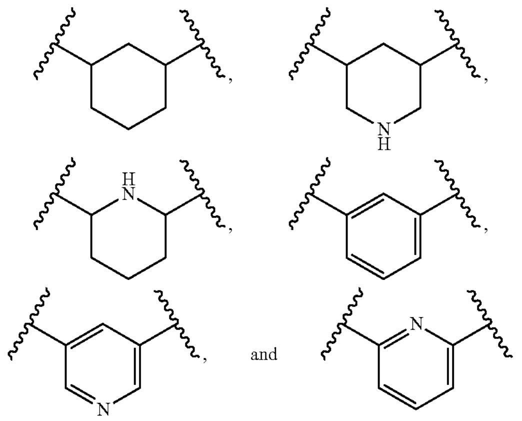

are all examples of a hydrocarbon chain. In contrast, in certain embodiments

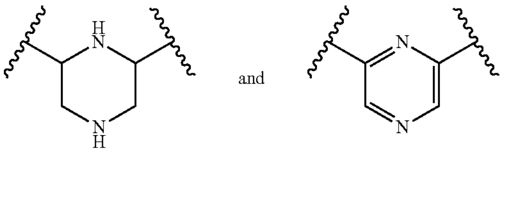 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_2$ g alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and $_{ww}$ero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from the group consisting of nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from the group consisting of nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from the group consisting of nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from the group consisting of nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4 membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from the group consisting of nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation but is not intended to include aromatic groups (e.g., aryl or heteroaryl groups) as defined herein. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix-ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3^+X^-$, $—N(OR^{cc})R^{bb}$, —SH, $—SR^{aa}$, $—SSR^{cc}$, $—C(=O)R^{aa}$, $—CO_2H$, —CHO, $—C(OR^{cc})_2$, $—CO_2R^{aa}$, $—OC(=O)R^{aa}$, $—OCO_2R^{aa}$, $—C(=O)N(R^{bb})_2$, $—OC(=O)N(R^{bb})_2$, $—NR^{bb}C(=O)R^{aa}$, $—NR^{bb}CO_2R^{aa}$, $—NR^{bb}C(=O)N(R^{bb})_2$, $—C(=NR^{bb})R^{aa}$, $—C(=NR^{bb})OR^{aa}$, $—OC(=NR^{bb})R^{aa}$, $—OC(=NR^{bb})OR^{aa}$, $—C(=NR^{bb})N(R^{bb})_2$, $—OC(=NR^{bb})N(R^{bb})_2$, $—NR^{bb}C(=NR^{bb})N(R^{bb})_2$, $—C(=O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(=O)R^{aa}$, $—OS(=O)R^{aa}$, $—Si(R^{aa})_3$, $—OSi(R^{aa})_3$—$C(=S)N(R^{bb})_2$, $—C(=O)SR^{aa}$, $—C(=S)SR^{aa}$, $—SC(=S)SR^{aa}$, $—SC(=O)SR^{aa}$, $—OC(=O)SR^{aa}$, $—SC(=O)OR^{aa}$, $—SC(=O)R^{aa}$, $—P(=O)(R^{aa})_2$, $—P(=O)(OR^{cc})_2$, $—OP(=O)(R^{aa})_2$, $—OP(=O)(OR^{cc})_2$, $—P(=O)(N(R^{bb})_2)_2$, $—OP(=O)(N(R^{bb})_2)_2$, $—NR^{bb}(=O)(R^{aa})_2$, $—NR^{bb}P(=O)(OR^{cc})_2$, $—NR^{bb}P(=O)(N(R^{bb})_2)_2$, $—P(R^{cc})_2$, $—P(OR^{cc})_2$, $—P(R^{cc})_3^+X^-$, $—P(OR^{cc})_3^+X^-$, $—P(R^{cc})_4$, $—P(OR^{cc})_4$, $—OP(R^{cc})_2$, $—OP(R^{cc})_3^+X^-$, $—OP(OR^{cc})_2$, $—OP(OR^{cc})_3^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_6$-14 aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C(=O)R^{aa}$, $—C(=O)N(R^{cc})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$, —OP(═O)$(R^{ee})_2$, —OP(═O)$(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl$)(C_{1-6}$ alkyl), —$N(OH)(C_{1-6}$ alkyl), —NH(OH), —SH, —$SC_{1-6}$ alkyl, —$SS(C_{1-6}$ alkyl), —C(═O)$(C_{1-6}$ alkyl), —$CO_2H$, —$CO_2(C_{1-6}$ alkyl), —OC(═O)$(C_{1-6}$ alkyl), —$OCO_2(C_{1-6}$ alkyl), —C(═O)$NH_2$, —C(═O)$N(C_{1-6}$ alkyl$)_2$, —OC(═O)$NH(C_{1-6}$ alkyl), —NHC(═O)$(C_{1-6}$ alkyl), —$N(C_{1-6}$ alkyl)C(═O)$(C_{1-6}$ alkyl), —$NHCO_2(C_{1-6}$ alkyl), —NHC(═O)$N(C_{1-6}$ alkyl$)_2$, —NHC(═O)$NH(C_{1-6}$ alkyl), —NHC(═O)$NH_2$, —C(═NH)$O(C_{1-6}$ alkyl), —OC(═NH)$(C_{1-6}$ alkyl), —OC(═NH)$OC_{1-6}$ alkyl, —C(═NH)$N(C_{1-6}$ alkyl$)_2$, —C(═NH)$NH(C_{1-6}$ alkyl), —C(═NH)$NH_2$, —OC(═NH)$N(C_{1-6}$ alkyl$)_2$, —OC(NH)$NH(C_{1-6}$ alkyl), —OC(NH)$NH_2$, —NHC(NH)$N(C_{1-6}$ alkyl$)_2$, —NHC(═NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$ —C(═S)$N(C_{1-6}$ alkyl$)_2$, C(═S)$NH(C_{1-6}$ alkyl), C(═S)$NH_2$, —C(═O)$S(C_{1-6}$ alkyl), —C(═S)$SC_{1-6}$ alkyl, —SC(═S)$SC_{1-6}$ alkyl, —P(═O)$(OC_{1-6}$ alkyl$)_2$, —P(═O)$(C_{1-6}$ alkyl$)_2$, —OP(═O)$(C_{1-6}$ alkyl$)_2$, —OP(═O)$(OC_{1-6}$ alkyl$)_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_2$-6alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(═O)$R^{X1}$, —C(═O)$OR^{X1}$, —C(═O)—O—C(═O)$R^{X1}$, —C(═O)$SR^{X1}$, —C(═O)$N(R^{X1})_2$, —C(═S)$R^{X1}$, —C(═S)$N(R^{X1})_2$, and —C(═S)$S(R^{X1})$, —C(═$NR^{X1}$)$R^{X1}$, —C(═$NR^{X1}$)$OR^{X1}$, —C(═$NR^{X1}$)$SR^{X1}$, and —C(═$NR^{X1}$)$N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —$C(═O)R^{aa}$, —$C(═O)N(R^{cc})_2$, —$CO_2R^{aa}$, —$SO_2R^{aa}$, —$C(═NR^{bb})R^{aa}$, —$C(═NR^{cc})OR^{aa}$, —$C(═NR^{cc})N(R^{cc})_2$, —$SO_2N(R^{cc})_2$, —$SO_2R^{cc}$, —$SO_2OR^{cc}$, —$SOR^{aa}$, —$C(═S)N(R^{cc})_2$, —$C(═O)SR^{cc}$, —$C(═S)SR^{cc}$, —$P(═O)(OR^{cc})_2$, —$P(═O)(R^{aa})_2$, —$P(═O)(N(R^{aa})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —$N(R^{cc})_2$, —$C(═O)R^{aa}$, —$C(═O)N(R^{cc})_2$, —$CO_2R^{aa}$, —$SO_2R^{aa}$, —$C(═NR^{cc})R^{aa}$, —$C(═NR^{cc})OR^{aa}$, —$C(═NR^{cc})N(R^{cc})_2$, —$SO_2N(R^{cc})_2$, —$SO_2R^{cc}$, —$SO_2OR^{cc}$, —$SOR^{aa}$, —$C(═S)N(R^{cc})_2$, —$C(═O)SR^{cc}$, —$C(═S)SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —$C(═O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(0-phenylazophenoxy)propanamide, 4 chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —$C(═O)OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-1-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumcoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4 dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4 dimethoxy-6-nitrobenzyl carbamate, phenyl(o-nitrophenyl)methyl carbamate, t-amyl carbamate, S benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-1-butylphenyl carbamate, 4-(trimethylammonium) benzyl carbamate, and 2,4,6-trimethylbenzyl carbamate.

Nitrogen protecting groups such as sulfonamide groups (e.g., —$S(═O)_2R^{aa}$) include, but are not limited to, p-toluenesulfonamide (Ts), benzenesulfonamide, 2,3,6, -trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pme), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfonamide, o-nitrobenzenesulfonamide (Nps), 2,4-dinitrobenzenesulfenamide, pentachlorobenzenesulfenamide, 2-nitro-4-methoxybenzenesulfonamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), 1-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4 dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4 dinitrophenyl, benzyl (Bn), p-methoxybenzyl, 3,4 dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, 1-butyldimethylsilyl (TBDMS), t-butyldiphenylsilyl (TBDPS), tribenzylsilyl, tri-p-xylylsilyl, triphenylsilyl, diphenylmethylsilyl (DPMS), 1-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4 oxopentanoate (levulinate), 4,4 (ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4 (methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4 dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(═O)$SR^{aa}$, —C(═O)$R^{aa}$, —$CO_2R^{aa}$, —C(═O)$N(R^{bb})_2$, —C(═$NR^{bb}$)$R^{aa}$, —C(═$NR^{bb}$)$OR^{aa}$, —C(═$NR^{bb}$)$N(R^{bb})_2$, —S(═O)$R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —P(═O)$(R^{aa})_2$, —P(═O)$(OR^{cc})_2$, and —P(═O)$(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

As used herein, a "leaving group" (LG) is an art-understood term referring to a molecular fragment that departs with a pair of electrons in a heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(═O)$SR^{aa}$, —OC(═O)$R^{aa}$, —$OCO_2R^{aa}$, —OC(═O)$N(R^{bb})_2$, —OC(═$NR^{bb}$)$R^{aa}$, —OC(═$NR^{bb}$)$OR^{aa}$, —OC(═$NR^{bb}$)$N(R^{bb})_2$, —OS(═O)$R^{aa}$, —$OSO_2R^{aa}$, —$OP(R^{cc})_2$, —$OP(R^{cc})_3$, —OP(═$O)_2R^{aa}$, —OP(═O)$(R^{aa})^2$, —OP(═O)$(OR^{cc})_2$, —OP(═$O)_2N(R^{bb})_2$, and —OP(═O)$(NR^{bb})_2$, wherein $R^{aa}$, $R^{bb}$, and $R^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, amines, ammonia, alcohols, ether moieties, sulfur-containing moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. Compounds described herein, including, for example, metformin, may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base.

Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal or genetically engineered animal (e.g., a transgenic mouse). A "patient" refers to a human subject in need of treatment of a disease (e.g., a neurological disease or neurodegenerative disease), which may include, but is not limited to, human subjects with microsatellite repeat expansion mutations.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent a neurological disease associated with repeat expansions, or to reduce the accumulation of RAN protein in a subject, tissue, or cell.

The terms "condition," "disease," and "disorder" are used interchangeably.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is effective for treating a disease. In certain embodiments, a therapeutically effective amount is effective for treating an neurological disease associated with repeat expansions. In certain embodiments, a therapeutically effective amount is effective for treating a neurodegenerative disease associated with repeat expansions. In certain embodiments, a therapeutically effective amount is an amount effective in reducing repeat expansions. In certain embodiments, a therapeutically effective amount is an amount effective in reducing the transcription of RNAs that produce RAN proteins. In certain embodiments, a therapeutically effective amount is an amount effective in reducing the translation of RAN proteins. In certain embodiments, a therapeutically effective amount is an amount effective in reducing the level of one or more RAN proteins in a subject. In certain embodiments, a therapeutically effective amount is an amount effective in reducing the level of one or more RAN proteins and treating a neurological disease associated with repeat expansions. In certain embodiments, a therapeutically effective amount is an amount effective in reducing the level of one or more RAN proteins and treating a neurological disease associated with RAN protein accumulation. In certain embodiments, a therapeutically effective amount is an amount effective in reducing the accumulation of RAN proteins. In certain embodiments, a therapeutically effective amount is effective for treating amyotrophic lateral sclerosis (ALS). In certain embodiments, a therapeutically effective amount is effective for treating frontotemporal dementia (FTD). In certain embodiments, a therapeutically effective amount is effective for treating C9ORFf72 ALS. In certain embodiments, a therapeutically effective amount is effective for treating C9ORFf72 FTD. In certain embodiments, a therapeutically effective amount is effective for treating spinocerebellar ataxia. In certain embodiments, a therapeutically effective amount is effective for treating spinocerebellar ataxia type 1, spinocerebellar ataxia type 2, spinocerebellar ataxia type 3, or spinocerebellar ataxia type 8. In certain embodiments, a therapeutically effective amount is effective for treating a spinocerebellar ataxia type 6, spinocerebellar ataxia type 7, spinocerebellar ataxia type 10, spinocerebellar ataxia type 12, spinocerebellar ataxia type 17, spinocerebellar ataxia type 31, or spinocerebellar ataxia type 36. In certain embodiments, a therapeutically effective amount is effective for treating myotonic dystrophy. In certain embodiments, a therapeutically effective amount is effective for treating myotonic dystrophy type 1, myotonic dystrophy type 2, or Fuch's corneal endothelial dystrophy. In certain embodiments, a therapeutically effective amount is effective for treating spinal bulbar muscular atrophy. In certain embodiments, a therapeutically effective amount is effective for treating dentatorubral-pallidoluysian atrophy. In certain embodiments, a therapeutically effective amount is effective for treating Huntington's disease. In certain embodiments, a therapeutically effective amount is effective for treating Fragile X Tremor Ataxia Syndrome (FXTAS). In certain embodiments, a therapeutically effective amount is effective for Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; or Fragile XE syndrome (FRAXE).

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for preventing a neurological disease associated with repeat expansions. In certain embodiments, a prophylactically effective amount is effective for preventing a neurological disease associated with RAN protein accumulation. In certain embodiments, a prophylactically effective amount is effective for preventing a neurodegenerative disease associated with repeat expansions. In certain embodiments, a prophylactically effective amount is effective in preventing C9ORFf72 amyotrophic lateral sclerosis (ALS) or C9ORFf72 frontotemporal dementia; myotonic dystrophy type 1 (DM1) and myotonic dystrophy type 2 (DM2); spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease; Fuch's endothelial corneal dystrophy (FECD); Fragile X Tremor Ataxia Syndrome (FXTAS); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; or Fragile XE syndrome (FRAXE). In certain embodiments, a prophylactically effective amount is effective in reducing the level of RAN proteins in tissues from subjects with gene mutations that can cause C9orf72 amyotrophic lateral sclerosis (ALS) or C9orf72 frontotemporal dementia; myotonic dystrophy type 1 (DM1) and myotonic dystrophy type 2 (DM2); spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease; Fuch's endothelial corneal dystrophy (FECD); Fragile X Tremor Ataxia Syndrome (FXTAS); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; or Fragile XE syndrome (FRAXE). In certain embodiments, a prophylactically effective amount is effective in preventing the accumulation of RAN proteins in tissues from subjects with gene mutations that can cause C9orf72 amyotrophic lateral sclerosis (ALS) or C9orf72 frontotemporal dementia; myotonic dystrophy type 1 (DM1) and myotonic dystrophy type 2 (DM2); spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease; Fuch's endothelial corneal dystrophy (FECD); Fragile X Tremor Ataxia Syndrome (FXTAS)); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; or Fragile XE syndrome (FRAXE).

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus. Biological samples further include white blood cells in peripheral blood, or brain lysates and cerebrospinal fluid.

A "protein" or "peptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

A "RAN protein (repeat-associated non-ATG translated protein)" is a polypeptide translated from sense or antisense RNA sequences carrying a nucleotide expansion without the requirement for an AUG initiation codon. Generally, RAN proteins comprise "expansion repeats" or "repeat expansions" of an amino acid, termed poly amino acid repeats. For example, "AAAAAAAAAAAAAAAAAAAA" (poly-Alanine) (SEQ ID NO: 1), "LLLLLLLLLLLLLLLLLL" (poly-Leucine) (SEQ ID NO: 2), "SSSSSSSSSSSSSSSSSSSS" (poly-Serine) (SEQ ID NO: 3), or "CCCCCCCCCCCCCCCCCCCC" (poly-Cysteine) (SEQ ID NO: 4) are poly amino acid repeats that are each 20 amino acid residues in length. RAN proteins can have a poly amino acid repeat of at least 25, at least 30, at least 40, at least 50, at least 60, at least 70, at least 80, at least 90, at least 100, or at least 200 amino acid residues in length. In some embodiments, a RAN protein has a poly amino acid repeat more than 200 amino acid residues in length. Generally, RAN proteins are translated from abnormal repeat expansions (e.g., CAG repeats) of DNA. In general, RAN proteins comprise expansion repeats of one or amino acid, termed poly amino acid repeats (e.g., di-amino acid repeats). For example, in the context of ALS/FTD, which results from a repeat expansion of the hexanucleotide sequence GGGGCC in the C9ORF72 gene, the following di-amino acid repeat-containing RAN proteins have been identified: poly-(Gly-Ala), poly-(Gly-Pro), poly-(Gly-Arg), poly-(5 Pro-Ala), or poly-(Pro-Arg), also referred to as poly(GA), poly(GP), poly(GR), poly(PA), and poly(PR), respectively. Without wishing to be bound by any particular theory, RAN protein accumulation (e.g., in the nucleus or cytoplasm of a cell) disrupts cellular function and induces cellular toxicity. In some embodiments, translation and accumulation of RAN proteins is associated with a disease, for example, a neurological disease, neurodegenerative disease, or neurodegenerative disorder. Examples of diseases associated with RAN protein translation and accumulation include but are not limited to C9ORFf72 ALS, C9ORFf72 FTD, myotonic dystrophy type 1 (DM1) and myotonic dystrophy type 2 (DM2), spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease (HD); Fuch's endothelial corneal dystrophy (FECD); Fragile X Tremor Ataxia Syndrome (FXTAS); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; and Fragile XE syndrome (FRAXE).

A "repeat expansion" is a mutation which increases the number of times that a short nucleotide sequence is repeated. Exemplary repeat expansions are provided above in the definition of "RAN protein."

"C9ORFf72 amyotrophic lateral sclerosis" or "C9ORFf72 ALS" refers to amyotrophic lateral sclerosis associated with a hexanucleotide repeat expansion mutation in the chromosome 9 open reading frame 72 (C9ORFf72) gene. "C9ORFf72 frontotemporal dementia" or "C9ORFf72 FTD" refers to frontotemporal dementia associated with a hexanucleotide expansion mutation in the C9ORFf72 gene.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells. Examples of neurodegenerative diseases include but are not limited to C9ORFf72 ALS, C9ORFf72 FTD, myotonic dystrophy type 1 (DM1) and myotonic dystrophy type 2 (DM2), spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease (HD); Fuch's endothelial corneal dystrophy (FECD); Fragile X Tremor Ataxia Syndrome (FXTAS); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; and Fragile XE syndrome (FRAXE). Neuromuscular diseases refer to a type of neurological disease marked by pathologies of the nerves or neuromuscular junctions. Exemplary neuromuscular diseases include but are not limited to amyotrophic lateral sclerosis, multiple sclerosis, and spinal muscular atrophy.

BRIEF DESCRIPTION OF THE DRAWINGS

Protein blots were run on protein lysates from HEK293T cells transfected with various repeat expansion constructs shown in FIG. 1A. In FIG. 1B, the lane labeled KMQ has a methionine encoding ATG immediately 5' to the CAG repeat expansion and located within the polyGln reading frame. The KKQ vector contains a CAG expansion without an AUG initiation codon, and indicates: Ser-Flag, Ala-HA, Gln-Myc. These constructs contain epitope tags that are incorporated into the C-terminal regions of the ATG-initiated poly-Gln and non-ATG initiated RAN proteins (poly-Gln, poly-Leu-Pro-Ala-Cys and poly-Gly-Pro) which are expressed across these repeat expansions. The lane labeled CCTG expresses the following RAN proteins: LPAC-Flag, LPAC-HA, and LPAC-Myc. The lane labeled G4C2 is designed to detect the following RAN proteins: GP-Flag, GR-HA, and GA-Myc. Treatment of the transfected HEK293T cells with metformin shows reduced RAN protein levels of the following RAN proteins of poly-LPAC (poly-Leucine-Proline-Alanine-Cysteine in all three reading frames, poly-Ala, and poly-GP (poly-glycine-proline).

FIG. 3A shows a protein blot indicating that metformin reduces RAN protein expression in HEK293T cells transiently transfected with CAG, CCTG, CAGG, and $G4C_2$ expansion constructs. FIG. 3B shows data indicating that metformin reduces levels of p-PKR (T446 and T451) in cells transfected with repeat expansion constructs. FIG. 3C is a schematic diagram showing the study design for two metformin treatment groups, with treatment at 5 mM metformin from 2 to 5 months of age or from six to 9 months of age. FIG. 3D shows data quantifying GA aggregates and indicates a reduction in GA aggregates in mice treated with 5 mM metformin in their drinking water from 2-5 months compared to untreated C9-500 mice. FIG. 3E shows quantification of GFAP staining, indicating decreased levels of reactive gliosis in C9-500 metformin treated mice compared to C9-500 control animals. FIG. 3F shows DigiGait analyses indicating that of eight parameters that differed between untreated C9-500 and NT controls, 6 of these parameters improved in C9-500 animals treated with metformin. Exemplary data from four of these eight parameters are shown. FIG. 3G shows open field analyses showing decreased center time in C9-500 animals that is normalized in C9-500 animals treated with metformin. FIG. 3H shows data from MSD assays indicating soluble GP levels are reduced in C9-500 animals treated with metformin compared to C9-500 controls. FIG. 3I shows GA aggregates are reduced in C9-500 animals treated with metformin compared to C9-500 controls. FIG. 3J is a schematic showing that chronic activation of the PKR pathway by repeat expansion RNAs favors RAN translation through the integrated stress response and eIF2α phosphorylation.

In FIG. 5B, the lane labeled KMQ has a methionine encoding ATG immediately 5' to the CAG repeat expansion and located within the polyGln reading frame. The KKQ vector contains a CAG expansion without an AUG initiation codon, and indicates: Ser-Flag, Ala-HA, Gln-Myc. These constructs contain epitope tags that are incorporated into the C-terminal regions of the ATG-initiated poly-Gln and non-ATG initiated RAN proteins (poly-Gln, poly-Leu-Pro-Ala-Cys and poly-Gly-Pro) which are expressed across these repeat expansions. The lane labeled CCTG expresses the following RAN proteins: LPAC-Flag, LPAC-HA, and LPAC-Myc. The lane labeled G4C2 is designed to detect the following RAN proteins: GP-Flag, GR-HA, and GA-Myc. Treatment of the transfected HEK293T cells with metformin shows reduced RAN protein levels of the following RAN proteins of poly-LPAC (poly-Leucine-Proline-Alanine-Cysteine in all three reading frames, poly-Ala, and poly-GP (poly-glycine-proline).

FIGS. 6G and 6H show decreased reactive gliosis as measured by GFAP staining (FIG. 6H) in metformin treated vs. untreated C9-BAC animals (FIG. 6I). Statistical analyses were performed using two-tailed t-test (panels a-f, i), $^{*}P<0.05$, $^{}P<0.01$, $^{*}P<0.001$. For FIG. 6F and FIG. 6G, statistical analyses were performed using one-way ANOVA with Tukey analyses for multiple comparisons $^{*}P<0.05$, $^{}P<0.01$, $^{*}P<0.001$.

DETAILED DESCRIPTION OF CERTAIN EMBODIMENTS OF THE INVENTION

Figure 1A:
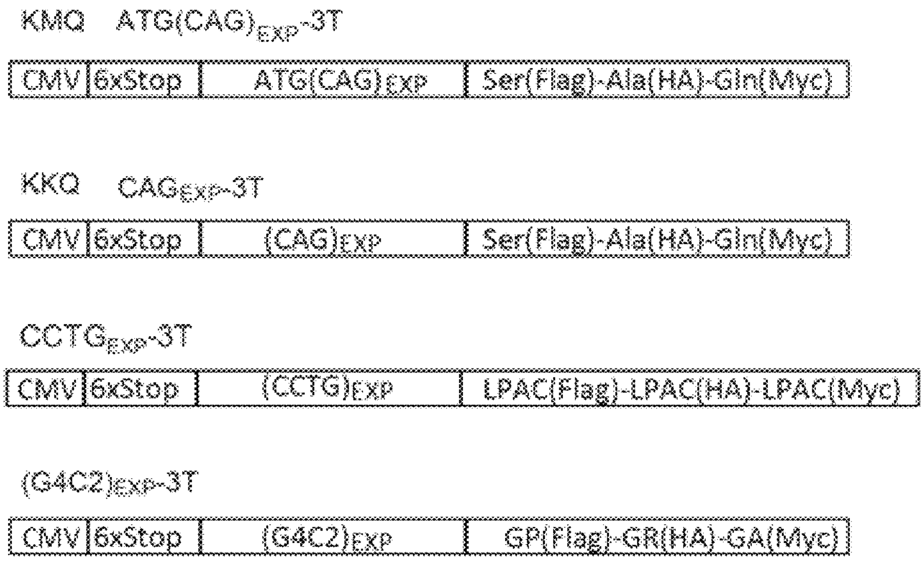
FIG. 1B shows that metformin inhibits RAN translation in multiple reading frames in cells that have been transfected with constructs containing CAG, CCTG, or GGGGCC repeat expansion motifs.

The present invention provides compositions, methods, uses, and kits for using compounds of Formulae (I), (II), (III), (III-A), and (III-B) (e.g., metformin, buformin, phenformin) to treat and/or preventing a neurological disease associated with repeat expansions in a subject in need thereof. Metformin is used to inhibit RAN translation. In certain embodiments, the neurological disease to be treated is associated with repeat expansions. In certain embodiments, the neurological disease is associated with repeat expansion mutations that undergo RAN protein translation. In certain embodiments, the neurological disease is associated with the expression of RAN proteins.

In one aspect, the disclosure provides a method for administering to a subject a therapeutically effective amount of a compound of Formula (I), (II), (III), (III-A), or (III-B) (e.g., metformin, buformin, phenformin), or a pharmaceutically acceptable salt, solvate, hydrate, tautomer, stereoisomer, derivative, or prodrug thereof. In one aspect, the disclosure provides a method for administering to the biological sample (e.g., cells or tissue) a therapeutically effective amount of a compound described herein (e.g., metformin), or a pharmaceutically acceptable salt, solvate, hydrate, tautomer, stereoisomer, derivative, or prodrug thereof. A biological sample includes, but is not limited to, cells, tissue, cerebrospinal fluid, blood, or tissue biopsy samples from a subject. In certain embodiments, the method comprises treating a neurological disease associated with repeat expansions in a subject (e.g., C9ORFf72 amyotrophic lateral sclerosis (ALS) or C9ORFf72 frontotemporal dementia; myotonic dystrophy type 1 (DM1) and myotonic dystrophy type 2 (DM2); spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease (HD); Fuch's endothelial corneal dystrophy (FECD); Fragile X Tremor Ataxia Syndrome (FXTAS)); Huntington's disease-like 2 syndrome (HDL2); Fragile X syndrome (FXS); FRAXA; disorders related to 7p11.2 folate-sensitive fragile site FRA7A; disorders related to folate-sensitive fragile site 2q11 FRA2A; and Fragile XE syndrome (FRAXE), the method comprising administering to the subject a therapeutically effective amount of a compound of Formula (I), (II), (III), (III-A), or (III-B) (e.g., metformin), or a pharmaceutically acceptable salt, solvate, hydrate, tautomer, stereoisomer, derivative, or prodrug thereof. In certain embodiments, the method comprises treating a neurological disease associated with repeat expansions in a biological sample (e.g., cells) from a patient with the disease, the method comprising contacting the biological sample with a therapeutically effective amount of a compound of Formula (I), (II), (III), (III-A), or (III-B) (e.g., metformin), or a pharmaceutically acceptable salt, solvate, hydrate, tautomer, stereoisomer, derivative, or prodrug thereof. In certain embodiments, the method comprises treating a neurological disease associated with repeat expansions in a biological sample from a patient with the disease, the method comprising contacting the biological sample with a therapeutically effective amount of a compound of Formula (I), (II), (III), (III-A), or (III-B) (e.g., metformin), or a pharmaceutically acceptable salt, solvate, hydrate, tautomer, stereoisomer, derivative, or prodrug thereof. In certain embodiments, the method comprises treating a neurological disease associated with repeat expansions in a tissue from a patient with the discase, the method comprising contacting the tissue with a therapeutically effective amount of a compound of Formula (I), (II), (III), (III-A), or (III-B) (e.g., metformin), or a pharmaceutically acceptable salt, solvate, hydrate, tautomer, stereoisomer, derivative, or prodrug thereof. In certain embodiments, the method comprises treating a neurological disease associated with the accumulation of RAN proteins in a subject, the method comprising administering to the subject a therapeutically effective amount of a compound of Formula (I), (II), (III), (III-A), or (III-B) (e.g., metformin), or a pharmaceutically acceptable salt, solvate, hydrate, tautomer, stereoisomer, derivative, or prodrug thereof.

Another aspect of the invention relates to methods of treating a neurological disease associated with repeat expansions in a subject or cell, by administering to the subject or contacting the biological sample (e.g., cells or tissue) with a therapeutically effective amount of a compound of Formula (I), (II), (III), (III-A), or (III-B) (e.g., metformin), or a pharmaceutically acceptable salt, solvate, hydrate, tautomer, stereoisomer, derivative, or prodrug thereof, whereby the method comprises modulating RAN protein translation. In certain embodiments, the method comprises modulating the steady state levels of RAN proteins. In certain embodiments, the method comprises reducing the accumulation of RAN protein in a subject. In certain embodiments, the method comprises reducing the accumulation of RAN protein in a tissue. In certain embodiments, the method comprises reducing the accumulation of RAN protein in a cell. In certain embodiments, the modulating comprises negative regulation of RAN protein translation. In certain embodiments, the modulating comprises inhibition of RAN protein translation. In certain embodiments, the modulating comprises negative regulation of RAN protein translation and reduced accumulation of RAN protein in a cell. In certain embodiments, the modulating comprises negative regulation of RAN protein accumulation in a cell or in patient tissue. In certain embodiments, the modulating comprises changes related to translation of RAN proteins. In certain embodiments, the modulating comprises changes related to turnover of RAN proteins.

In certain embodiments, the method comprises reducing the level of one or more repeat associated non-ATG (RAN) proteins in a cell, tissue, biological sample, or subject. In certain embodiments, the method comprises reducing the translation of RAN proteins in a cell, tissue, biological sample, or subject. In certain embodiments, the method comprises reducing the accumulation of RAN proteins in a cell, tissue, biological sample, or subject. In certain embodiments, the method comprises reducing the level of one or more RAN proteins in a cell, tissue, biological sample, or subject by administering to the subject or contacting the cell, tissue, or biological sample, with a compound of Formula (I), (II), (III), (III-A), or (III-B) (e.g., metformin), or a pharmaceutically acceptable salt, solvate, or hydrate, tautomer, stereoisomer, derivative, or prodrug. The levels of any RAN protein may be reduced using a compound of Formula (I), (II), (III), (III-A), or (III-B) (e.g., metformin), or a pharmaceutically acceptable salt, solvate, or hydrate, tautomer, stereoisomer, derivative, or prodrug. The levels of any RAN protein comprises, in certain embodiments, the steady state levels of one or more RAN proteins. In certain embodiments, the one or more RAN proteins are selected from the group consisting of poly-Leucine-Proline-Alanine-Cysteine, poly-Glutamine-Alanine-Glycine-Arginine, poly-Glycine-Proline, poly-Glycine-Alanine, poly-Glycine-Arginine, poly-Proline-Alanine, poly-Proline-Arginine, poly-Alanine, poly-Leucine, poly-Serine, poly-Cysteine, poly-Glutamine, poly-Arginine, poly-Glycine, poly-Proline, poly-Isoleucine-Leucine-Phenylalanine-Tyrosine-Serine, Poly-Tryptophan-Asparagine-Glycine-Methionine-Glutamine, poly-Phenylalanine-Histidine-Serine-Isoleucine-Proline, poly-Glycine-Leucine, poly-Tryptophan-Alanine, poly-Glutamine-Alanine, and combinations thereof. In certain embodiments, the method comprises reducing the level of the RAN protein, poly-Leucine-Proline-Alanine-Cysteine. In certain embodiments, the method comprises reducing the level of the RAN protein, poly-Glutamine-Alanine-Glycine-Arginine. In certain embodiments, the method comprises reducing the level of the RAN protein, poly-Glycine-Proline. In certain embodiments, the method comprises reducing the level of the RAN protein poly-Glycine-Alanine. In certain embodiments, the method comprises reducing the level of the RAN protein, poly-Glycine-Arginine. In certain embodiments, the method comprises reducing the level of the RAN protein, poly-Proline-Alanine. In certain embodiments, the method comprises reducing the level of the RAN protein, poly-Proline-Arginine. In certain embodiments, the method comprises reducing the level of RAN proteins that are poly-Glycine-Leucine, poly-Tryptophan-Alanine, poly-Glutamine-Alanine, poly-Glycine-Proline, and/or poly-Proline-Arginine. In certain embodiments, the method comprises reducing the level of the RAN protein, poly-Alanine. In certain embodiments, the method comprises reducing the level of the RAN protein, poly-Leucine. In certain embodiments, the method comprises reducing the level of the RAN protein, poly-Serine. In certain embodiments, the method comprises reducing the level of the RAN protein, poly-Cysteine. In certain embodiments, the method comprises reducing the level of the RAN protein, poly-Glutamine. In certain embodiments, the method comprises reducing the level of RAN proteins that are poly-Glutamine, which are associated with spinocerebellar ataxia type 12. In certain embodiments, the method comprises reducing the level of RAN proteins that are poly-Alanine, poly-Leucine, poly-Serine, and/or poly-Cysteine, which are associated with DM1, spinocerebellar ataxia types 1, 2, 3, 6, 7, 8, 12, 17; spinal bulbar muscular atrophy; dentatorubral-pallidoluysian atrophy (DRPLA), and Huntington's disease. In certain embodiments, the method comprises reducing the level of RAN proteins that are poly-Glutamine, poly-Alanine, poly-Leucine, poly-Serine, and/or poly-Cysteine, which are associated with Huntington's disease-like 2 syndrome (HDL2); and Fuch's endothelial corneal dystrophy (FECD). In certain embodiments, the method comprises reducing the level of RAN proteins that are poly-Arginine, poly-Glycine, poly-Alanine, and/or poly-Proline, which are associated with Fragile X syndrome (FXS); FRAXA; disorders related to 7p11.2 folate-sensitive fragile site FRA7A; disorders related to folate-sensitive fragile site 2q11 FRA2A; and Fragile XE syndrome (FRAXE). In certain embodiments, the method comprises reducing the level of RAN proteins that are poly-Alanine, poly-Leucine, poly- Serine, poly-Cysteine, or poly-Leu-Pro-Ala-Cys, which are associated with DM2. In certain embodiments, the method comprises reducing the level of RAN proteins that are poly-Gln-Ala-Gly-Arg, which are associated with DM2. In certain embodiments, the method comprises reducing the level of RAN proteins that are poly-Gly-Pro, poly-Gly-Arg, poly-Gly-Ala, poly-Pro-Ala, or poly-Pro-Arg, which are associated with sense C9ORFf72 ALS and C9ORFf72 FTD. In certain embodiments, the method comprises reducing the level of RAN proteins that are poly-Pro-Ala, poly-Pro-Arg, poly-Gly-Pro, poly-Pro-Ala, or poly-Pro-Arg, which are associated with antisense C9ORFf72 ALS and antisense C9ORFf72 FTD. In certain embodiments, the method comprises reducing the level of RAN proteins that are Poly-Tryptophan-Asparagine-Glycine-Methionine-Glutamine or poly-Phenylalanine-Histidine-Serine-Isoleucine-Proline, which are associated with spinocerebellar ataxia type 31. In certain embodiments, the method comprises reducing the level of RAN proteins that are poly-Isoleucine-Leucine-Phenylalanine-Tyrosine-Serine, which are associated with spinocerebellar ataxia type 10.

Another aspect of the invention relates to methods of reducing the accumulation of repeat associated non-ATG protein (RAN) in a subject, tissue, or cell, the method comprising administering to the subject or cell a therapeutically effective amount of a compound of Formula (I), (II), (III), (III-A), or (III-B) (e.g., metformin), or a pharmaceutically acceptable salt, solvate, hydrate, tautomer, stereoisomer, derivative, or prodrug thereof, or a pharmaceutical composition thereof.

In certain embodiments, the number of poly-amino acid repeats in the RAN protein is at least 35. In certain embodiments, the number of poly-amino acid repeats in the RAN protein is at least 45. In certain embodiments, the number of poly-amino acid repeats in the RAN protein is at least 50. In certain embodiments, the number of poly-amino acid repeats in the RAN protein is at least 70. In certain embodiments, the number of poly-amino acid repeats in the RAN protein is at least 80. In certain embodiments, the number of poly-amino acid repeats in the RAN protein is at least 90. In certain embodiments, the number of poly-amino acid repeats in the RAN protein is at least 100. In certain embodiments, the number of poly-amino acid repeats in the RAN protein is at least 120. In certain embodiments, the number of poly-amino acid repeats in the RAN protein is at least 150. In certain embodiments, the number of poly-amino acid repeats in the RAN protein is at least 200. In certain embodiments, the number of poly-amino acid repeats in the RAN protein is at least 250.

In certain embodiments, the neurological disease to be treated is associated with repeat expansions (e.g., repeat expansion mutations that undergo RAN protein translation). In certain embodiments, the neurological disease is associated with the expression of RAN proteins. In certain embodiments, the repeat expansions comprise GGGGCC expansions and GGCCCC expansions. In certain embodiments, the repeat expansions comprise GGGGCC expansions. In certain embodiments, the repeat expansions comprise GGCCCC expansions. In certain embodiments, the repeat expansions comprise CAG expansions and CTG expansions. In certain embodiments, the repeat expansions comprise CAG expansions. In certain embodiments, the repeat expansions comprise CTG expansions. In certain embodiments, the repeat expansions comprise CAGG expansions and CCTG expansions. In certain embodiments, the repeat expansions comprise CAGG expansions. In certain embodiments, the repeat expansions comprise CCTG expansions.

In certain embodiments, the neurological disease being treated is a neurodegenerative disorder. In certain embodiments, the neurological disease being treated is a neuromuscular disorder. In certain embodiments, the neurological disease is associated with GGGGCC expansions and/or GGCCCC expansions. In certain embodiments, the neurological disease is associated with GGGGCC expansions and GGCCCC expansions. In certain embodiments, the neurological disease is associated with GGGGCC expansions. In certain embodiments, the neurological disease is associated with GGCCCC expansions. In certain embodiments, the neurological disease associated with GGGGCC expansions and/or GGCCCC expansions is amyotrophic lateral sclerosis (ALS). In certain embodiments, the neurological disease associated with GGGGCC expansions and/or GGCCCC expansions is frontotemporal dementia (FTD). In certain embodiments, the neurological disease associated with GGGGCC expansions and/or GGCCCC expansions is C9ORFf72 ALS. In certain embodiments, the neurological disease is associated with GGGGCC expansions and/or GGCCCC expansions C9ORFf72 FTD.

In certain embodiments, the neurological disease is associated with CAG expansions and/or CTG expansions. In certain embodiments, the neurological disease is associated with CAG expansions and CTG expansions. In certain embodiments, the neurological disease is associated with CAG expansions. In certain embodiments, the neurological disease is associated with CTG expansions. In certain embodiments, the neurological disease associated with CAG expansions and/or CTG expansions is spinocerebellar ataxia (SCA). In certain embodiments, the neurological disease is associated with TGGAA expansions. In certain embodiments, the neurological disease associated with TGGAA expansions is spinocerebellar ataxia. In certain embodiments, the neurological disease associated with TGGAA expansions is spinocerebellar ataxia type 31. In certain embodiments, the neurological disease is associated with GGCCTG expansions. In certain embodiments, the neurological disease associated with GGCCTG expansions is spinocerebellar ataxia type 36. In certain embodiments, the neurological disease is associated with TGGGCC expansions. In certain embodiments, the neurological disease is associated with 5' TGGGCC expansions. In certain embodiments, the neurological disease associated with TGGGCC expansions is spinocerebellar ataxia type 36. In certain embodiments, the neurological disease associated with 5' TGGGCC expansions is spinocerebellar ataxia type 36. In certain embodiments, the neurological disease is associated with GGCCCA expansions of another DNA strand. In certain embodiments, the neurological disease is associated with 5' GGCCCA expansions of another DNA strand. In certain embodiments, the neurological disease associated with 5' GGCCCA expansions of another DNA strand is spinocerebellar ataxia type 36. In certain embodiments, the neurological disease is associated with ATCCT expansions. In certain embodiments, the neurological disease is associated with 5' ATCCT expansions. In certain embodiments, the neurological disease associated with ATCCT expansions is spinocerebellar ataxia type 10. In certain embodiments, the neurological disease associated with 5' ATCCT expansions is spinocerebellar ataxia type 10. In certain embodiments, the neurological disease is associated with AGGAT expansions of another DNA strand. In certain embodiments, the neurological disease is associated with 5' AGGAT expansions of another DNA strand. In certain embodiments, the neurological disease associated with AGGAT expansions of another DNA strand is spinocerebellar ataxia type 10.

In certain embodiments, the neurological disease associated with 5' AGGAT expansions of another DNA strand is spinocerebellar ataxia type 10.

In certain embodiments, the spinocerebellar ataxia is spinocerebellar ataxia type 1, spinocerebellar ataxia type 2, spinocerebellar ataxia type 3, or spinocerebellar ataxia type 8. In certain embodiments, the spinocerebellar ataxia is spinocerebellar ataxia type 1. In certain embodiments, the spinocerebellar ataxia is spinocerebellar ataxia type 2. In certain embodiments, the spinocerebellar ataxia is spinocerebellar ataxia type 3. In certain embodiments, the spinocerebellar ataxia is spinocerebellar ataxia type 8. In certain embodiments, the spinocerebellar ataxia is spinocerebellar ataxia type 6, spinocerebellar ataxia type 7, spinocerebellar ataxia type 10, spinocerebellar ataxia type 12, spinocerebellar ataxia type 17, spinocerebellar ataxia type 31, or spinocerebellar ataxia type 36. In certain embodiments, the spinocerebellar ataxia is spinocerebellar ataxia type 6. In certain embodiments, the spinocerebellar ataxia is spinocerebellar ataxia type 7. In certain embodiments, the spinocerebellar ataxia is spinocerebellar ataxia type 10. In certain embodiments, the spinocerebellar ataxia is spinocerebellar ataxia type 12. In certain embodiments, the spinocerebellar ataxia is spinocerebellar ataxia type 17. In certain embodiments, the spinocerebellar ataxia is spinocerebellar ataxia type 31. In certain embodiments, the spinocerebellar ataxia is spinocerebellar ataxia type 36. In certain embodiments, the neurological disease is myotonic dystrophy type 1 or Fuch's corneal endothelial dystrophy. In certain embodiments, the neurological disease is myotonic dystrophy type 1. In certain embodiments, the neurological disease is Fuch's corneal endothelial dystrophy.

In embodiments, the neurological disease is associated with CAGG expansions and/or CCTG expansions. In embodiments, the neurological disease is associated with CAGG expansions and CCTG expansions. In embodiments, the neurological disease is associated with CAGG expansions. In embodiments, the neurological disease is associated with CCTG expansions. In certain embodiments, the neurological disease associated with CAGG expansions and/or CCTG expansions is myotonic dystrophy type 2. In certain embodiments, the neurological disease is associated with RAN protein accumulation.

In certain embodiments, the neurological disease is a neurodegenerative disorder, and is associated with a RAN protein where the number of poly-amino acid repeats in the RAN protein is at least 35. In certain embodiments, the neurological disease is a neurodegenerative disorder, and is associated with a RAN protein where the number of poly-amino acid repeats in the RAN protein is at least 50. In certain embodiments, the neurological disease is a neurodegenerative disorder, and is associated with a RAN protein where the number of poly-amino acid repeats in the RAN protein is at least 70. In certain embodiments, the neurological disease is spinal bulbar muscular atrophy or dentatorubral-pallidoluysian atrophy. In certain embodiments, the neurological disease is spinal bulbar muscular atrophy. In certain embodiments, the neurological disease is dentatorubral-pallidoluysian atrophy.

In certain embodiments, the neurological disease is Huntington's disease. In certain embodiments, the neurological disease is Fragile X Tremor Ataxia Syndrome (FXTAS). In certain embodiments, the neurological disease is Huntington's disease-like 2 syndrome (HDL2); Fragile X syndrome (FXS); disorders related to 7p11.2 folate-sensitive fragile site FRAZA; disorders related to folate-sensitive fragile site 2q11 FRA2A; or Fragile XE syndrome (FRAXE).

The present invention provides methods of diagnosing a patient with a neurological disease associated with repeat expansions, the methods comprising performing an assay to detect levels of RAN proteins in the patient; and diagnosing the patient with a neurological disease associated with repeat expansions based upon the presence of the at least one RAN protein.

The present invention also provides uses of a compound of Formula (I), (II), (III), (III-A), or (III-B) (e.g., metformin), or a pharmaceutically acceptable salt, solvate, hydrate, tautomer, stereoisomer, derivative, or prodrug thereof, to treat and/or prevent a neurological disease associated with repeat expansions in a subject in need thereof. The present invention also provides uses of a compound of Formula (I), (II), (III), (III-A), or (III-B) (e.g., metformin), or a pharmaceutically acceptable salt, solvate, hydrate, tautomer, stereoisomer, derivative, or prodrug thereof, to treat and/or prevent a neurological disease associated with RAN protein accumulation in a subject in need thereof. The present invention provides uses of a compound of Formula (I), (II), (III), (III-A), or (III-B) (e.g., metformin), or a pharmaceutically acceptable salt, solvate, hydrate, tautomer, stereoisomer, derivative, or prodrug thereof, to reduce the levels of RAN protein in a subject or biological sample (e.g., cells or tissue). The present invention provides uses of a compound of Formula (I), (II), (III), (III-A), or (III-B) (e.g., metformin), or a pharmaceutically acceptable salt, solvate, hydrate, tautomer, stereoisomer, derivative, or prodrug thereof, to reduce the accumulation of RAN protein in a subject or biological sample (e.g., cells or tissue). The present invention provides uses of a compound of Formula (I), (II), (III), (III-A), or (III-B) (e.g., metformin), or a pharmaceutically acceptable salt, solvate, hydrate, tautomer, stereoisomer, derivative, or prodrug thereof, to treat and/or prevent a neurological disease associated with repeat expansions in a subject in need thereof, and/or in a biological sample (e.g., cells or tissue), whereby the method comprises modulating (e.g., inhibiting) RAN protein translation. The present invention provides uses of a compound of Formula (I), (II), (III), (III-A), or (III-B) (e.g., metformin), or a pharmaceutically acceptable salt, solvate, hydrate, tautomer, stereoisomer, derivative, or prodrug thereof, to treat and/or prevent a neurological disease associated with RAN protein accumulation in a subject in need thereof, and/or in a biological sample (e.g., cells or tissue), whereby the method comprises modulating (e.g., inhibiting) RAN protein translation. The present invention provides uses of a compound of Formula (I), (II), (III), (III-A), or (III-B) (e.g., metformin), or a pharmaceutically acceptable salt, solvate, hydrate, tautomer, stereoisomer, derivative, or prodrug thereof, to treat and/or prevent a neurological disease associated with repeat expansions (e.g., poly(GP) and/or poly (PR) RAN proteins) in a subject in need thereof, and/or in a biological sample (e.g., cells or tissue), A subject in need thereof, in certain embodiments, is a patient with expansion mutations or microsatellite repeat expansion mutations.

Pharmaceutical Compositions, Kits, and Administration

The present disclosure also provides pharmaceutical compositions comprising a compound of Formula (I), (II), (III), (III-A), or (III-B) (e.g., metformin) and optionally a pharmaceutically acceptable excipient. In certain embodiments, the pharmaceutical composition comprises a compound of Formula (I), (II), (III), (III-A), or (III-B) (e.g., metformin), or a pharmaceutically acceptable salt thereof, and a pharmaceutically acceptable excipient.

In certain embodiments, a compound of Formula (I), (II), (III), (III-A), or (III-B) (e.g., metformin) is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective in reducing repeat expansions. In certain embodiments, a therapeutically effective amount is an amount effective in reducing the transcription of RNAs that produce RAN proteins. In certain embodiments, a therapeutically effective amount is an amount effective in reducing the translation of RAN proteins. In certain embodiments, a therapeutically effective amount is an amount effective in reducing the level of one or more RAN proteins in a subject. In certain embodiments, a therapeutically effective amount is an amount effective for treating a neurological disease associated with repeat expansions. In certain embodiments, a therapeutically effective amount is an amount effective in reducing the level of one or more RAN proteins and treating a neurological disease associated with repeat expansions. In certain embodiments, a therapeutically effective amount is an amount effective in reducing the level of one or more RAN proteins and treating a neurological disease associated with RAN protein accumulation. In certain embodiments, a therapeutically effective amount is an amount effective in reducing the accumulation of RAN proteins.

In certain embodiments, the effective amount is an amount effective in reducing the level of RAN proteins by at least 10%, at least 20%, at least 30%, at least 40%, at least 50%, at least 60%, at least 70%, at least 80%, at least 90%, at least 95%, or at least 98%. In certain embodiments, the effective amount is an amount effective in reducing the translation of RAN proteins by at least 10%, at least 20%, at least 30%, at least 40%, at least 50%, at least 60%, at least 70%, at least 80%, at least 90%, at least 95%, or at least 98%.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof. The exemplary liquid dosage forms in certain embodiments are formulated for case of swallowing, or for administration via feeding tube.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

A compound of Formula (I), (II), (III), (III-A), or (III-B) (e.g., metformin) provided herein is typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

A compound of Formula (I), (II), (III), (III-A), or (III-B) (e.g., metformin) and compositions thereof provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound of Formula (I), (II), (III), (III-A), or (III-B) (e.g., metformin) required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, eight months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

In one aspect, the method comprises administering to the subject a therapeutically effective amount of a compound of Formula (I):

(I)

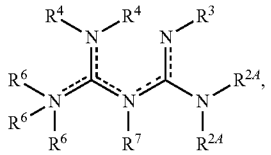

or a pharmaceutically acceptable salt, co-crystal, tautomer, stereoisomer, solvate, hydrate, polymorph, isotopically enriched derivative, or prodrug thereof, wherein:

each instance of ⎓ is a single bond or double bond, as valency permits;

each instance of $R^{2A}$ is independently hydrogen, optionally substituted acyl, optionally substituted alkyl, or a nitrogen protecting group;

$R^3$ is hydrogen, optionally substituted alkyl, or a nitrogen protecting group;

each instance of $R^4$ is independently hydrogen, optionally substituted alkyl, or a nitrogen protecting group, or absent, as valency permits; or, optionally, one instance of $R^4$ is taken together with $R^3$ and the intervening atoms to form an optionally substituted 5 to 7-membered heterocyclic ring;

or optionally, when one instance of $R^4$ is taken together with $R^3$ and the intervening atoms to form an optionally substituted 5 to 7-membered heterocyclic ring, ⎓ connecting the nitrogen of the moiety $—N(R^6)_3$ and the carbon of the moiety $—C(NR^4)_2$ is a double bond, as valency permits;

each instance of $R^6$ is independently hydrogen, optionally substituted alkyl, a nitrogen protecting group, or absent, as valency permits; and $R^7$ is hydrogen, optionally substituted alkyl, a nitrogen protecting group or absent, as valency permits.

In certain embodiments, the compound of Formula (I) is of Formula (I-A):

(I-A)

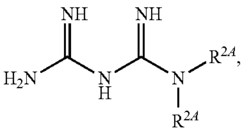

or a pharmaceutically acceptable salt, co-crystal, tautomer, stereoisomer, solvate, hydrate, polymorph, isotopically enriched derivative, or prodrug thereof, wherein:

each instance of $R^{2A}$ is independently hydrogen, optionally substituted alkyl, or a nitrogen protecting group.

In one aspect, the method comprises administering to the subject a therapeutically effective amount of metformin:

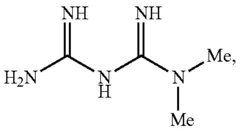

or a pharmaceutically acceptable salt, solvate, hydrate, tautomer, stereoisomer, derivative, or prodrug thereof.

In another aspect, the method comprises administering to the subject a therapeutically effective amount of a compound of Formula (II):

(II)

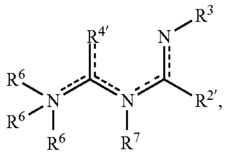

or a pharmaceutically acceptable salt, co-crystal, tautomer, stereoisomer, solvate, hydrate, polymorph, isotopically enriched derivative, or prodrug thereof, wherein:

each instance of ⎓ is a single bond or double bond, as valency permits;

$R^{2'}$ is hydrogen, halogen, or $—N(R^{2A})_2$;

each instance of $R^{2A}$ is independently hydrogen, optionally substituted acyl, optionally substituted alkyl, or a nitrogen protecting group;

$R^3$ is hydrogen, optionally substituted alkyl, or a nitrogen protecting group;

$R^{4'}$ is hydrogen, $—N(R^4)_2$, or

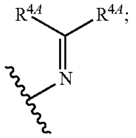

each instance of $R^4$ is independently hydrogen, optionally substituted alkyl, or a nitrogen protecting group, or absent, as valency permits; or, optionally, when $R^{4'}$ is $—N(R^4)_2$, one instance of $R^4$ is taken together with $R^3$ and the intervening atoms to form an optionally substituted 5 to 7-membered heterocyclic ring;

each instance of $R^{4A}$ is independently hydrogen, optionally substituted alkyl, or a nitrogen protecting group;

each instance of $R^6$ is independently hydrogen, optionally substituted alkyl, a nitrogen protecting group, or absent, as valency permits; and $R^7$ is hydrogen, optionally substituted alkyl, a nitrogen protecting group, or absent, as valency permits.

In Formulae (I) and (II), each instance of ⎓ is a single bond or a double bond, as valency permits. In certain embodiments, at least one instance of === is a single bond. In certain embodiments, at least one instance of === is a double bond.

Formula (II) includes substituent $R^{2'}$. In certain embodiments, $R^{2'}$ is hydrogen. In certain embodiments, $R^{2'}$ is halogen (e.g., F, Cl, Br, or I). In certain embodiments, $R^{2'}$ is I. In certain embodiments, $R^{2'}$ is —$N(R^{2A})_2$, and each instance of $R^{2A}$ is independently hydrogen, optionally substituted acyl, optionally substituted alkyl, or a nitrogen protecting group (e.g., —$NMe_2$). In certain embodiments, $R^{2'}$ is —$NMe_2$. In certain embodiments, $R^{2'}$ is —$N(R^{2A})_2$, and each instance of $R^{2A}$ is independently hydrogen or optionally substituted alkyl. In certain embodiments, $R^{2'}$ is —$(N^{15})(R^{2A})_2$, and each instance of $R^{2A}$ is independently hydrogen or optionally substituted alkyl. In certain embodiments, $R^{2A}$ is as defined herein.

Formula (I) includes two instances of substituent $R^{2A}$, and Formula (II) includes zero or more instances of substituent $R^{2A}$. In certain embodiments, at least one instance of $R^{2A}$ is hydrogen. In certain embodiments, both instances of $R^{2A}$ are hydrogen. In certain embodiments, at least one instance of $R^{2A}$ is deuterium. In certain embodiments, both instances of $R^{2A}$ are deuterium. In certain embodiments, at least one instance of $R^{2A}$ is optionally substituted acyl (e.g., —C(=O)Me). In certain embodiments, at least one instance of $R^{2A}$ is optionally substituted alkyl (e.g., substituted or unsubstituted $C_{1-6}$ alkyl). In certain embodiments, at least one instance of $R^{2A}$ is optionally substituted $C_{1-6}$ alkyl. In certain embodiments, at least one instance of $R^{2A}$ is substituted $C_{1-6}$ alkyl. In certain embodiments, at least one instance of $R^{2A}$ is unsubstituted $C_{1-6}$ alkyl. In certain embodiments, at least one instance of $R^{2A}$ is unsubstituted methyl. In certain embodiments, two instances of $R^{2A}$ are unsubstituted methyl. In certain embodiments, at least one instance of $R^{2A}$ is unsubstituted methyl or unsubstituted ethyl. In certain embodiments, at least one instance of $R^{2A}$ is optionally substituted methyl. In certain embodiments, at least one instance of $R^{2A}$ is $-CH_2(D)$. In certain embodiments, at least one instance of $R^{2A}$ is unsubstituted methyl. In certain embodiments, at least one instance of $R^{2A}$ is —$CD_3$. In certain embodiments, both instances of $R^{2A}$ are —$CD_3$. In certain embodiments, at least one instance of $R^{2A}$ is unsubstituted ethyl. In certain embodiments, at least one instance of $R^{2A}$ is optionally substituted ethyl. In certain embodiments, at least one instance of $R^{2A}$ is substituted ethyl. In certain embodiments, at least one instance of $R^{2A}$ is of the formula:

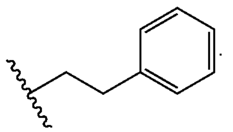

In certain embodiments, at least one instance of $R^{2A}$ is optionally substituted n-propyl. In certain embodiments, at least one instance of $R^{2A}$ is unsubstituted n-propyl. In certain embodiments, at least one instance of $R^{2A}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formulae (I) and (II) include substituent $R^3$. In certain embodiments, $R^3$ is hydrogen. In certain embodiments, at least one instance of $R^3$ is optionally substituted alkyl (e.g., substituted or unsubstituted $C_{1-6}$ alkyl). In certain embodiments, $R^3$ is optionally substituted $C_{1-6}$ alkyl. In certain embodiments, $R^3$ is unsubstituted $C_{1-6}$ alkyl. In certain embodiments, $R^3$ is unsubstituted methyl or unsubstituted ethyl. In certain embodiments, $R^3$ is unsubstituted methyl. In certain embodiments, $R^3$ is optionally substituted methyl. In certain embodiments, $R^3$ is optionally substituted ethyl. In certain embodiments, $R^3$ is unsubstituted ethyl. In certain embodiments, $R^3$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formula (II) includes substituent $R^{4'}$. In certain embodiments, $R^{4'}$ is hydrogen. In certain embodiments, $R^{4'}$ is —$N(R^4)_2$, and each instance of $R^4$ is independently hydrogen, optionally substituted alkyl, or a nitrogen protecting group, or absent, as valency permits. In certain embodiments, $R^{4'}$ is

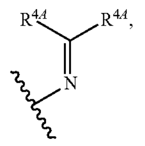

and each instance of $R^4$ is independently hydrogen or optionally substituted alkyl. In certain embodiments, $R^{4'}$ is

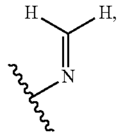

In certain embodiments, $R^4$ is as defined herein.

Formulae (I) and (II) each include one or more instances of substituent $R^4$. In certain embodiments, one instance of $R^4$ is absent. In certain embodiments, Formulae (I) and (II) each include two instances of substituent $R^4$. In certain embodiments, Formulae (I) and (II) each include three instances of substituent $R^4$. In certain embodiments, each instance of $R^4$ is independently hydrogen, optionally substituted alkyl, or a nitrogen protecting group, or absent, as valency permits; or, optionally, one instance of $R^4$ is taken together with $R^3$ and the intervening atoms to form an optionally substituted 5 to 7-membered heterocyclic ring; or optionally, when one instance of $R^4$ is taken together with $R^3$ and the intervening atoms to form an optionally substituted 5 to 7-membered heterocyclic ring, === is a double bond, as valency permits. In certain embodiments, at least one instance of $R^4$ is hydrogen. In certain embodiments, both instances of $R^4$ are hydrogen. In certain embodiments, at least one instance of $R^4$ is deuterium. In certain embodiments, both instances of $R^4$ are deuterium. In certain embodiments, at least one instance of $R^4$ is optionally substituted alkyl (e.g., substituted or unsubstituted $C_{1-6}$ alkyl). In certain embodiments, at least one instance of $R^4$ is optionally substituted $C_{1-6}$ alkyl. In certain embodiments, at least one instance of $R^4$ is unsubstituted $C_{1-6}$ alkyl. In certain embodiments, at least one instance of $R^4$ is unsubstituted methyl or unsubstituted ethyl. In certain embodiments, at least one instance of $R^4$ is optionally substituted methyl. In certain embodiments, at least one instance of $R^4$ is —$CH_2$ (D). In certain embodiments, at least one instance of $R^4$ is unsubstituted methyl. In certain embodiments, two instances of $R^4$ are unsubstituted methyl. In certain embodiments, at least one instance of $R^4$ is —$CD_3$. In certain embodiments, both instances of $R^4$ are —$CD_3$. In certain embodiments, at least one instance of $R^4$ is unsubstituted ethyl. In certain embodiments, at least one instance of $R^4$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, one instance of $R^4$ is taken together with $R^3$ and the intervening atoms to form an optionally substituted 6-membered heterocyclic ring. In certain embodiments, the compound of Formula (I) is of the formula:

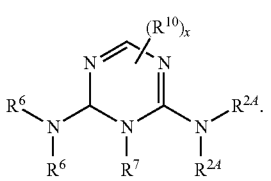

In certain embodiments, when one instance of $R^4$ is taken together with $R^3$ and the intervening atoms to form an optionally substituted 6-membered heterocyclic ring, ═══ connecting the nitrogen of the moiety —$N(R^6)_3$ and the carbon of the moiety —$C(NR^4)_2$ is a double bond. In certain embodiments, the compound of Formula (I) is of the formula:

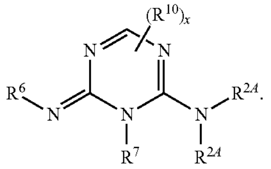

Formulae (I) and (II) each include one or more instances of substituent $R^6$. In certain embodiments, one instance of $R^6$ is absent. In certain embodiments, Formulae (I) and (II) each include two instances of substituent $R^6$. In certain embodiments, Formulae (I) and (II) each include three instances of substituent $R^6$. In certain embodiments, each instance of $R^6$ is independently hydrogen, optionally substituted alkyl, a nitrogen protecting group, or absent, as valency permits. In certain embodiments, at least one instance of $R^6$ is hydrogen. In certain embodiments, two instances of $R^6$ are hydrogen. In certain embodiments, at least one instance of $R^6$ is deuterium. In certain embodiments, two instances of $R^6$ are deuterium. In certain embodiments, at least one instance of $R^6$ is optionally substituted alkyl (e.g., substituted or unsubstituted $C_{1-6}$ alkyl). In certain embodiments, at least one instance of $R^6$ is optionally substituted $C_{1-6}$ alkyl. In certain embodiments, two instances of $R^6$ are optionally substituted $C_{1-6}$ alkyl. In certain embodiments, three instances of $R^6$ are optionally substituted $C_{1-6}$ alkyl, and the moiety:

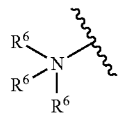

is of the formula:

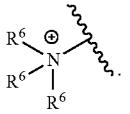

In certain embodiments, at least one instance of $R^6$ is unsubstituted $C_{1-6}$ alkyl. In certain embodiments, at least one instance of $R^6$ is unsubstituted methyl or unsubstituted ethyl. In certain embodiments, at least one instance of $R^6$ is optionally substituted methyl. In certain embodiments, at least one instance of $R^6$ is —$CH_2(D)$. In certain embodiments, at least one instance of $R^6$ is unsubstituted methyl. In certain embodiments, two instances of $R^6$ are unsubstituted methyl. In certain embodiments, at least one instance of $R^6$ is —(C-11)$H_3$ or —(C-13)$H_3$. In certain embodiments, at least one instance of $R^6$ is —(C-11)$H_3$. In certain embodiments, at least one instance of $R^6$ is —(C-13)$H_3$. In certain embodiments, at least one instance of $R^6$ is —$CD_3$. In certain embodiments, both instances of $R^6$ are —$CD_3$. In certain embodiments, at least one instance of $R^6$ is unsubstituted ethyl. In certain embodiments, at least one instance of $R^6$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formulae (I) and (II) each include substituent $R^7$. In certain embodiments, $R^7$ is independently hydrogen, optionally substituted alkyl, a nitrogen protecting group, or absent, as valency permits. In certain embodiments, $R^7$ is absent. In certain embodiments, $R^7$ is hydrogen. In certain embodiments, $R^7$ is deuterium. In certain embodiments, $R^7$ is optionally substituted alkyl (e.g., substituted or unsubstituted $C_{1-6}$ alkyl). In certain embodiments, $R^7$ is optionally substituted $C_{1-6}$ alkyl. In certain embodiments, $R^7$ is unsubstituted $C_{1-6}$ alkyl. In certain embodiments, $R^7$ is unsubstituted methyl or unsubstituted ethyl. In certain embodiments, $R^7$ is optionally substituted methyl. In certain embodiments, $R^7$ is —$CH_2(D)$. In certain embodiments, $R^7$ is unsubstituted methyl. In certain embodiments, $R^7$ is —$CD_3$. In certain embodiments, $R^7$ is unsubstituted ethyl. In certain embodiments, $R^7$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, the compound of Formula (I) is of the formula:

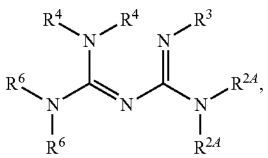

-continued

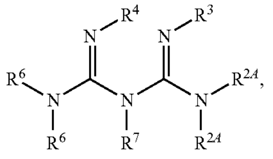

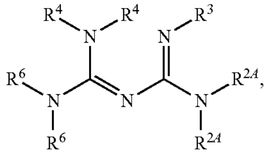

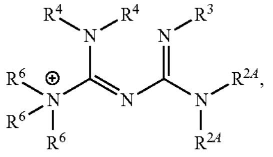

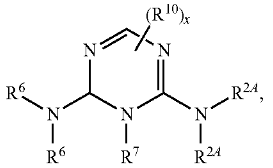

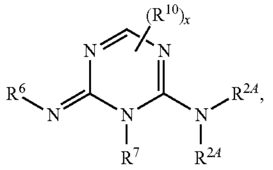

or a pharmaceutically acceptable salt, co-crystal, tautomer, stereoisomer, solvate, hydrate, polymorph, isotopically enriched derivative, or prodrug thereof, wherein:

x is 0 or 1;

$R^{10}$ is halogen, optionally substituted alkyl, —$NH_2$, —NH (optionally substituted alkyl), or —N(optionally substituted alkyl)$_2$.

In certain embodiments, the compound of Formula (I) is of the formula:

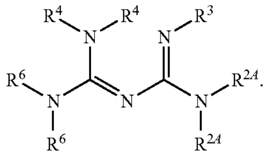

In certain embodiments, the compound of Formula (I) is of the formula:

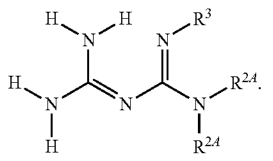

In certain embodiments, the compound of Formula (I) is of the formula:

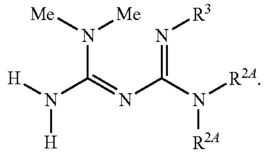

In certain embodiments, the compound of Formula (I) is of the formula:

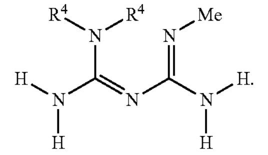

In certain embodiments, the compound of Formula (I) is of the formula:

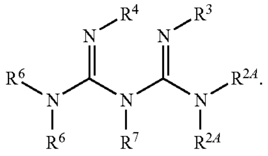

In certain embodiments, the compound of Formula (I) is of the formula:

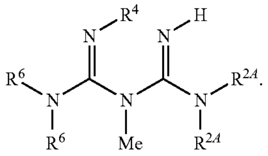

In certain embodiments, the compound of Formula (I) is of the formula:

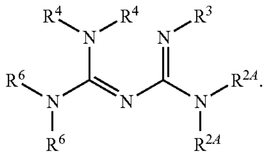

In certain embodiments, the compound of Formula (I) is of the formula:

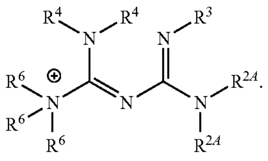

In certain embodiments, the compound of Formula (I) is of the formula:

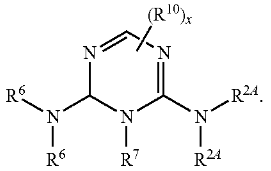

In certain embodiments, the compound of Formula (I) is of the formula:

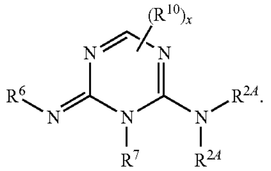

In certain embodiments, the compound of Formula (II) is of the formula:

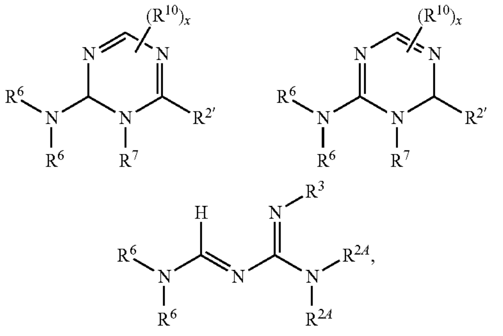

or a pharmaceutically acceptable salt, co-crystal, tautomer, stereoisomer, solvate, hydrate, polymorph, isotopically enriched derivative, or prodrug thereof, wherein:

x is 0 or 1; and $R^{10}$ is halogen, optionally substituted alkyl, —$NH_2$, —NH (optionally substituted alkyl), or —N(optionally substituted alkyl)$_2$.

In certain embodiments, the compound of Formula (II) is of the formula:

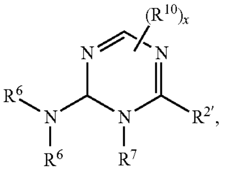

or a pharmaceutically acceptable salt thereof. In certain embodiments, the compound of Formula (II) is of the formula:

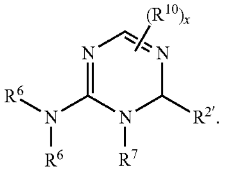

In certain embodiments, the compound of Formula (II) is of the formula:

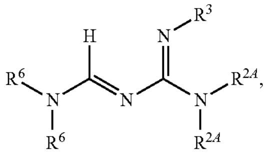

or a pharmaceutically acceptable salt thereof. In certain embodiments, the compound of Formula (II) is of the formula:

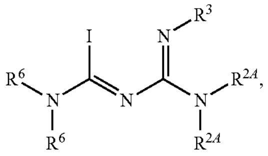

or a pharmaceutically acceptable salt thereof.

In certain embodiments, Formulae (I) and (II) include zero or more instances of substituent $R^{10}$. In certain embodiments, x is 0. In certain embodiments, x is 1. In certain embodiments, at least one instance of $R^{10}$ is halogen (e.g., F, Cl, Br, or I). In certain embodiments, at least one instance of $R^{10}$ is I. In certain embodiments, at least one instance of $R^{10}$ is optionally substituted alkyl (e.g., substituted or unsubstituted $C_{1-6}$ alkyl). In certain embodiments, at least one instance of $R^{10}$ is optionally substituted $C_{1-6}$ alkyl. In certain embodiments, at least one instance of $R^{10}$ is unsubstituted $C_{1-6}$ alkyl. In certain embodiments, at least one instance of $R^{10}$ is unsubstituted methyl or unsubstituted ethyl. In certain embodiments, at least one instance of $R^{10}$ is unsubstituted methyl. In certain embodiments, at least one instance of $R^{10}$ is optionally substituted methyl. In certain embodiments, at least one instance of $R^{10}$ is optionally substituted ethyl. In certain embodiments, at least one instance of $R^{10}$ is unsubstituted ethyl. In certain embodiments, at least one instance of $R^{10}$ is —$NH_2$. In certain embodiments, at least one instance of $R^{10}$ is —N(optionally substituted alkyl)$_2$ (e.g., —N (substituted or unsubstituted $C_{1-6}$ alkyl)$_2$). In certain embodiments, at least one instance of $R^{10}$ is —NH (optionally substituted alkyl)$_2$ (e.g., —NH (substituted or unsubstituted $C_{1-6}$ alkyl).

In certain embodiments, a compound of Formula (I) or (II) is of the formula:

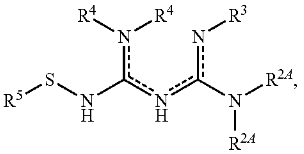

-continued

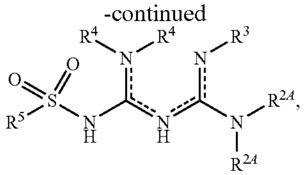

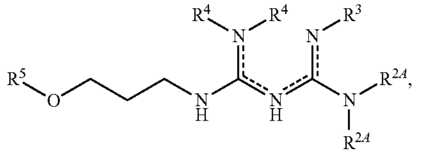

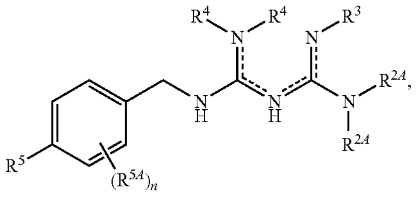

or

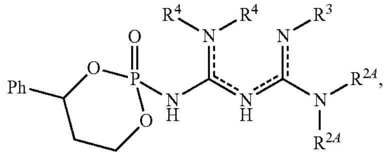

wherein:

- $R^5$ is optionally substituted acyl, unsubstituted alkyl, unsubstituted carbocyclyl, or optionally substituted aryl;
- each instance of $R^{5A}$ is independently —O(optionally substituted alkyl), —OH, —$NH_2$, —NH (optionally substituted alkyl), or —N(optionally substituted alkyl)$_2$; and n is 0, 1, 2, 3, or 4.

In certain embodiments, $R^5$ is optionally substituted acyl, unsubstituted alkyl, unsubstituted carbocyclyl, or optionally substituted aryl. In certain embodiments, $R^5$ is optionally substituted acyl (e.g., —C(═O)Me). In certain embodiments, $R^5$ is unsubstituted alkyl (e.g., unsubstituted $C_{1-6}$ alkyl). In certain embodiments, $R^5$ is unsubstituted carbocyclyl (e.g., substituted or unsubstituted, 3- to 7-membered, monocyclic carbocyclyl comprising zero, one, or two double bonds in the carbocyclic ring system). In certain embodiments, $R^5$ is unsubstituted cyclohexyl. In certain embodiments, $R^5$ is optionally substituted aryl. In certain embodiments, $R^5$ is optionally substituted phenyl. In certain embodiments, $R^5$ is unsubstituted phenyl. In certain embodiments, $R^5$ is optionally substituted benzyl. In certain embodiments, $R^5$ is unsubstituted benzyl.

In certain embodiments, there are zero or more instances of $R^{5A}$. In certain embodiments, n is 0. In certain embodiments, n is 1. In certain embodiments, n is 2. In certain embodiments, n is 3. In certain embodiments, n is 4. In certain embodiments, each instance of $R^{5A}$ is independently —O(optionally substituted alkyl), —OH, —$NH_2$, or —N(optionally substituted alkyl)$_2$. In certain embodiments, at least one instance of $R^{5A}$ is —O(optionally substituted alkyl) (e.g., —O(optionally substituted $C_{1-6}$ alkyl)). In certain embodiments, at least one instance of $R^{5A}$ is —OMe. In certain embodiments, at least one instance of $R^{5A}$ is —OH. In certain embodiments, at least one instance of $R^{5A}$ is —$NH_2$. In certain embodiments, at least one instance of $R^{5A}$ is —N(optionally substituted alkyl)$_2$ (e.g., —N(optionally substituted $C_{1-6}$ alkyl)$_2$). In certain embodiments, at least one instance of $R^{5A}$ is —$NMe_2$. In certain embodiments, at least one instance of $R^{5A}$ is —NH (optionally substituted alkyl).

In certain embodiments, a compound of Formulae (I) or (II) is of the formula:

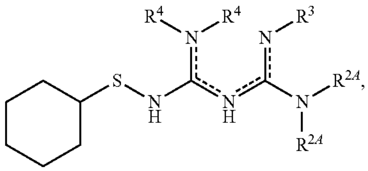

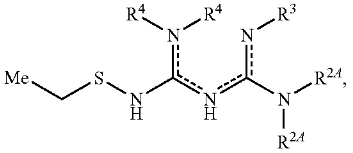

or

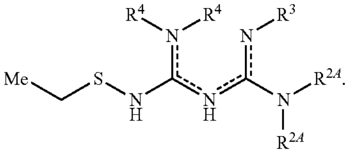

In certain embodiments, in compounds described herein, at least one hydrogen atom is deuterium. In certain embodiments, in compounds described herein, at least one carbon atom is C-11. In certain embodiments, in compounds described herein, at least one carbon atom is C-13. In certain embodiments, in compounds described herein, at least one nitrogen atom is N-15. In certain embodiments, a compound of Formulae (I) or (II) is of the formula:

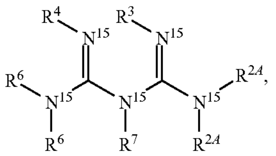

and at least one carbon atom is C-13.

In certain embodiments, the compound of Formula (I) is of the formula:

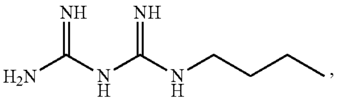

(buformin)

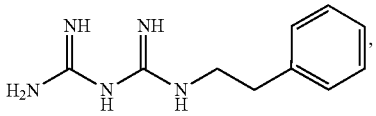

(phenformin)

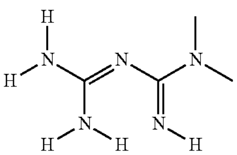

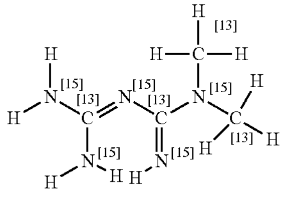

-continued
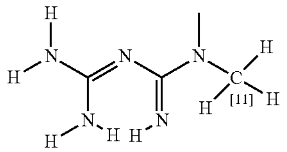
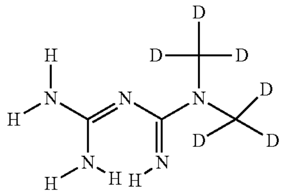
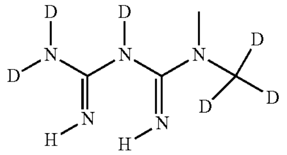
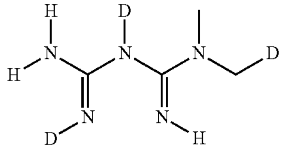
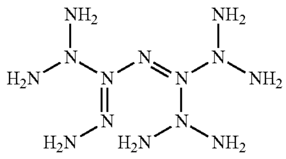
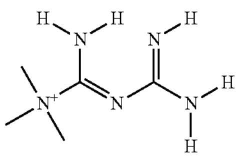
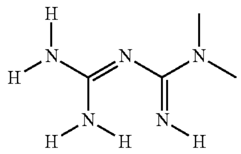
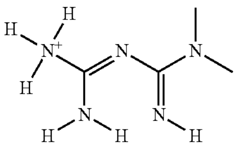
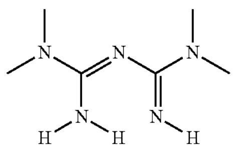
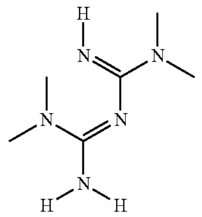
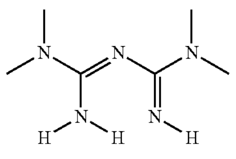
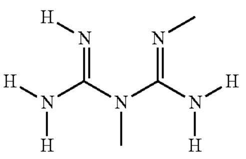
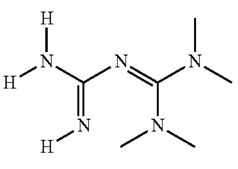
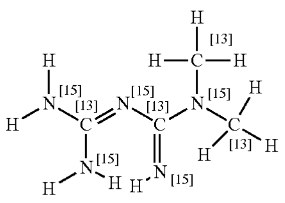
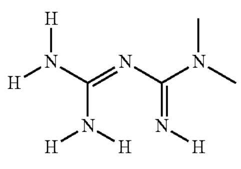
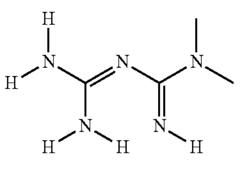
-continued
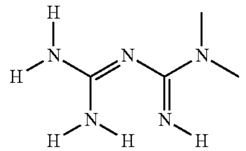
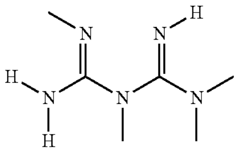
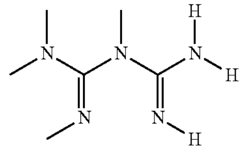
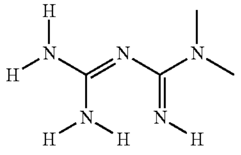
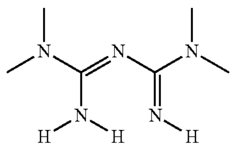
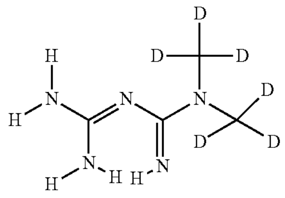
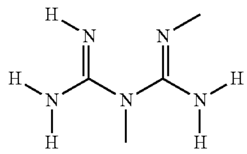
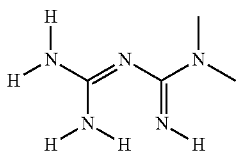
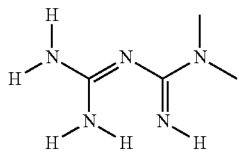
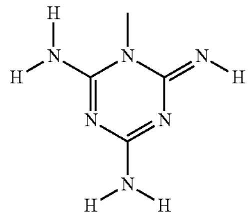
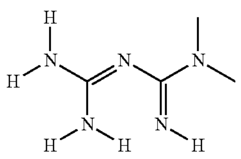
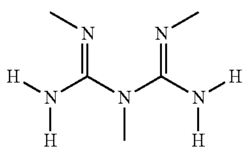
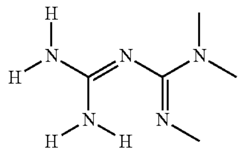
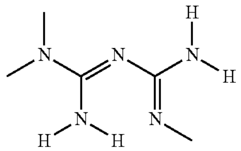
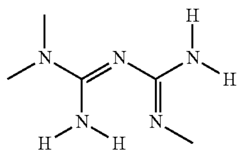
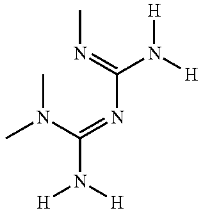
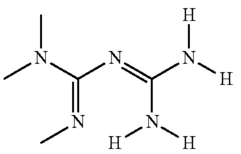
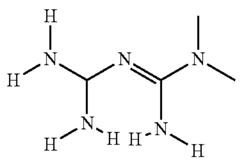
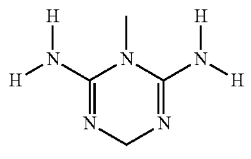
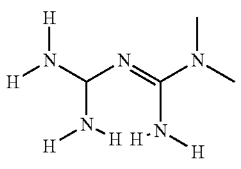

-continued

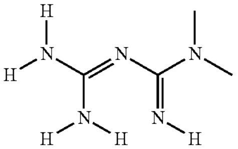

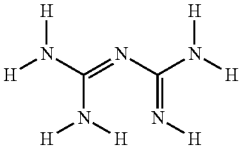

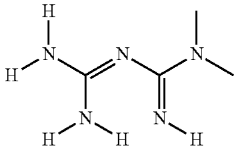

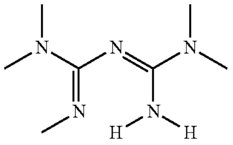

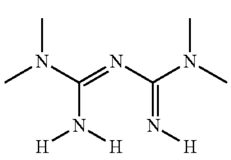

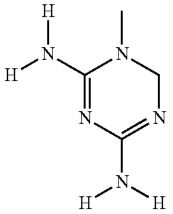

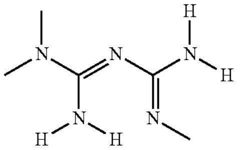

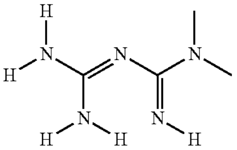

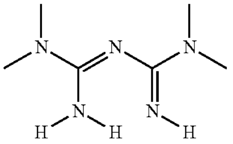

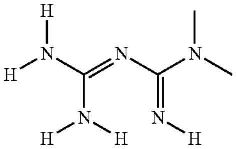

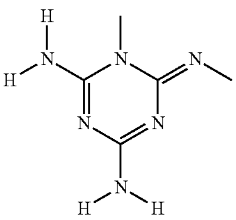

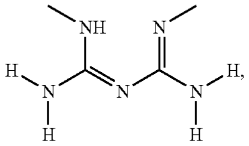

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

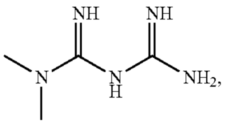

(metformin)

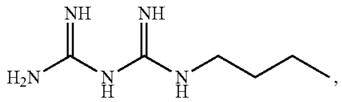

(buformin)

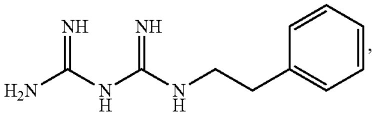

(phenformin)

or a pharmaceutically acceptable salt, co-crystal, tautomer, stereoisomer, solvate, hydrate, polymorph, isotopically enriched derivative, or prodrug thereof. In certain embodiments, the compound of Formula (I) is of the formula:

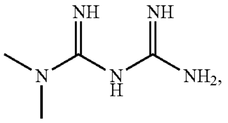

(metformin)

or a pharmaceutically acceptable salt thereof. In certain embodiments, the compound of Formula (I) is of the formula:

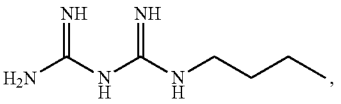

(buformin)

or a pharmaceutically acceptable salt thereof. In certain embodiments, the compound of Formula (I) is of the formula:

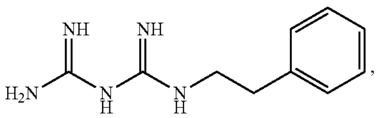

(phenformin)

or a pharmaceutically acceptable salt thereof.

In certain embodiments, the compound of Formula (II) is of the formula:

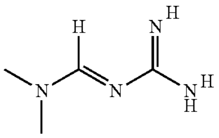

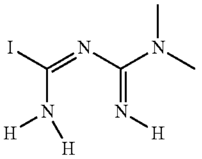

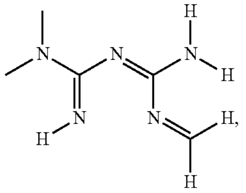

or a pharmaceutically acceptable salt, co-crystal, tautomer, stereoisomer, solvate, hydrate, polymorph, isotopically enriched derivative, or prodrug thereof.

In another aspect, the method comprises administering to the subject a therapeutically effective amount of a compound of Formula (III), (III-A), or (III-B):

(III)

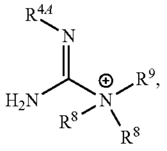

or

-continued (III-A)

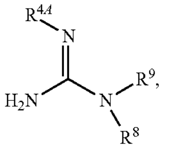

(III-B)

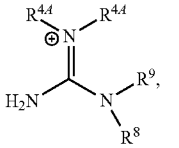

or a pharmaceutically acceptable salt, co-crystal, tautomer, stereoisomer, solvate, hydrate, polymorph, isotopically enriched derivative, or prodrug thereof, wherein:

each instance of $R^{4A}$ is independently hydrogen, optionally substituted alkyl, a nitrogen protecting group, or —CN;

each instance of $R^8$ is independently hydrogen, optionally substituted alkyl, or a nitrogen protecting group; and $R^9$ is hydrogen, optionally substituted alkyl, —CN, or a nitrogen protecting group.

Formulae (III), (III-A), and (III-B) each include substituent $R^{4A}$. In certain embodiments, $R^{4A}$ is as described herein. In certain embodiments, each instance of $R^{4A}$ is independently hydrogen, optionally substituted alkyl, a nitrogen protecting group, or —CN. In certain embodiments, at least one instance of $R^{4A}$ is hydrogen. In certain embodiments, two instances of $R^{4A}$ are hydrogen. In certain embodiments, at least one instance of $R^{4A}$ is optionally substituted alkyl (e.g., substituted or unsubstituted $C_{1-6}$ alkyl). In certain embodiments, at least one instance of $R^{4A}$ is optionally substituted $C_{1-6}$ alkyl. In certain embodiments, two instances of $R^{4A}$ are optionally substituted $C_{1-6}$ alkyl. In certain embodiments, at least one instance of $R^{4A}$ is unsubstituted $C_{1-6}$ alkyl. In certain embodiments, at least one instance of $R^{4A}$ is unsubstituted methyl or unsubstituted ethyl. In certain embodiments, at least one instance of $R^{4A}$ is optionally substituted methyl. In certain embodiments, at least one instance of $R^{4A}$ is unsubstituted methyl. In certain embodiments, at least one instance of $R^{4A}$ is unsubstituted ethyl. In certain embodiments, at least one instance of $R^{4A}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, at least one instance of $R^{4A}$ is —CN.

Formulae (III), (III-A), and (III-B) each include one or more instances of substituent $R^8$. In certain embodiments, each instance of $R^8$ is independently hydrogen, optionally substituted alkyl, or a nitrogen protecting group. In certain embodiments, at least one instance of $R^8$ is hydrogen. In certain embodiments, two instances of $R^8$ are hydrogen. In certain embodiments, at least one instance of $R^8$ is optionally substituted alkyl (e.g., substituted or unsubstituted $C_{1-6}$ alkyl). In certain embodiments, at least one instance of $R^8$ is optionally substituted $C_{1-6}$ alkyl. In certain embodiments, two instances of $R^8$ are optionally substituted $C_{1-6}$ alkyl. In certain embodiments, at least one instance of $R^8$ is unsubstituted $C_{1-6}$ alkyl. In certain embodiments, at least one instance of $R^8$ is unsubstituted methyl or unsubstituted ethyl. In certain embodiments, at least one instance of $R^8$ is optionally substituted methyl. In certain embodiments, at least one instance of $R^8$ is unsubstituted methyl. In certain embodiments, at least one instance of $R^8$ is unsubstituted ethyl. In certain embodiments, at least one instance of $R^8$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formulae (III), (III-A), and (III-B) each include substituent $R^9$. In certain embodiments, $R^9$ is hydrogen, optionally substituted alkyl, —CN, or a nitrogen protecting group. In certain embodiments, $R^9$ is hydrogen. In certain embodiments, $R^9$ is optionally substituted alkyl (e.g., substituted or unsubstituted $C_{1-6}$ alkyl). In certain embodiments, $R^9$ is optionally substituted $C_{1-6}$ alkyl. In certain embodiments, $R^9$ is unsubstituted $C_{1-6}$ alkyl. In certain embodiments, $R^9$ is unsubstituted methyl or unsubstituted ethyl. In certain embodiments, $R^9$ is optionally substituted methyl. In certain embodiments, $R^9$ is unsubstituted methyl. In certain embodiments, $R^9$ is unsubstituted ethyl. In certain embodiments, $R^9$ is —CN. In certain embodiments, $R^9$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, the compound of Formula (III), (III-A), or (III-B) is of the formula:

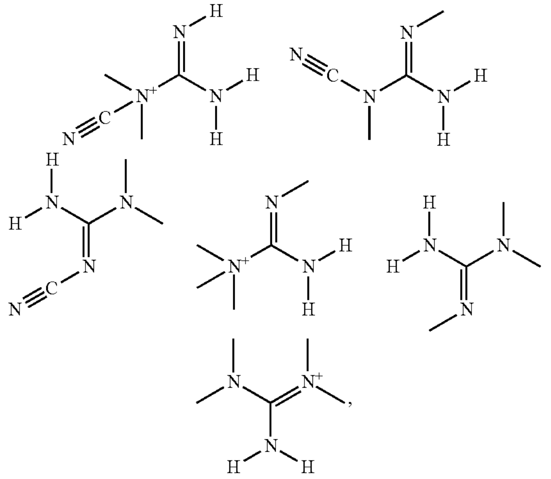

or a pharmaceutically acceptable salt, co-crystal, tautomer, stereoisomer, solvate, hydrate, polymorph, isotopically enriched derivative, or prodrug thereof.

In certain embodiments, provided are methods of using a compound of Formula (I), (II), (III), (III-A), or (III-B), or a pharmaceutically acceptable salt thereof. In certain embodiments, a compound of Formula (I), (II), (III), (III-A), or (III-B) (e.g., metformin) is formulated as a tablet with hydrochloride. In certain embodiments, a compound of Formula (I), (II), (III), (III-A), or (III-B) (e.g., metformin) is formulated as a tablet with a pharmaceutically acceptable salt derived from a suitable inorganic acid, organic acid, or organic base. In certain embodiments, a compound described herein is formulated as a tablet with hydrobromic acid. In certain embodiments, a compound described herein is formulated as a tablet with phosphoric acid. In certain embodiments, a compound described herein is formulated as a tablet with sulfuric acid. In certain embodiments, a compound described herein is formulated as a tablet with perchloric acid. In certain embodiments, a compound described herein is formulated as a tablet with an organic acid such as acetic acid, oxalic acid, maleic acid, tartaric acid, citric acid, succinic acid, or malonic acid. In certain embodiments, a compound described herein is formulated as a tablet using other methods known in the art such as ion exchange.

In certain embodiments, a compound of Formula (I), (II), (III), (III-A), or (III-B) (e.g., metformin) are formulated as a tablet with HBr. In certain embodiments, metformin is formulated as a metformin hydrochloride tablet. In certain embodiments, a compound of Formula (I), (II), (III), (III-A), or (III-B) (e.g., metformin) is formulated as a metformin hydrochloride extended release tablet. In certain embodiments, metformin is formulated as a metformin succinate or metformin fumurate salt. A compound of Formula (I), (II), (III), (III-A), or (III-B) (e.g., metformin) and compositions thereof, in certain embodiments, is administered via an enteral (e.g., oral) route. In certain embodiments, a compound of Formula (I), (II), (III), (III-A), or (III-B) (e.g., metformin) is administered in doses of 500 mg metformin twice a day or doses of 850 mg metformin once a day. In certain embodiments, a compound of Formula (I), (II), (III), (III-A), or (III-B) (e.g., metformin) is administered in doses of at least 825 mg metformin three times a day. In certain embodiments, a compound of Formula (I), (II), (III), (III-A), or (III-B) (e.g., metformin) is administered in doses of 825 mg metformin three times a day. In certain embodiments, a compound of Formula (I), (II), (III), (III-A), or (III-B) (e.g., metformin) is administered in doses of 500 mg metformin once a day. In certain embodiments, a compound of Formula (I), (II), (III), (III-A), or (III-B) (e.g., metformin) is administered in doses of 1000 mg once a day. Doses of a compound of Formulae (I), (II), (III), (III-A), or (III-B) (e.g., metformin), in certain embodiments, are given with meals. In certain embodiments, the method comprises administering to the subject a compound of Formula (I), (II), (III), (III-A), or (III-B) (e.g., metformin) over a period between 10 days to 30 days. In certain embodiments, the duration between the first dose and last dose of the multiple doses of a compound of Formula (I), (II), (III), (III-A), or (III-B) (e.g., metformin) is 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In certain embodiments, the duration between the first dose and last dose of the multiple doses of a compound of Formula (I), (II), (III), (III-A), or (III-B) (e.g., metformin) is at least the following number of days: 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In certain embodiments, the duration between the first dose and last dose of the multiple doses of metformin is 1 month, 2 months, 3 months, 4 months, 5 months, 6 months, multiple months, at least one year, multiple years, at least one decade, or multiple decades. In certain embodiments, the doses of a compound of Formula (I), (II), (III), (III-A), or (III-B) (e.g., metformin) are administered indefinitely. In certain embodiments, the doses of metformin are administered over a lifetime of the subject. In certain embodiments, a dose described herein is at least 500 mg, 600 mg, 650 mg, 750 mg, 700 mg, 800 mg, 825 mg, 850 mg, 900 mg, 950 mg, 1000 mg, 1500 mg, 2000 mg, 2500 mg, 3000 mg, 3500 mg, 4000 mg, 5000 mg, 8000 mg, 9000 mg, or 10,000 mg of a compound of Formula (I), (II), (III), (III-A), or (III-B) (e.g., metformin). In certain embodiments, the duration between the first dose and last dose of the multiple doses of a compound of Formula (I), (II), (III), (III-A), or (III-B) (e.g., metformin) is based on the duration required to prevent the accumulation of RAN proteins in a subject. In certain embodiments, the duration between the first dose and last dose of the multiple doses of a compound of Formula (I), (II), (III), (III-A), or (III-B) (e.g., metformin) is based on the duration required to reduce the level of RAN proteins in a subject. In certain embodiments, the multiple doses of a compound of Formula (I), (II), (III), (III-A), or (III-B) (e.g., metformin) are administered as prophylactic treatment to reduce the level of RAN proteins in a subject. The prophylactic treatment is long-term, in certain embodiments. In certain embodiments, the multiple doses of a compound of Formula (I), (II), (III), (III-A), or (III-B) (e.g., metformin) are administered as long-term therapeutic treatment to reduce the level of RAN proteins in a subject. The subject, in certain embodiments, has a microsatellite expansion mutation including but not limited to mutations that cause: C9orf72 ALS or C9orf72 FTD, myotonic dystrophy type 1 (DM1) and myotonic dystrophy type 2 (DM2); spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease (HD); Fragile X Tremor Ataxia Syndrome (FXTAS); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; and Fragile XE syndrome (FRAXE).

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound of Formula (I), (II), (III), (III-A), or (III-B) (e.g., metformin) or compositions thereof, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compounds of Formulae (I), (II), (III), (III-A), and (III-B) (e.g., metformin) or compositions thereof can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., neurological disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In some embodiments, additional pharmaceutical agents include, but are not limited to, cardiovascular agents, anti-diabetic agents, and agents for treating and/or preventing a neurological disease. The additional pharmaceutical agents include, but are not limited to, anti-inflammatory agents or compounds (e.g., turmeric).

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound of Formula (I), (II), (III), (III-A), or (III-B) (e.g., metformin) or compositions thereof described herein. In certain embodiments, the kits are useful for treating a neurological disease) in a subject in need thereof. In certain embodiments, the kits are useful for preventing a neurological disease) in a subject in need thereof. In certain embodiments, the kits are useful for reducing the level of one or more RAN proteins (e.g., reducing the expression of RAN proteins) in a subject, biological sample, tissue, or cell. In certain embodiments, the kits are useful for reducing the accumulation of RAN proteins in a subject, biological sample, tissue, or cell. In certain embodiments, the kits are useful for modulating (e.g., reducing or inhibiting) RAN protein translation in a subject, biological sample, tissue, or cell.

In certain embodiments, a kit described herein further includes instructions for using a compound of Formula (I), (II), (III), (III-A), or (III-B) (e.g., metformin), or pharmaceutical composition thereof, included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., a neurological disease) in a subject in need thereof. In certain embodiments, the kits and instructions provide for preventing a disease (e.g., a neurological disease) in a subject in need thereof. In certain embodiments, the kits and instructions provide for reducing the level of one or more RAN proteins in a subject, biological sample, tissue, or cell. In certain embodiments, the kits and instructions provide for reducing the accumulation of RAN proteins in a subject, biological sample, tissue, or cell. In certain embodiments, the kits and instructions provide for modulating (e.g., reducing or inhibiting) RAN protein translation in a subject, biological sample, tissue, or cell. A kit described herein may include one or more additional pharmaceutical agents described herein as a separate composition.

EXAMPLES

In order that the present disclosure may be more fully understood, the following examples are set forth. The examples described in this application are offered to illustrate the compositions and methods provided herein and are not to be construed in any way as limiting their scope.

Figure 1B:
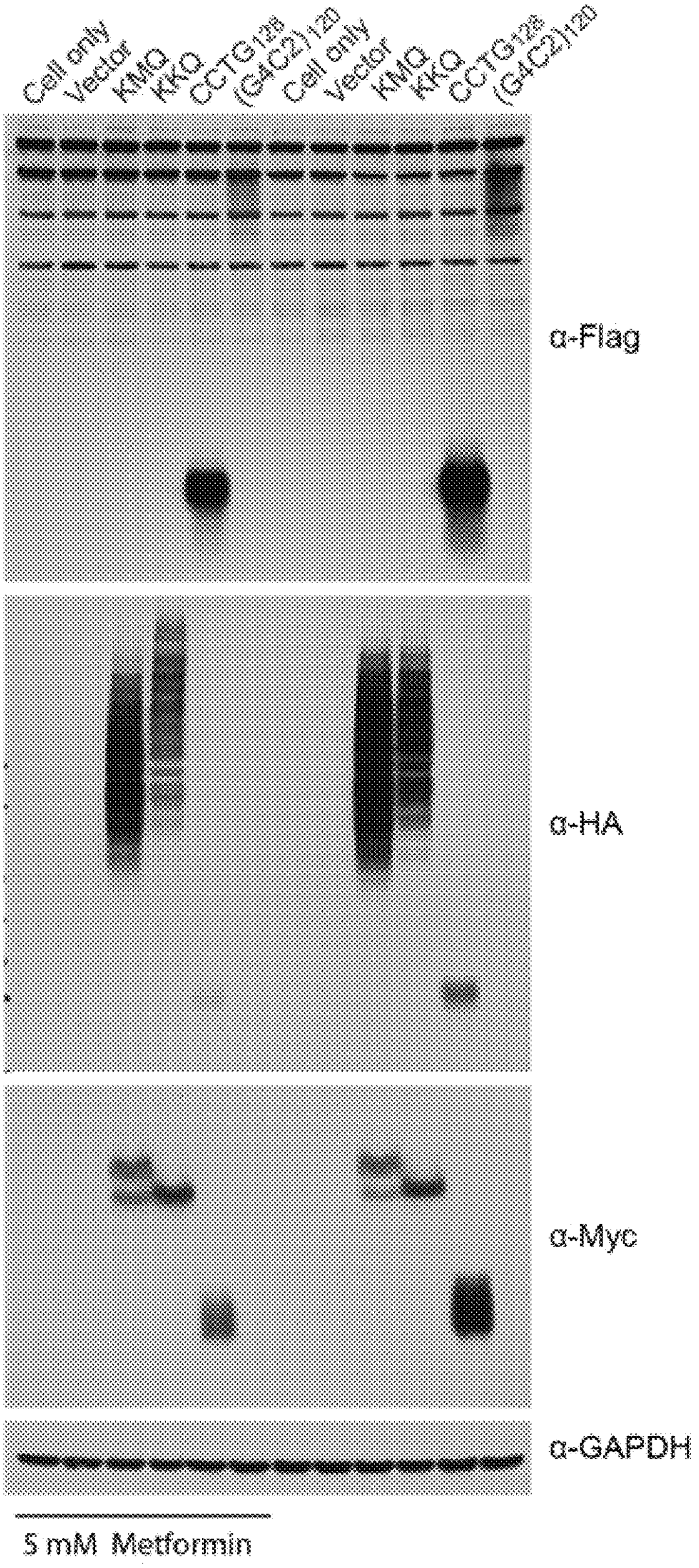

Example 1. Assay of Metformin Effects on HEK293T Cells Transfected with Repeat Expansion Constructs Metformin was evaluated for its effect on RAN protein translation in HEK293T cells that have been transfected with constructs containing CAG, CCTG or GGGGCC repeat expansion motifs. Transfected HEK293T cells were treated with metformin. Protein blots were run on protein lysates from HEK293T cells transfected with various repeat expansion constructs shown in FIG. 1A. In FIG. 1B, the lanes labeled KMQ, show: RAN poly-Ser-Flag, RAN poly-Ala-HA, ATG initiated polyGln-Myc. In FIG. 1B, the lanes labeled KMQ has a methionine encoding ATG immediately 5' to the CAG repeat expansion and located within the polyGln reading frame. The lanes labeled KKQ indicate the KKQ vector contains a CAG expansion without an AUG initiation codon, and indicates: RAN polySer-Flag, RAN polyAla-HA, RAN polyGln-Myc. These constructs contain epitope tags that are incorporated into the C-terminal regions of the ATG-initiated poly-Gln and non-ATG initiated RAN proteins (poly-Gln, poly-Leu-Pro-Ala-Cys and poly-Gly-Pro) which are expressed across these repeat expansions. The lane labeled CCTG expresses the following RAN proteins: RAN polyLPAC-Flag, RAN polyLPAC-HA, RAN polyLPAC-Myc. The lane labeled $G4C_2$ is designed to detect the following RAN proteins: RAN polyGP-Flag, RAN polyGR-HA, RAN polyGA-Myc. The protein blots in FIG. 1B show reduced RAN protein levels of the following RAN proteins of poly-LPAC (poly-Leucine-Proline-Alanine-Cysteine) in all three reading frames, poly-Ala, and poly-GP (poly glycine-proline). FIG. 1B shows that metformin inhibits RAN protein accumulation in cells transfected with exemplary repeat expansion constructs.

Figure 2:
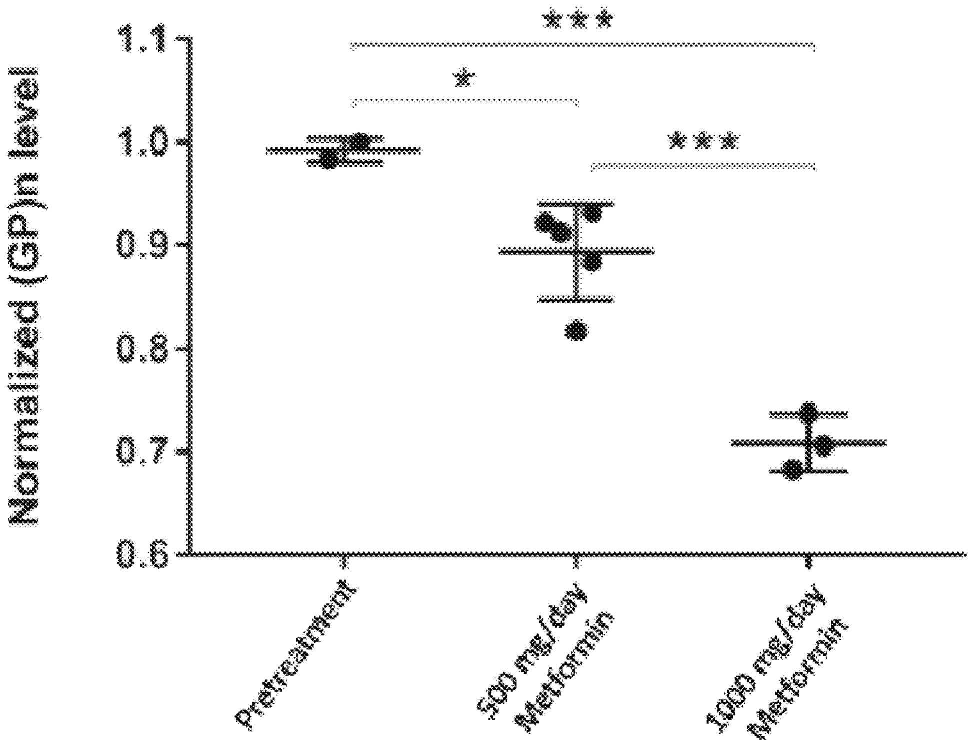
FIG. 2 shows that steady state levels of RAN proteins expressed by the C9ORF72 expansion mutation were reduced in vivo in a human study subject before and after taking metformin (500 mg or 1000 mg per day Metformin Hydrochloride Extended Release Tablets) as prescribed by the subject's physician. Dose-dependent reduction of glycine-proline (GP) RAN protein levels was observed in blood samples taken from a single human subject with a C9ORF72 repeat expansion compared to pretreatment levels. GP levels were measured in protein lysates from leukocytes isolated from peripheral blood and at multiple time points between 10 and 30 days after treatment with 500 or 1000 mg/day of metformin. * $p<0.05$, *** $p<0.001$, after correction for multiple comparisons.

Example 2. In Vivo Evaluation of Metformin Effects on Exemplary RAN Protein Levels Metformin was evaluated for its effect on the steady state levels of glycine-proline (GP) RAN protein detected in vivo in proteins extracted from peripheral blood of a C9ORF72 expansion-positive study subject before and after treatment with metformin C9ORF72. These levels were measured in a human study subject before and after the subject was administered metformin (500 mg or 1000 mg per day Metformin Hydrochloride Extended Release Tablets) at different doses as prescribed by the subject's physician. Dose dependent reduction of glycine-proline (GP) RAN protein levels was observed in blood samples taken from a single human subject with a C9ORF72 repeat expansion compared to pretreatment levels. GP levels were measured in protein lysates from leukocytes isolated from peripheral blood and at multiple time points between 10 and 30 days after treatment with 500 or 1000 mg/day of metformin. *$p<0.05$, *$p<0.001$, after correction for multiple comparisons. FIG. 2** shows that metformin reduces the levels of RAN proteins generated by expression of C9ORF72 in vivo.

Example 3: Evaluation of Metformin Inhibiting RAN Translation Though PKR Pathway and Ameliorating Phenotypes in a C9orf72 Mouse Model This Example describes activation of the PKR pathway by structured RAN-positive repeat expansion RNAs. In some embodiments, the activation leads to increased phospho-cIF2α (p-cIF2α) and increased RAN protein levels. It was observed that inhibition of PKR decreased RAN protein levels in cell culture and a BAC transgenic mouse model of C9orf72 ALS/FTD (C9-BAC). It was also observed that metformin (and certain metformin derivatives, for example buformin and phenformin) inhibits phospho-PKR activation, decreases RAN protein levels and improves phenotypes in C9-BAC mice.

Materials and Methods

Gait analysis. Digital video images of the underside of the mouse were collected with a high-speed video camera from below the transparent belt of a motorized treadmill (DigiGait™ Imaging system, Mouse Specific). Each mouse was allowed to explore the treadmill compartment with the motor speed set to 14 cm/s for 1 min then the motor speed was increased to 24 cm/s for video recording. Only video recordings in which the mouse walked straight ahead with a constant relative position with respect to the camera were used for analysis. Data from each paw was analyzed with DigiGait automated gait analysis software (Mouse Specifics).

Open field analysis. Open field analysis was performed by testing mouse behavior during a 30 min session in a completely dark open chamber (17"×17") (Med Associates). Approximately two hours before the start of analysis, mice were placed in the testing room to allow for acclimation to the room. Mice were then placed in the center of the darkened activity-monitoring chamber. The trace path and center time was recorded and analyzed with Activity Monitor (MED associates, Inc.) software.

Cell Culture and Transfection

HEK293T cells were cultured in DMEM medium supplemented with 10% fetal bovine serum and incubated at 37° C. in a humid atmosphere containing 5% $CO_2$. DNA transfections were performed using Lipofectamine 2000 Reagent (Invitrogen) according to the manufacturer's instructions.

AAV Construction and Preparation

AAV vectors expressing the PKR under the control of the cytomegalovirus enhance/chicken beta actin (CBA) promoter, a woodchuck hepatitis virus post-transcriptional-regulatory element (WPRE), and the bovine growth hormone polyA were generated by Polyethylenimine Linear (PEI, Polysciences) transfection into HEK293T cells. Cells were co-transfected with AAV helper plasmids pDP8.ape to produce recombinant adeno-associated viral (rAAV) vector rAAV2/8.

Intracerebroventricular (ICV) Injection

Neonatal pups were injected within 0-12 hours after birth. The naive pups were covered in aluminum foil and completely surrounded in ice for 3-4 minutes, resulting in the body temperature being lowered to <10° C. The pups were considered completely cryoanesthetized when all movement stops and the skin color changes from pink to purple. 2 μl of virus (1013 viral genomes/ml) was slowly injected into the ventricle using 10 μl syringes (30 degree beveled). After injection pups were allowed to completely recover on a warming blanket and then returned to the home cage.

Immunofluorescence

The subcellular distribution of polymeric proteins was assessed in transfected HEK293T cells by immunofluorescence. Cells were plated on 8 well tissue-culture chambers and transfected with plasmids the next day. Forty-eight hours post-transfection, cells were fixed in 4% paraformaldehyde (PFA) in PBS for 30 min and permeabilized in 0.5% triton X-100 in PBS for 15 min on ice. The cells were blocked in 1% normal goat serum (NGS) in PBS for 30 min. After blocking, the cells were incubated for 1 hour at RT in blocking solution containing the rabbit anti-Myc (Abcam), mouse anti-HA (Covance), mouse anti-Flag (Sigma), rabbit α-GR and rabbit α-GR-CT primary antibodies at a dilution of 1:400. The slides were washed three times in PBS and incubated for 1 hour at RT in blocking solution containing Goat anti-rabbit conjugated to Cy3 (Jackson ImmunoResearch, PA) and goat anti-mouse conjugated to Alexa Fluor 488 (Invitrogen) secondary antibodies at a dilution of 1:200. The slides were washed three times in PBS and mounted with mounting medium containing DAPI (Invitrogen). Immunofluorescence in patient hippocampal tissue was performed on the 6 μm fresh frozen sections. A similar protocol was used as in transfected cells, except 2% NGS was used as blocking buffer and higher dilution of antibodies was used (mouse α-GP 1:1000 and rabbit α-GP-CT 1:5000).

Western Blotting

Transfected cells in each well of a six-well tissue-culture plate were rinsed with PBS and lysed in 300 μL RIPA buffer with protease inhibitor cocktail for 45 min on ice. DNA was sheared by passage through a 21-gauge needle. The cell lysates were centrifuged at 16,000×g for 15 min at 4° C., and the supernatant was collected. The protein concentration of the cell lysate was determined using the protein assay dye reagent (Bio-Rad). Twenty micrograms of protein were separated in a 4-12% NuPAGE Bis-Tris gel (Invitrogen) and transferred to a nitrocellulose membrane (Amersham). The membrane was blocked in 5% dry milk in PBS containing 0.05% Tween-20 (PBS-T) and probed with the anti-Flag (1:2000), anti-Myc (1:1000), anti-HA (1:1000), or rabbit polyclonal antibodies (1:1000) in blocking solution. After the membrane was incubated with anti-rabbit or anti-mouse HRP-conjugated secondary antibody (Amersham), bands were visualized by the ECL plus Western Blotting Detection System (Amersham).

Sequential extraction of patient frontal cortex autopsy tissue was performed as follows: tissue was homogenized in PBS containing 1% Triton-X100, 15 mM $MgCl_2$, 0.2 mg/ml DNase I and protease inhibitor cocktail and centrifuged at 16,000×g for 15 min at 4° C. The supernatant was collected.

The pellet was resuspended in 2% SDS and incubated at room temperature for 1 hour, then centrifuged at 16,000×g for 15 min at 4° C. The supernatant was collected and the 2% SDS insoluble pellet was resuspended in 8% SDS, 62.5 mM Tris-HCl pH 6.8, 10% glycerol, and 20% 2-mercaptoethanol for protein blotting.

Metformin Decreases RAN Translation and Mitigates Repeat-induced PKR Activation

Figure 3A:
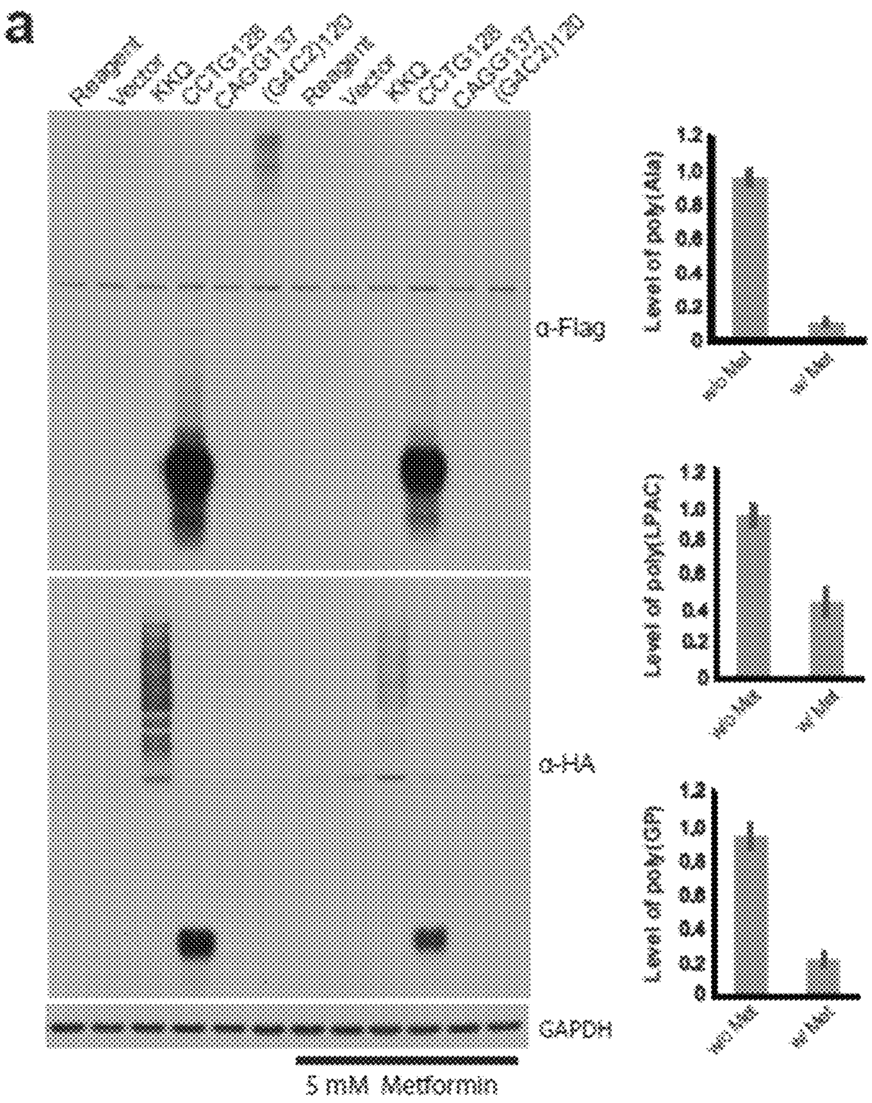
FIGS. 3A-3J show metformin inhibits PKR and reduces RAN proteins and ameliorates disease in C9orf72 ALS/FTD BAC transgenic mice (C9-BAC) mice.
Figure 3B:
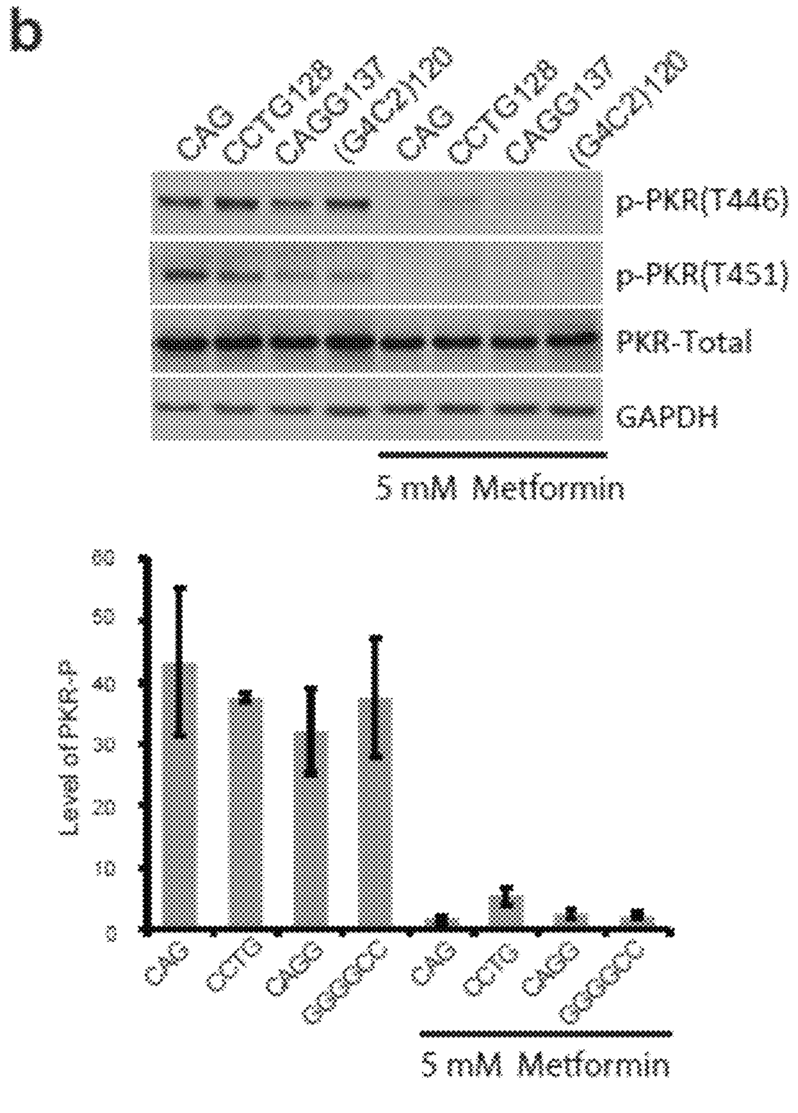
Figure 4:
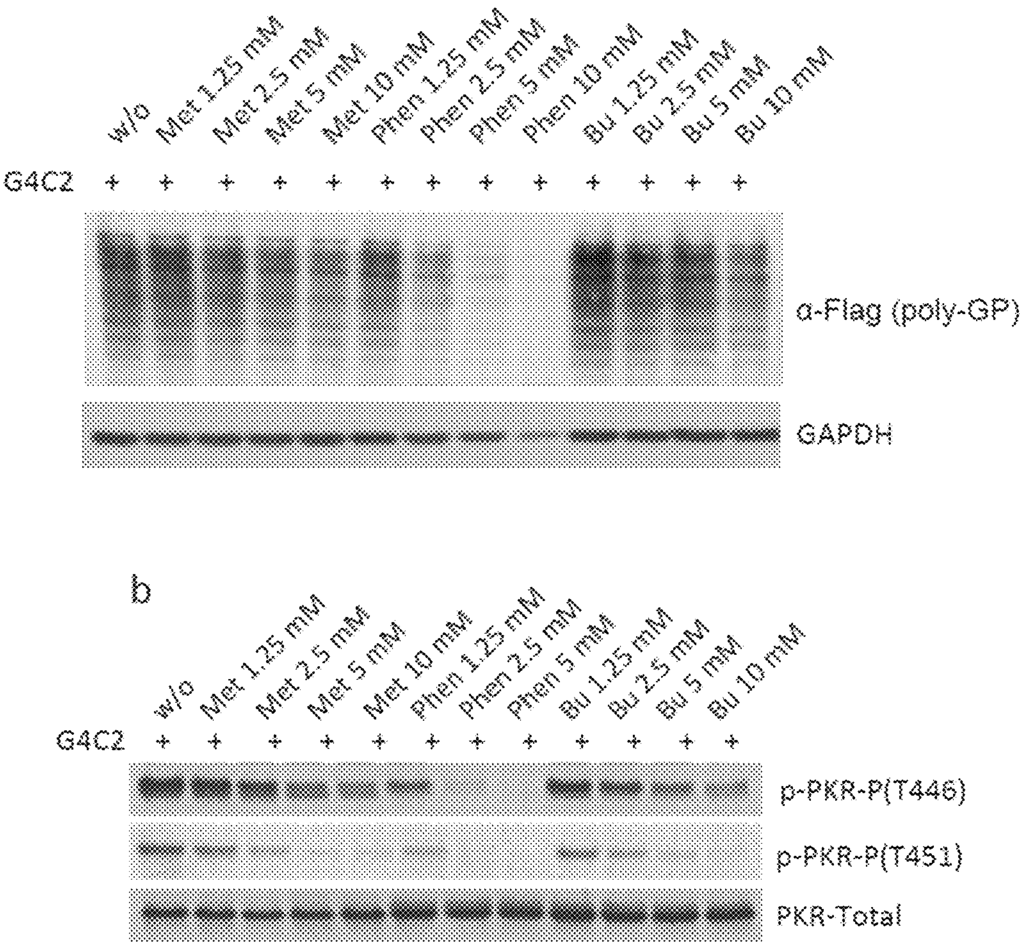
FIG. 4 shows metformin and related drugs phenformin and buformin inhibit PKR and reduce GP RAN protein levels in a dose-dependent manner. Top panel: protein blots showing metformin, phenformin, and buformin reduce RAN GP protein levels in HEK293T cells transiently transfected with G4C2 expansion constructs in a dose dependent manner. Bottom panel: metformin, phenformin, and bufomin reduce levels of p-PKR (T446 and T451) in cells transfected with a G4C2 repeat expansion construct.

It was observed that, in some embodiments, metformin decreases RAN protein levels in cells expressing CAG, CCUG or $G4C_2$ expansion RNAs (FIG. 3A). RAN protein inhibition by metformin is similar to the inhibition with PKR-K296R, indicating that metformin mitigates PKR activation induced by repeat expansion RNAs. Transient transfections of expansion constructs treated with or without metformin were performed. Protein blots indicate that metformin decreases PKR phosphorylation at T446 and T451, sites which have been observed to be required for PKR activation (FIG. 3B). Additionally, metformin and the related drugs phenformin and buformin mediate similar dose-dependent inhibition of $G4C_2$ repeat-expansion induced p-PKR levels and RAN polyGP levels (FIG. 4).

In summary, metformin reduced the levels of several types of RAN proteins in mammalian cells and PKR was identified as a metformin target that inhibits PKR activation and cIF2α phosphorylation.

Metformin Ameliorates Neuropathological and Behavioral Phenotypes in the $C_9$-500 Mouse Model.

Figure 3C:
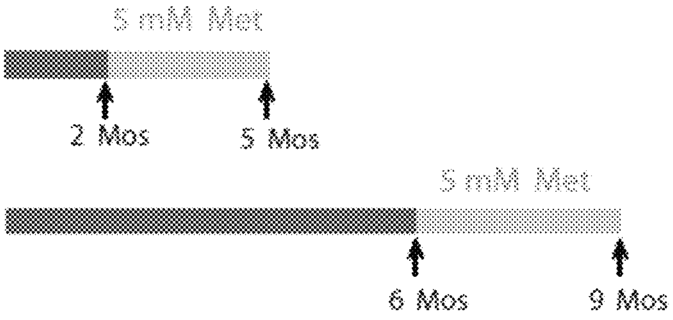
Figure 3D:
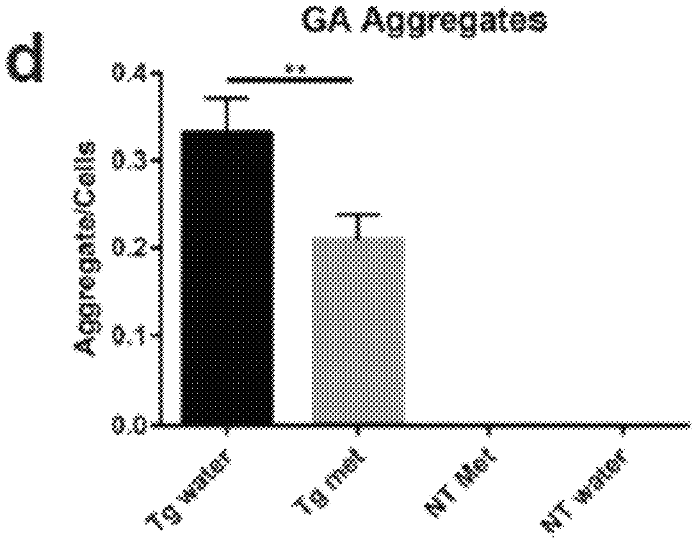
Figure 3E:
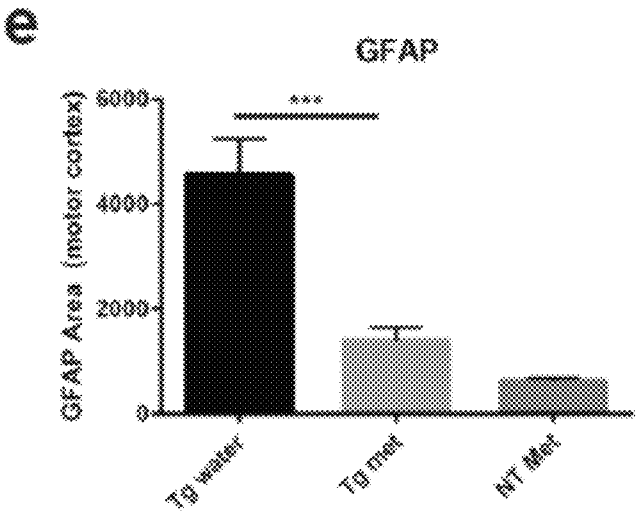
Figure 3F:
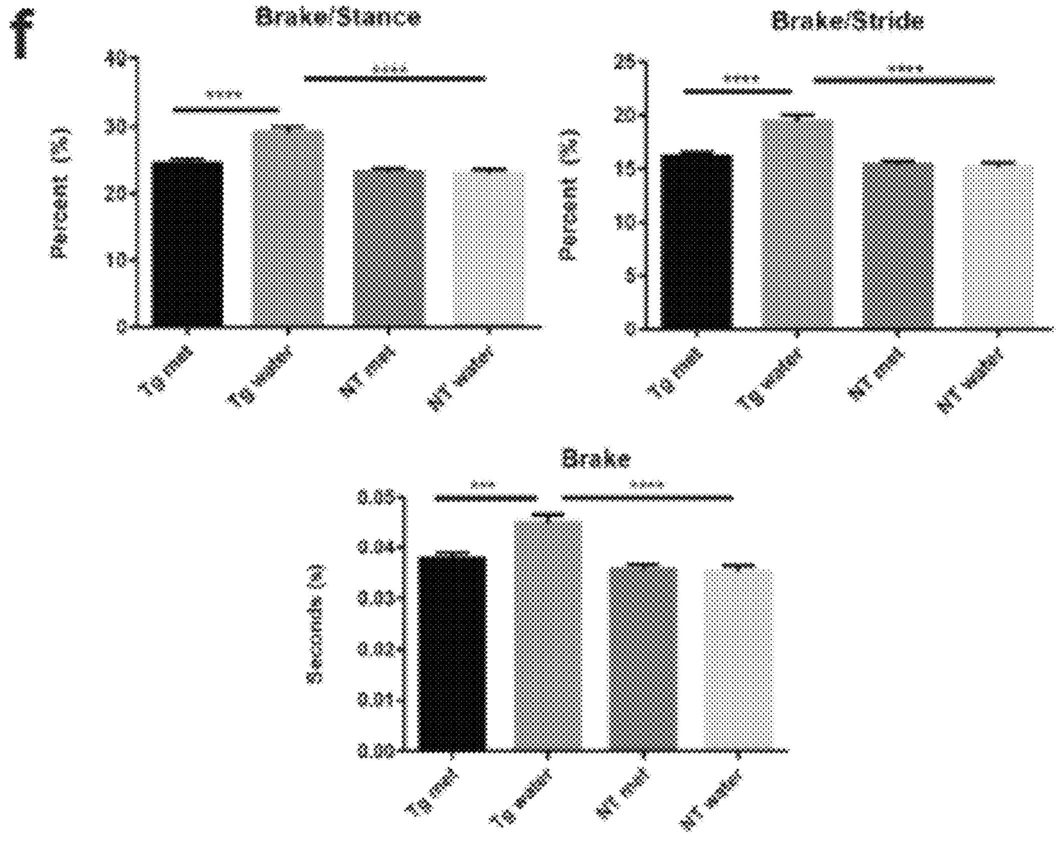
Figure 3G:
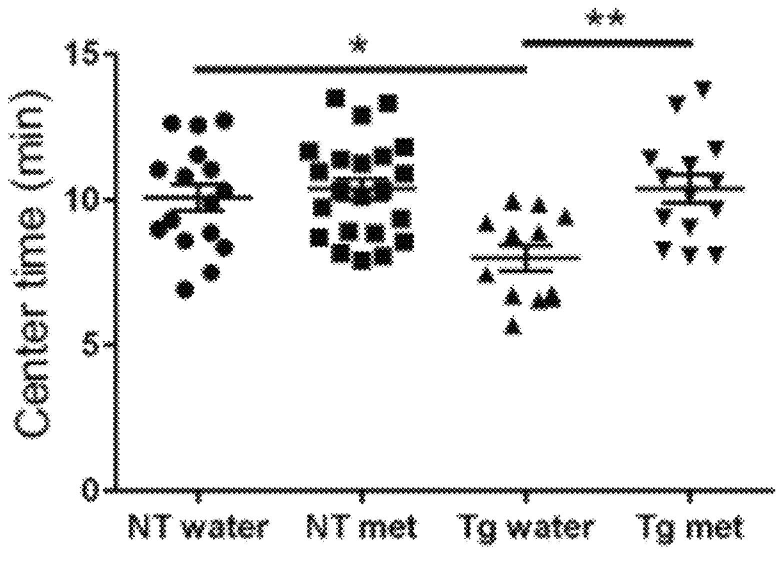

C9orf72 mice, C9-500 BAC and NT mice were treated for 3 months with or without metformin (5 mg/ml) in the drinking water. In Group A animals, treatment began at 2 months of age, before the onset of overt behavioral or pathological phenotypes. In Group B, smaller cohorts of animals (n=8/group) were treated beginning at 6 months, an age at which behavioral phenotypes are evident. A schematic depicting treatment regimens is shown in FIG. 3C. DigiGait analyses of Group A mice at 5 months identified eight DigiGait parameters that differed between untreated C9 and NT cohorts. In C9 metformin treated mice, six of these parameters improved compared to the C9 water treatment group (FIGS. 3E-3G). Similarly, Group A metformin-treated C9 mice showed increased center time by open field testing, compared to untreated C9 mice. These data indicate that this anxiety-like behavior is improved by metformin treatment (FIG. 3G).

Figure 3H:
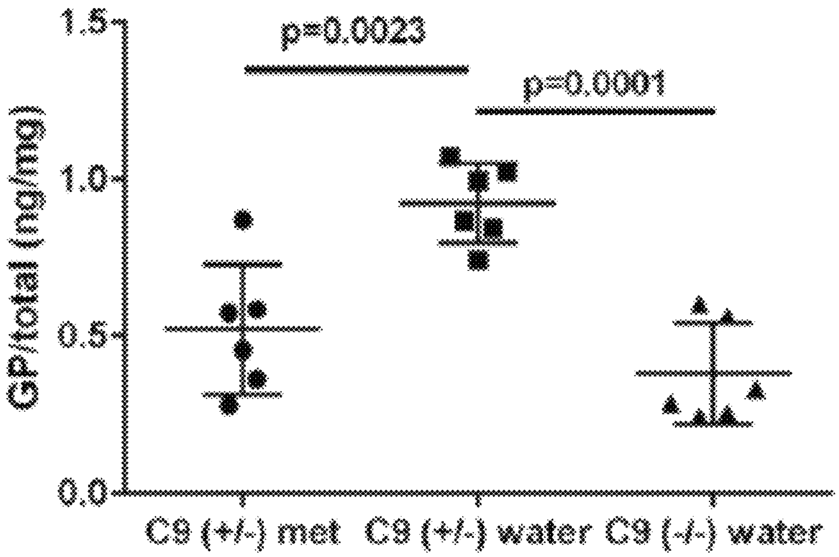
Figure 3I:
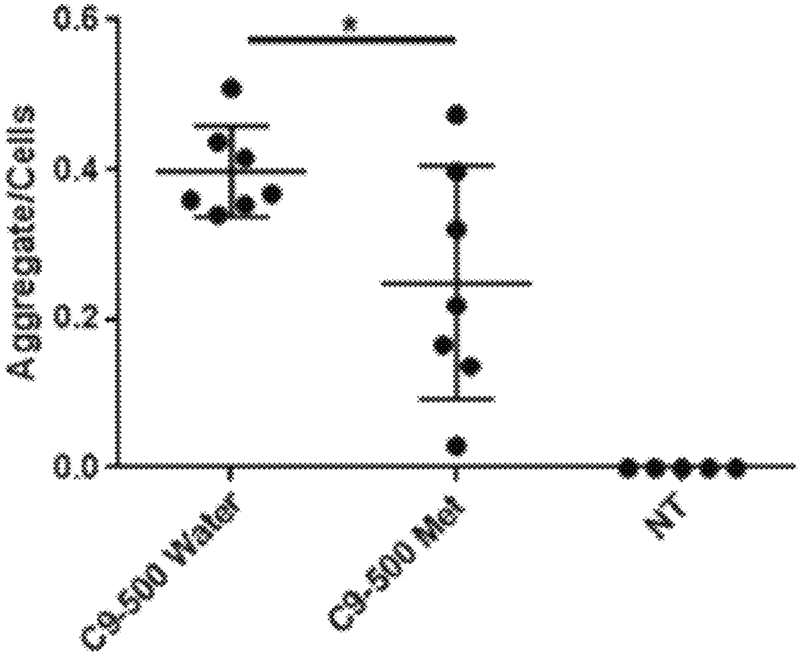

IHC staining of Group A animals for glial fibrillary acidic protein (GFAP), a marker of neuroinflammation previously reported in our C9-BAC mice, was significantly reduced in C9 metformin treated compared to untreated C9 animals (FIG. 3E). Additionally, C9 metformin treated animals showed decreased numbers of GA aggregates in the retrosplenial cortex compared to C9 controls in cohorts that began treatment at presymptomatic (8 wks, Group A) or symptomatic ages (6 mos, Group B) (FIG. 3D). Decreases in soluble GP levels were observed in C9 metformin treated animals compared to C9 controls in the older Group B but not the younger Group A treatment cohorts (FIGS. 3H-3I).

Figure 3J:
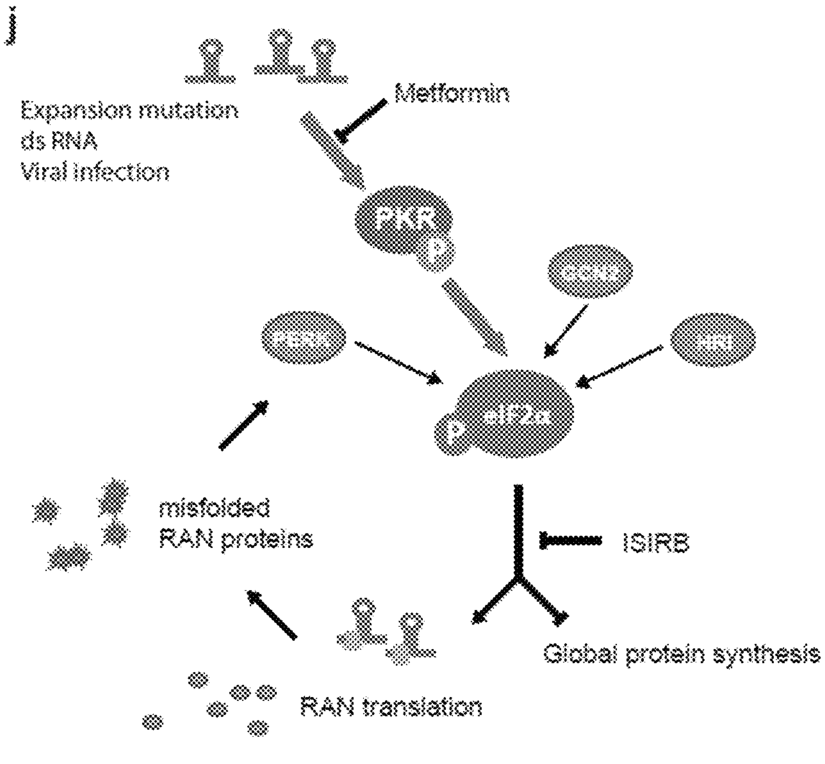

Taken together, data indicate that metformin reduces RAN protein levels in vitro and in vivo, and metformin treatment improves behavior and decreases neuroinflammation in C9 BAC transgenic mice. In some embodiments, data described in this example are consistent with a model in which repeat expansion RNAs lead to chronic activation of the PKR pathway, a condition which results in increased levels of p-eIF2a, decreases in global protein synthesis and the upregulation of RAN translation (FIG. 3J).

Example 4

Figure 5A:
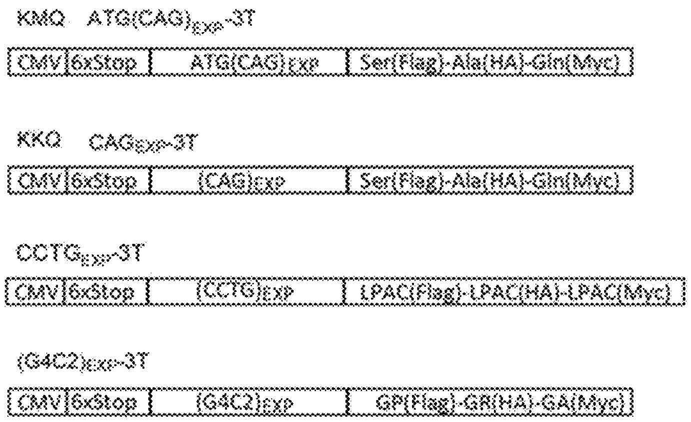
FIGS. 5A-5B show metformin inhibits RAN translation in multiple reading frames in cells that have been transfected with constructs containing CAG, CCTG, or GGGGCC repeat expansion motifs. Protein blots were run on protein lysates from HEK293T cells transfected with various repeat expansion constructs shown in FIG. 5A.
Figure 5B:
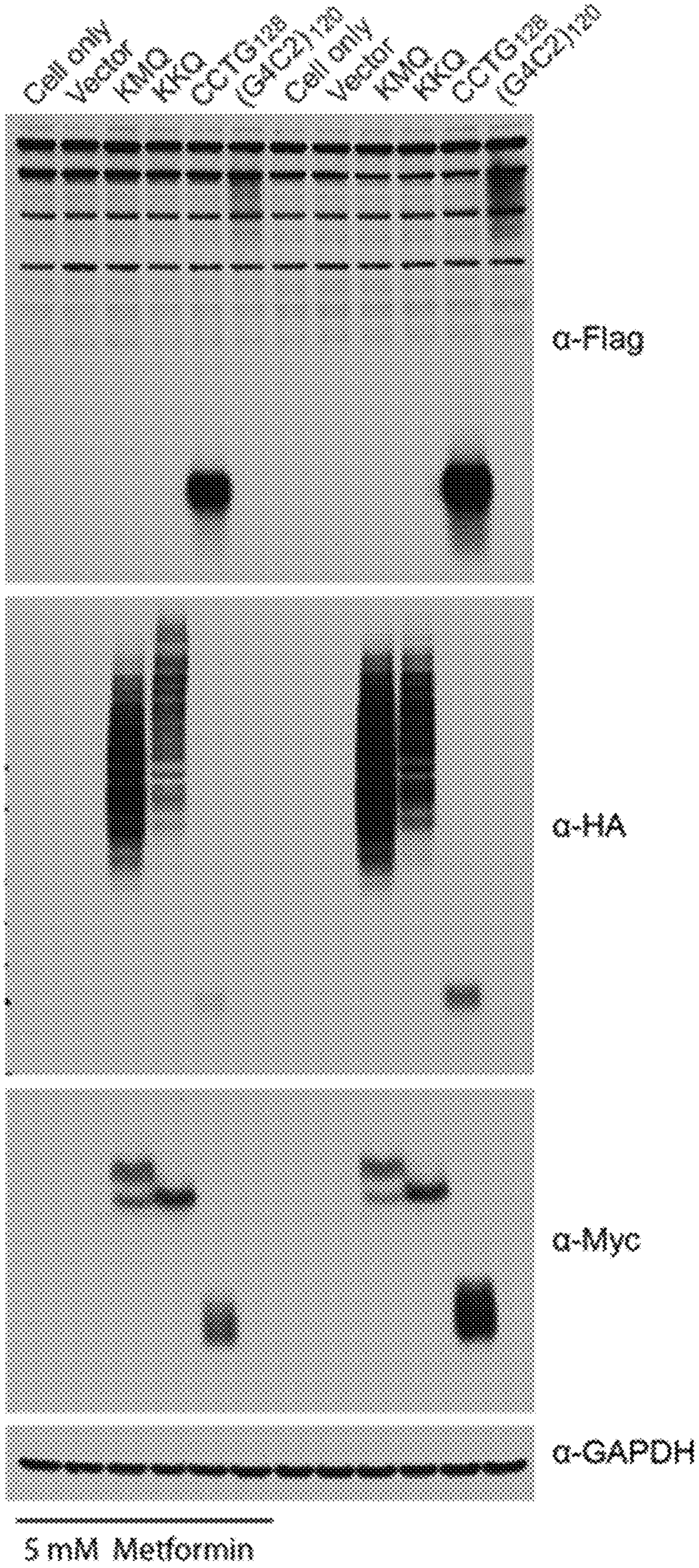

Metformin was evaluated for its effect on RAN protein translation in HEK293T cells that have been transfected with constructs containing CAG, CCTG or GGGGCC repeat expansion motifs. Transfected HEK293T cells were treated with metformin. Protein blots were run on protein lysates from HEK293T cells transfected with various repeat expansion constructs shown in FIG. 5A. In FIG. 5B, the lanes labeled KMQ, show: RAN poly-Ser-Flag, RAN poly-Ala-HA, ATG initiated polyGln-Myc. In FIG. 5B the lanes labeled KMQ has a methionine encoding ATG immediately 5' to the CAG repeat expansion and located within the polyGln reading frame. The lanes labeled KKQ indicate the KKQ vector contains a CAG expansion without an AUG initiation codon, and indicates: RAN polySer-Flag, RAN polyAla-HA, RAN polyGln-Myc. These constructs contain epitope tags that are incorporated into the C-terminal regions of the ATG-initiated poly-Gln and non-ATG initiated RAN proteins (poly-Gln, poly-Leu-Pro-Ala-Cys and poly-Gly-Pro) which are expressed across these repeat expansions. The lane labeled CCTG expresses the following RAN proteins: RAN polyLPAC-Flag, RAN polyLPAC-HA, RAN polyLPAC-Myc. The lane labeled G4C2 is designed to detect the following RAN proteins: RAN polyGP-Flag, RAN polyGR-HA, RAN polyGA-Myc. The protein blots in FIG. 13B show reduced RAN protein levels of the following RAN proteins of poly-LPAC (poly-Leucine-Proline-Alanine-Cysteine) in all three reading frames, poly-Ala, and poly-GP (poly glycine-proline). FIG. 5B shows that metformin inhibits RAN protein accumulation in cells transfected with exemplary repeat expansion constructs. FIG. 5B shows that metformin decreases polyAla, polyLPAC and polyGP RAN protein levels, but not polyGln levels in cells expressing CAG, CCUG or $G4C_2$ expansion RNAs.

Figure 6A:
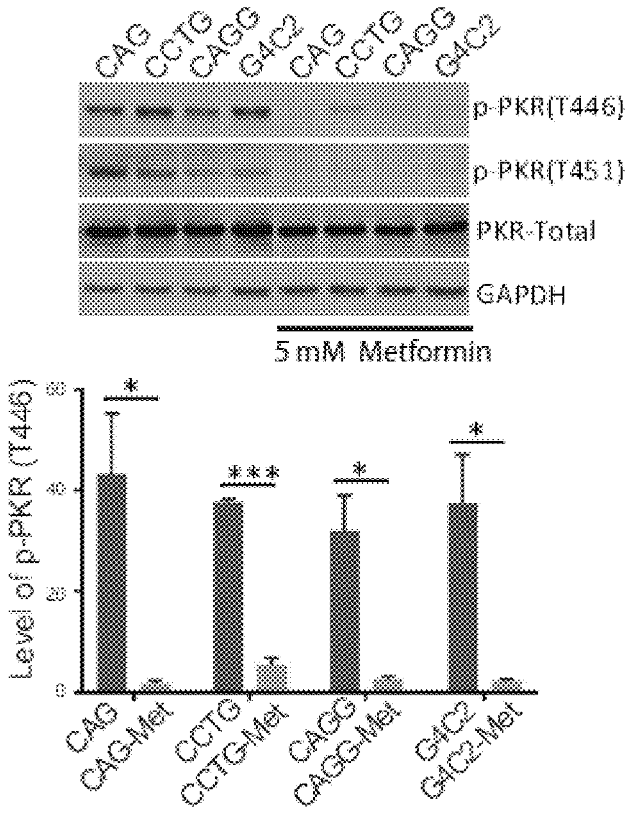
FIG. 6A shows metformin reduces levels of p-PKR (T446 and T451) in HEK293T cells transfected with repeat expansion constructs (n=3/group).

To test if exemplary compound metformin inhibits PKR activation induced by repeat expansion RNAs, repeat expansion transcripts were expressed with or without metformin. Protein blots show that PKR metformin decreases PKR phosphorylation at the T446 and T451 sites, which are required for PKR activation (FIG. 6A). Additionally, exemplary metformin and the exemplary related drugs phenformin and buformin show similar dose-dependent inhibition of $G4C_2$ repeat-expansion induced p-PKR levels and RAN polyGP levels (see FIG. 4). In summary, it is demonstrated that exemplary compound metformin reduces the levels of several types of RAN proteins in mammalian cells and a novel function of metformin as a modulator of PKR phosphorylation has been identified.

Metformin was evaluated for its effect on the steady state levels of glycine-proline (GP) RAN protein detected in vivo in proteins extracted from peripheral blood of a C9ORF72 expansion-positive study subject before and after treatment with metforminC9ORF72. These levels were measured in a human study subject before and after the subject was administered metformin (500 mg or 1000 mg per day Metformin Hydrochloride Extended Release Tablets) at different doses as prescribed by the subject's physician. Dose dependent reduction of glycine-proline (GP) RAN protein levels was observed in blood samples taken from a single human subject with a C9ORF72 repeat expansion compared to pretreatment levels. GP levels were measured in protein lysates from leukocytes isolated from peripheral blood and at multiple time points between 10 and 30 days after treatment with 500 or 1000 mg/day of metformin. *$p<0.05$, ***$p<0.001$, after correction for multiple comparisons.

Figure 6B:
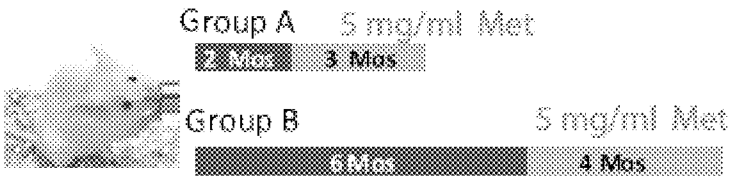
FIG. 6B shows a schematic diagram showing the study design for two metformin treatment groups, with treatment from 2 to 5 months (Group A) or from 6 to 10 months of age (Group B).

Example 5: Evaluation of Exemplary Compound Metformin Ameliorating Neuropathological and Behavioral Phenotypes in the C9-BAC Mouse Model Next, an evaluation of whether exemplary compound metformin can decrease RAN protein levels in vivo and reverse behavioral phenotypes in C9orf72 mice was conducted. C9-BAC and NT mice were treated for 3 months with or without metformin (5 mg/ml) in the drinking water (FIG. 6B), a dose which has previously been shown to result in plasma levels (~10 μM) comparable to conventional human doses of 20 mg/kg/day used in diabetic patients (Chen, Y. et al. Antidiabetic drug metformin (GlucophageR) increases biogenesis of Alzheimer's amyloid peptides via up-regulating BACE1 transcription. *Proc Natl Acad Sci U SA* 106, 3907-3912, doi: 10.1073/pnas.0807991106 (2009); Foretz, M., Guigas, B., Bertrand, L., Pollak, M. & Viollet, B. Metformin: from mechanisms of action to therapies. *Cell Metab* 20, 953-966, doi: 10.1016/j.cmet.2014.09.018 (2014); Memmott, R. M. et al. Metformin prevents tobacco carcinogen—induced lung tumorigenesis. *Cancer Prev Res* (*Phila*) 3, 1066-1076, doi: 10.1158/1940-6207. CAPR-10-0055 (2010)). In Group A animals, three months of treatment began at 2 months of age, before the onset of overt behavioral or pathological phenotypes. In Group B, smaller cohorts of animals were treated for four months beginning at 6 months, an age at which behavioral phenotypes are evident[12].

Figure 6C:
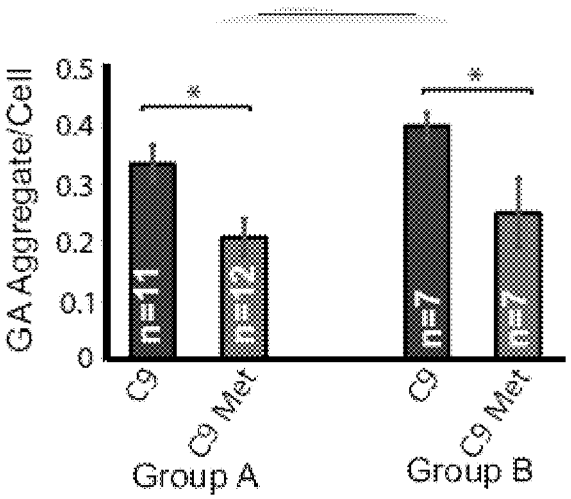
FIG. 6C shows quantification of GA aggregates shows a reduction in GA aggregates in metformin treated compared to untreated C9-BAC mice.
Figure 6D:
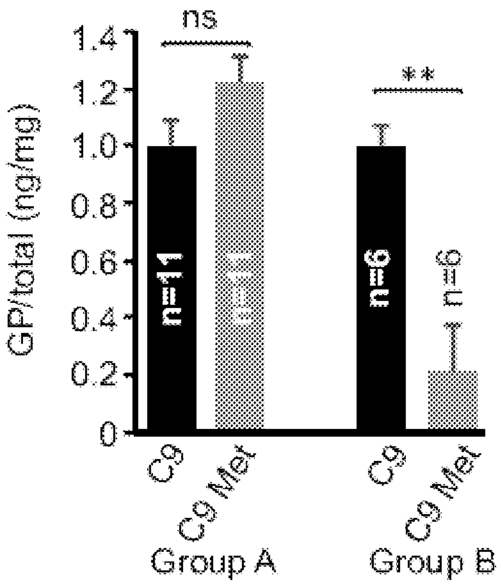
FIG. 6D shows soluble GP levels are reduced Group B but not Group A C9-BAC animals treated with metformin compared to controls.

Molecular characterization showed that $C_9$ metformin treated animals had a 38% (Group A, P=0.01) and 37% (Group B, P=0.047) reduction in the number of GA aggregates in the retrosplenial cortex compared to $C_9$ controls (FIG. 6C). Similarly, C9 metformin treated animals had an ~80% (P=0.0036) decrease in levels of soluble GP compared to C9 controls in the older (Group B) but no significant change was found in the younger (Group A) treatment cohort (FIG. 6C). As a control, it was shown that metformin did not change C9orf72 mRNA levels.

Figure 6E:
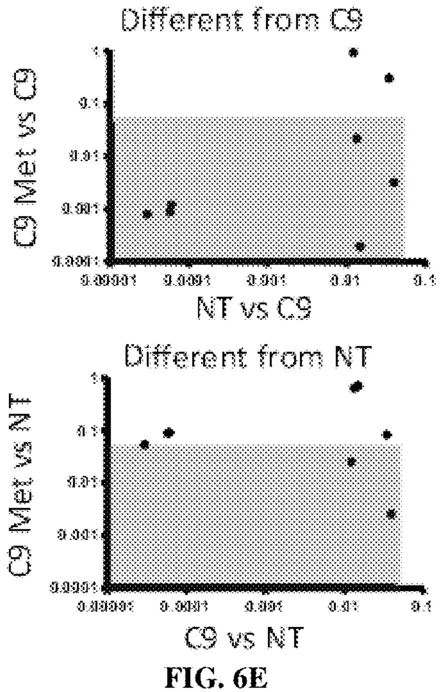
FIG. 6E shows DigiGait analyses showing 6 of 8 parameters that differed between untreated C9-BAC and non-transgenic (NT) littermate controls improved in C9-BAC animals treated with metformin.
Figure 6F:
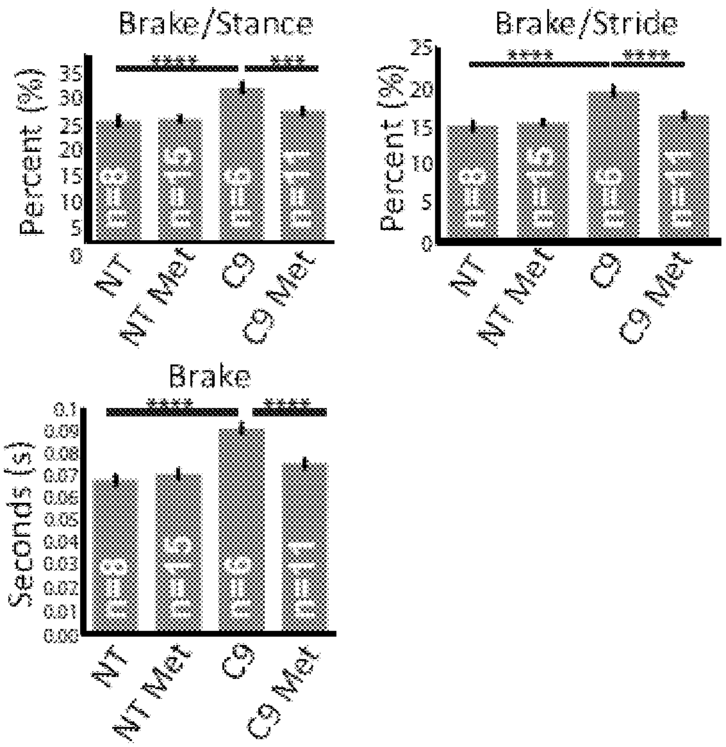
FIG. 6F shows exemplary data of three DigiGait parameters.
Figure 6G:
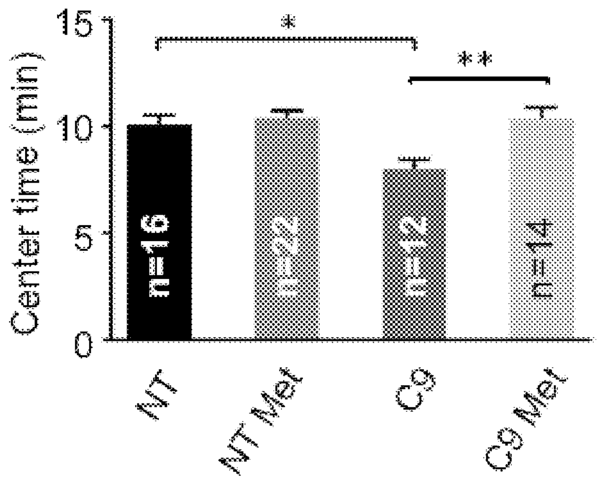
FIG. 6G shows open-field analyses showing increased center time in C9-BAC animals treated with metformin.
Figure 6H:
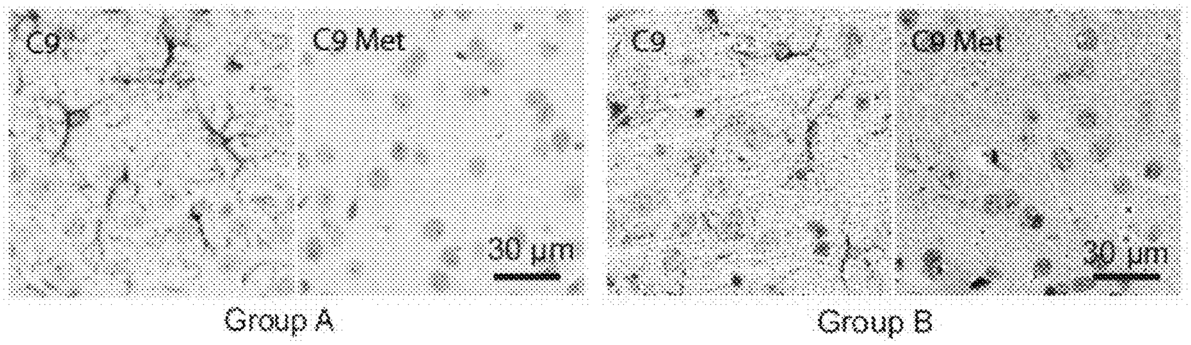
Figure 6I:
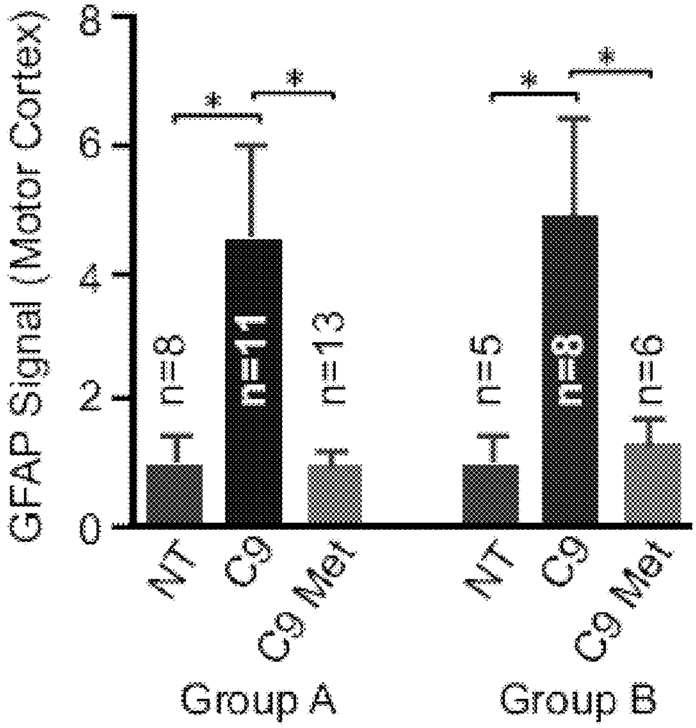

DigiGait analyses of Group A mice at 5 months identified eight parameters that differed between untreated C9 and NT cohorts. In C9 metformin treated mice, six of these parameters improved compared to the C9 water treatment group (FIG. 6E) including, brake, brake/stance and brake/stride (FIG. 6F). Similarly, Group A metformin-treated C9 mice showed normalization or increased center time by open field testing, compared to untreated C9 mice. These data demonstrate that this anxiety-like behavior is improved by metformin treatment (FIG. 6G). IHC staining for glial fibrillary acidic protein (GFAP), a marker of neuroinflammation previously reported in our C9-BAC mice, was reduced by 79% (Group A) and 74% (Group B) in C9 metformin treated animals compared to untreated C9 mice. In contrast, GFAP staining in C9 treated animals was comparable to NT animals (FIG. 6H and FIG. 6I). Taken together, it has been demonstrated that metformin reduces RAN protein levels in vitro and in vivo, and treatment with metformin improves behavior and decreases neuroinflammation in C9 BAC transgenic mice.

REFERENCES

1. Zu, T. et al. Non-ATG-initiated translation directed by microsatellite expansions. *Proc Natl Acad Sci USA* 108, 260-265, doi: 10.1073/pnas.1013343108 (2011).
2. Ash, P. E. et al. Unconventional translation of C9ORF72 GGGGCC expansion generates insoluble polypeptides specific to c9FTD/ALS. *Neuron* 77, 639-646, doi: 10.1016/j.neuron.2013.02.004 (2013).
3. Mori, K. et al. The C9orf72 GGGGCC repeat is translated into aggregating dipeptide-repeat proteins in FTLD/ALS. *Science* 339, 1335-1338, doi: 10.1126/science.1232927 (2013).
4. Zu, T. et al. RAN proteins and RNA foci from antisense transcripts in C9ORF72 ALS and frontotemporal dementia. *Proc Natl Acad Sci USA* 110, E4968-4977, doi: 10.1073/pnas. 1315438110 (2013).
5. Cleary, J. D. & Ranum, L. P. New developments in RAN translation: insights from multiple diseases. *Curr Opin Genet Dev* 44, 125-134, doi: 10.1016/j.gde.2017.03.006 (2017).
6. Green, K. M. et al. RAN translation at C9orf72-associated repeat expansions is selectively enhanced by the integrated stress response. *Nat Commun* 8, 2005, doi: 10.1038/s41467-017-02200-0 (2017).
7. Cheng, W. et al. C9ORF72 GGGGCC repeat-associated non-AUG translation is upregulated by stress through eIF2alpha phosphorylation. *Nat Commun* 9, 51, doi: 10.1038/s41467-017-02495-z (2018).
8. Todd, T. W. & Petrucelli, L. Insights into the pathogenic mechanisms of Chromosome 9 open reading frame 72 (C9orf72) repeat expansions. *J Neurochem* 138 Suppl 1, 145-162, doi: 10.1111/jnc.13623 (2016).
9. Taylor, J. P., Brown, R. H. & Cleveland, D. W. Decoding ALS: from genes to mechanism. *Nature* 539, 197-206, doi: 10.1038/nature20413 (2016).
10. Tian, B. et al. Expanded CUG repeat RNAs form hairpins that activate the double-stranded RNA-dependent protein kinase PKR. RNA 6, 79-87 (2000).
11. Sonenberg, N. & Hinnebusch, A. G. Regulation of translation initiation in eukaryotes: mechanisms and biological targets. *Cell* 136, 731-745, doi: 10.1016/j.cell.2009.01.042 (2009).
12. Liu, Y. et al. C9orf72 BAC Mouse Model with Motor Deficits and Neurodegenerative Features of ALS/FTD. *Neuron* 90, 521-534, doi: 10.1016/j.neuron.2016.04.005 (2016).
13. Benkirane, M. et al. Oncogenic potential of TAR RNA binding protein TRBP and its regulatory interaction with RNA-dependent protein kinase PKR. *EMBO J* 16, 611-624, doi: 10.1093/emboj/16.3.611 (1997).
14. Park, H. et al. TAR RNA-binding protein is an inhibitor of the interferon-induced protein kinase PKR. *Proc Natl Acad Sci USA* 91, 4713-4717 (1994).
15. Pakos-Zebrucka, K. et al. The integrated stress response. *EMBO Rep* 17, 1374-1395, doi: 10.15252/embr.201642195 (2016).
16. Barzilai, N., Crandall, J. P., Kritchevsky, S. B. & Espeland, M. A. Metformin as a Tool to Target Aging. *Cell Metab* 23, 1060-1065, doi: 10.1016/j.cmet.2016.05.011 (2016).
17. Gantois, I. et al. Metformin ameliorates core deficits in a mouse model of fragile X syndrome. *Nat Med* 23, 674-677, doi: 10.1038/nm.4335 (2017).
18. Ma, T. C. et al. Metformin therapy in a transgenic mouse model of Huntington's disease. *Neurosci Lett* 411, 98-103, doi: 10.1016/j.neulet.2006.10.039 (2007).
19. Bañez-Coronel, M. et al. RAN Translation in Huntington Disease. *Neuron* 88, 667-677, doi: 10.1016/j.neuron.2015.10.038 (2015).
20. Chen, Y. et al. Antidiabetic drug metformin (GlucophageR) increases biogenesis of Alzheimer's amyloid peptides via up-regulating BACE1 transcription. *Proc Natl Acad Sci U SA* 106, 3907-3912, doi: 10.1073/pnas.0807991106 (2009).

21. Foretz, M., Guigas, B., Bertrand, L., Pollak, M. & Viollet, B. Metformin: from mechanisms of action to therapies. *Cell Metab* 20, 953-966, doi: 10.1016/j.cmet.2014.09.018 (2014).
22. Memmott, R. M. et al. Metformin prevents tobacco carcinogen—induced lung tumorigenesis. *Cancer Prev Res* (*Phila*) 3, 1066-1076, doi: 10.1158/1940-6207.CAPR-10-0055 (2010).
23. Moon, S. L., Sonenberg, N. & Parker, R. Neuronal Regulation of eIF2alpha Function in Health and Neurological Disorders. *Trends Mol Med* 24, 575-589, doi: 10.1016/j.molmed.2018.04.001 (2018).
24. Zhu, P. J. et al. Suppression of PKR Promotes Network Excitability and Enhanced Cognition by Interferon-gamma-Mediated Disinhibition. *Cell* 147, 1384-1396, doi: 10.1016/j.cell.2011.11.029 (2011).
25. Kioumourtzoglou, M. A. et al. Diabetes Mellitus, Obesity, and Diagnosis of Amyotrophic Lateral Sclerosis: A Population-Based Study. *JAMA Neurol* 72, 905-911, doi: 10.1001/jamaneurol.2015.0910 (2015).
26. Jawaid, A. et al. ALS disease onset may occur later in patients with pre-morbid diabetes mellitus. *Eur J Neurol* 17, 733-739, doi: 10.1111/j.1468-1331.2009.02923.x (2010).
27. Zu, T. et al. RAN Translation Regulated by Muscleblind Proteins in Myotonic Dystrophy Type 2. *Neuron* 95, 1292-1305 e1295, doi: 10.1016/j.neuron.2017.08.039 (2017).
28. Ash P E, Bienick K F, Gendron T F, Caulfield T, Lin W L, Dejesus-Hernandez M, van Blitterswijk M M, Jansen-West K, Paul J W, 3rd, Rademakers R et al. 2013. Unconventional translation of C9ORF72 GGGGCC expansion generates insoluble polypeptides specific to c9FTD/ALS. *Neuron* 77: 639-646.
29. Banez-Coronel M, Ayhan F, Tarabochia A D, Zu T, Perez B A, Tusi S K, Pletnikova O, Borchelt D R, Ross C A, Margolis R L et al. 2015. RAN Translation in Huntington Disease. *Neuron* 88: 667-677.
30. Cleary J D, Ranum L P. 2017. New developments in RAN translation: insights from multiple diseases. *Curr Opin Genet Dev* 44: 125-134.
31. Mori K, Weng S M, Arzberger T, May S, Rentzsch K, Kremmer E, Schmid B, Kretzschmar H A, Cruts M, Van Broeckhoven C et al. 2013. The C9orf72 GGGGCC repeat is translated into aggregating dipeptide-repeat proteins in FTLD/ALS. *Science* 339: 1335-1338.
32. Todd P K, Oh S Y, Krans A, He F, Sellier C, Frazer M, Renoux A J, Chen K C, Scaglione K M, Basrur V et al. 2013. CGG repeat-associated translation mediates neurodegeneration in fragile X tremor ataxia syndrome. *Neuron* 78: 440-455.
33. Zu T, Gibbens B, Doty N S, Gomes-Pereira M, Huguet A, Stone M D, Margolis J, Peterson M, Markowski T W, Ingram M A et al. 2011. Non-ATG-initiated translation directed by microsatellite expansions. *Proc Natl Acad Sci USA* 108: 260-265.
34. Zu T, Liu Y, Banez-Coronel M, Reid T, Pletnikova O, Lewis J, Miller T M, Harms M B, Falchook A E, Subramony S H et al. 2013. RAN proteins and RNA foci from antisense transcripts in C9ORF72 ALS and frontotemporal dementia. *Proc Natl Acad Sci USA* 110: E4968-4977.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a neurological disease associated with repeat expansions in a subject in need thereof, the method comprising administering to the subject in need thereof an effective amount of a compound of Formula (I):

(I)

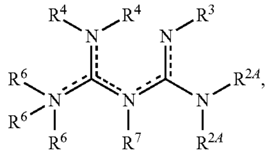

or a pharmaceutically acceptable salt, tautomer, or stereoisomer thereof, wherein:

each instance of - - - is a single bond or double bond, as valency permits;

each instance of $R^{2A}$ is independently hydrogen or substituted or unsubstituted $C_{1-6}$ alkyl;

$R^3$ is hydrogen or unsubstituted $C_{1-6}$ alkyl;

each instance of $R^4$ is independently hydrogen, unsubstituted $C_{1-6}$ alkyl, or absent, as valency permits;

each instance of $R^6$ is independently hydrogen, unsubstituted $C_{1-6}$ alkyl, or absent, as valency permits; and $R^7$ is hydrogen, unsubstituted $C_{1-6}$ alkyl, or absent, as valency permits;

wherein the neurological disease associated with repeat expansions is spinocerebellar ataxia type 1, 2, 3, 6, 7, 8, 12, or 17.

2. The method of claim 1, wherein the compound is of Formula (I-A):

(I-A)

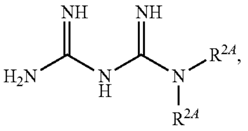

or a pharmaceutically acceptable salt, tautomer, or stereoisomer thereof.

3. The method of claim 1, wherein the compound is of formula:

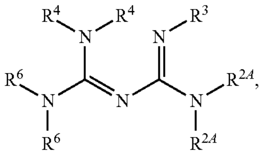

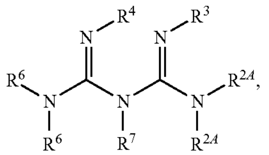

or

-continued

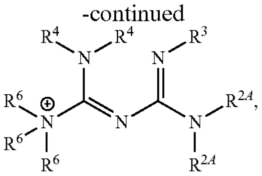

or a pharmaceutically acceptable salt, tautomer, or stereoisomer thereof.

4. The method of claim 1, wherein at least one instance of $R^{2A}$ is substituted or unsubstituted $C_{1-6}$ alkyl.

5. The method of claim 1, wherein $R^3$ is hydrogen.

6. The method of claim 1, wherein at least one instance of $R^6$ is hydrogen.

7. The method of claim 1, wherein the compound is of formula:

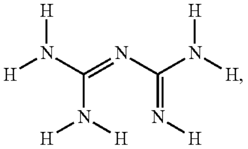 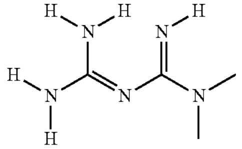,

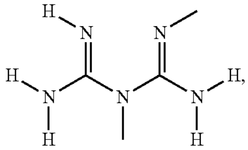 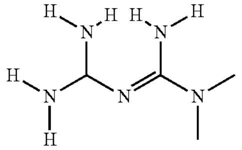,

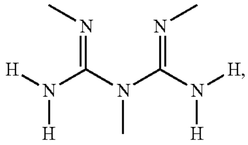 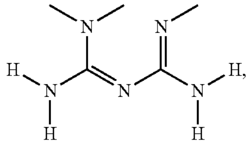

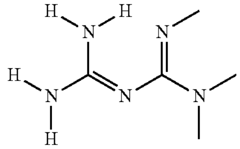, 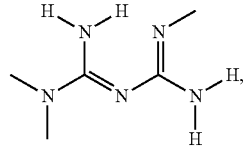

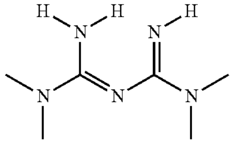, 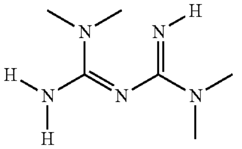,

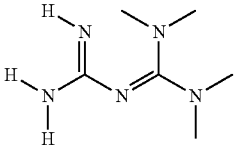, 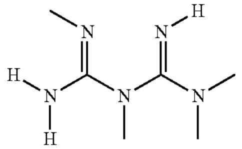,

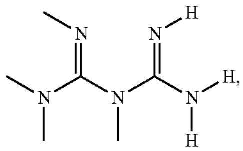 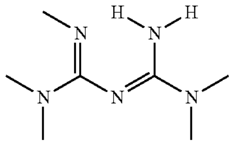,

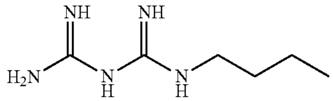,

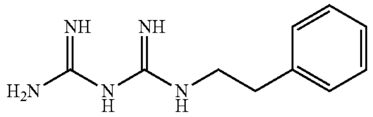,

-continued

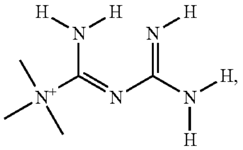 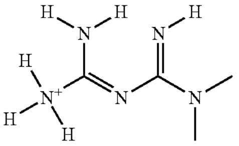, or

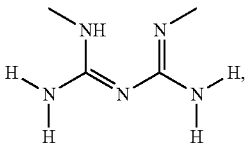

or a pharmaceutically acceptable salt, tautomer, or stereoisomer thereof.

8. The method of claim 1, wherein the compound is of formula:

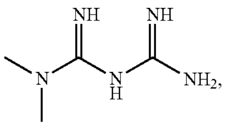 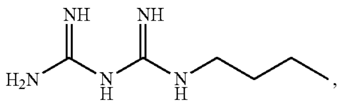,

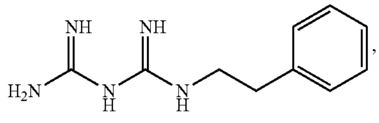, or

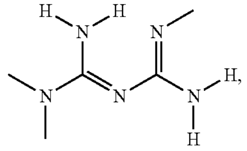

or a pharmaceutically acceptable salt, tautomer, or stereoisomer thereof.

9. The method of claim 1, whereby the method comprises reducing the level of one or more repeat associated non-ATG (RAN) proteins, and/or reducing the translation of one or more RAN proteins.

10. The method of claim 1, wherein the neurological disease associated with repeat expansions is spinocerebellar ataxia type 8.

11. The method of claim 1, wherein the neurological disease associated with repeat expansions is spinocerebellar ataxia type 1, spinocerebellar ataxia type 2, spinocerebellar ataxia type 3, spinocerebellar ataxia type 6, spinocerebellar ataxia type 7, spinocerebellar ataxia type 12, or spinocerebellar ataxia type 17.

12. The method of claim 1, wherein each instance of $R^4$ is independently hydrogen or absent, as valency permits; and $R^7$ is hydrogen or absent, as valency permits.

13. The method of claim 1, wherein the method comprises administering to the subject in need thereof an effective amount of the compound, or a pharmaceutically acceptable salt thereof.

14. The method of claim 1, wherein the method comprises administering to the subject in need thereof an effective amount of a compound of the formula:

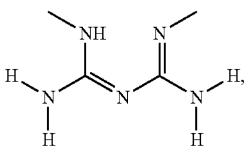
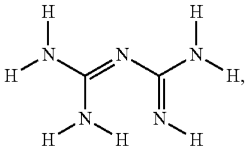
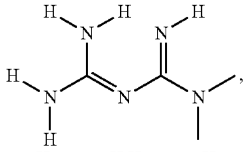
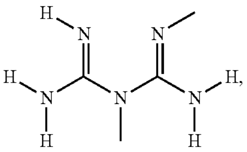
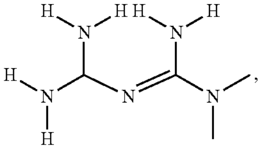
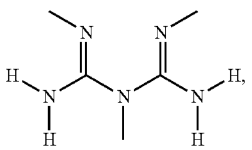
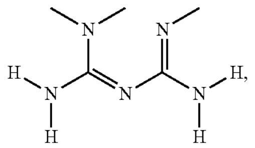
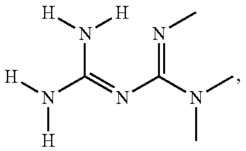
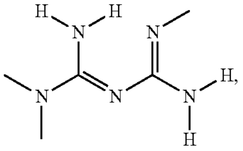
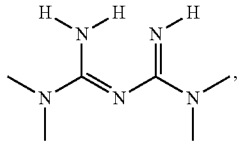
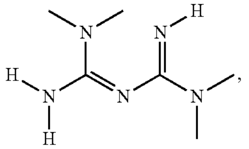
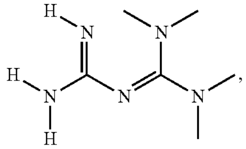
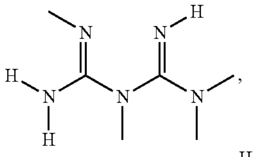
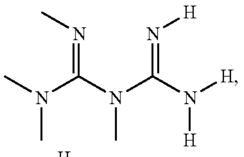
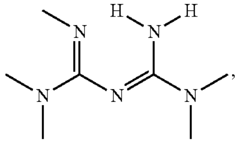
-continued
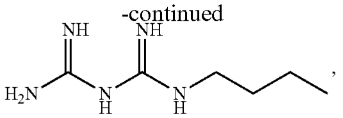
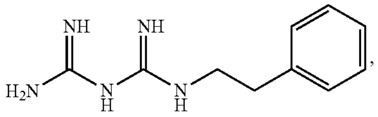
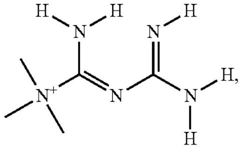
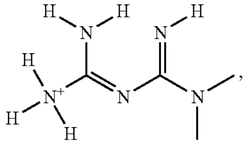
or
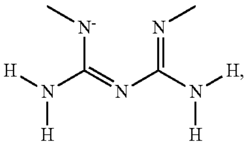
or a pharmaceutically acceptable salt thereof.
15. The method of claim 1, wherein the method comprises administering to the subject in need thereof an effective amount of a compound of the formula:
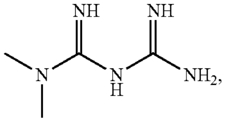
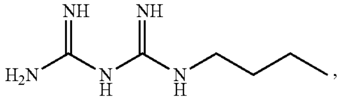
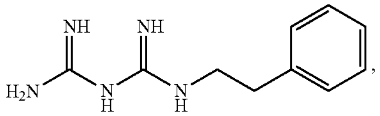
or
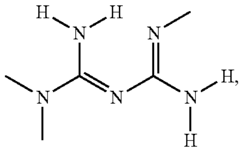
or a pharmaceutically acceptable salt thereof.
* * * * *